United States Patent [19]
Miller et al.

[11] Patent Number: 5,939,318
[45] Date of Patent: Aug. 17, 1999

[54] CHOLESTEROL DISPOSAL FUSION ENZYMES

[75] Inventors: Walter L. Miller, San Francisco, Calif.; Jennifer A. Harikrishna, Kuala Lumpur, Malaysia; Stephen M. Black, Concord, Calif.

[73] Assignee: Regents of the University of California, Oakland, Calif.

[21] Appl. No.: 08/564,090

[22] PCT Filed: Jun. 9, 1994

[86] PCT No.: PCT/US94/06698

§ 371 Date: Feb. 5, 1996

§ 102(e) Date: Feb. 5, 1996

[87] PCT Pub. No.: WO94/29434

PCT Pub. Date: Dec. 22, 1994

Related U.S. Application Data

[63] Continuation-in-part of application No. 08/075,193, Jun. 9, 1993, Pat. No. 5,547,868.

[51] Int. Cl.$^6$ .............................. C12N 5/10; C12N 1/21; C12N 15/62; C12N 15/79
[52] U.S. Cl. .................. 435/325; 435/69.1; 435/70.1; 435/70.3; 435/71.1; 435/172.3; 435/183; 435/188; 435/189; 435/252.3; 435/254.11; 435/320.1; 435/375; 536/23.2; 536/23.4; 536/23.5
[58] Field of Search .................. 435/69.1, 70.1, 435/70.3, 71.1, 172.3, 183, 188, 189, 252.3, 254.11, 320.1, 325, 375; 536/23.2, 23.4, 23.5; 530/401

[56] References Cited

U.S. PATENT DOCUMENTS

| | | | |
|---|---|---|---|
| 3,856,780 | 12/1974 | Narwid et al. | 540/118 |
| 4,736,866 | 4/1988 | Leder e tal. | 800/2 |
| 5,045,471 | 9/1991 | Miller | 435/320.1 |
| 5,075,229 | 12/1991 | Hanson et al. | 435/172.3 |
| 5,114,857 | 5/1992 | Yabusaki et al. | 435/184 |
| 5,164,313 | 11/1992 | Gelboin et al. | 435/189 |
| 5,240,831 | 8/1993 | Barnes | 435/184 |

OTHER PUBLICATIONS

Adamovich et al., (1989) "Selective Chemical Modification of Cytochrome P–450$_{scc}$ Lysine Residues. Identification of Lysines Involved in the Interaction with Adrenodoxin" *Biochimica et Biophysica Acta* 996:247–253.

Akiyoshi–Shibata et al., (1991) "Expression of Bovine Adrenodoxin and NADPH–Adrenodoxin Reductase cDNAs in *Saccharomyces cerevisiae*" *DNA and Cell Biology* 10:613–621.

Argos, (1990) "An Investigation of Oligopeptides Linking Domains in Protein Tertiary Structures and Possible Candidates for General Gene Fusion" *J. Mol. Biol.* 211:943–958.

Black, Shaun D. (1992) "Membrane Topology of the Mammalian P450 Cytochromes" *The FASEB Journal* 6:680–685.

Black, Stephen M. et al., (1993) "Regulation of Proteins in the Cholesterol Side–Chain Cleavage System in JEG–3 and Y–1 Cells" *Endocrinology* 132:539–545.

Brandt et al., (1992) "Expression and Characterization of Human Mitochondrial Ferredoxin Reductase in *Escherichia coli*" *Archives of Biochemistry and Biophysics* 294:735–740.

Bredt et al., (1991) "Cloned and Expressed Nitric Oxide Synthase Structurally Resembles Cytochrome P–450 Reductase" *Nature* 351:714–718.

Brentano et al., (1992) "cAMP Post–Transcriptionally Diminishes the Abundance of Adrenodoxin Reductase mRNA" *Proc. Natl. Acad. Sci. USA* 89:4099–4103.

Brentano et al., (1992) "Regulation of Human Cytochrome P450scc and Adrenodoxin Messenger Ribonucleic Acids in JEG–3 Cytotrophoblasts Cells" *Endocrinology* 131:3010–3018.

Brinster et al., (1988) "Introns Increase Transcriptional Efficiency in Transgenic Mice" *Proc. Natl. Acad. Sci. USA* 85:836–840.

Chung et al., (1986) "Human Cholesterol Side–Chain Cleavage Enzyme, P450scc: cDNA Cloning, Assignment of the Gene to Chromosome 15, and Expression in the Placenta" *Proc. Natl. Acad. Sci. USA* 83:8962–8966.

Chung et al., (1987) "Cytochrome P450c17 (steroid 17α–hydroxylase/17,20 lyase): Cloning of Human Adrenal and Testis cDNAs Indicates the Same Gene is Expressed in Both Tissues" *Proc. Natl. Acad. Sci. USA* 84:407–411.

Clark et al., (1993) "Enhancing the Efficiency of Transgene Expression" *Phil. Trans. R. Soc. Lond. B* 339:225–232.

Coghlan et al., (1992) "Electrostatic Interactions Stabilizing Ferredoxin Electron Transfer Complexes" *J. Biol. Chem.* 267:8932–8935.

Cook et al., (1993) "Liver–Specific Expression of a Phosphoenolpyruvate Carboxykinase–neo Gene in Genetically Modified Chickens" *Poultry Science* 72:554–567.

Fisher et al., (Nov. 1992) "High Level Expression of Mammalian Cytochromes P450 . . . " *PNAS* 89:10817–10821.

Gorski et al., (1986) "Tissue–Specific In Vitro Transcription from the Mouse Albumin Promoter" *Cell* 47:767–776.

Graves et al., (1992) "Analysis of a Tissue–Specific Enhancer: ARF6 Regulates Adipogenic Gene Expression" *Molecular and Cellular Biology* 12:1202–1208.

Hanukoglu et al., (1980) "Mitochondrial Cytochrome P–450$_{scc}$" *J. Biol. Chem.* 255:3057–3061.

(List continued on next page.)

*Primary Examiner*—Charles C. P. Rories
*Attorney, Agent, or Firm*—Cooley Godward LLP

[57] ABSTRACT

Fusion enzymes having multiple segments of different biological activity including one segment having P450scc activity and at least one segment having electron-transfer activity for transferring electrons to P450scc are described along with genetic constructs for production of such enzymes and methods for their use. Methods for their use include cholesterol degradation in vitro or in vivo as well as conversion of cholesterol to other useful steroidal products including pregnenolone.

22 Claims, 16 Drawing Sheets

OTHER PUBLICATIONS

Hanukoglu et al., (1989) "cDNA Sequence of Adrenodoxin Reductase—Identification of NADP–binding Sites in Oxidoreductases" *Eur. J. Biochem.* 180:479–484.

Harikrishna et al. (Jun. 1993) "Construction and Function of Fusion Enzymes of the Human Cytochrome P450SCC System|", *DNA Cell Biol.*, 12(5):371–379.

Kumamoto et al., (1989) "Critical Region in the Extension Peptide for the Import of Cytochrome" *J. Biochem*, 105:72–78.

Kuwada et al., (1991) "Purification and Properties of Cytochrome P–450 (scc) from Pig Testis Mitochondria" *Biochem. Biophys. Res. Commun.* 176:1501–1508.

Lambeth et al., (1983) "Cytochrome P–450$_{scc}$–Adrenodoxin Complex" *J. Biol. Chem.* 258:5596–5602.

Langer et al., (1993) "Tissue Engineering" *Science* 260:920–926.

Lin et al., (1990) "Cloning and Sequence of the Human Adrenodoxin Reductase Gene" *Proc. Natl. Acad. Sci. USA* 87:8516–8520.

Miller, (1988) "Molecular Biology of Steroid Hormone Synthesis" *Endochrine Reviews* 9:295–318.

Monier et al., (1988) "Signals for the Incorporation and Orientation of Cytochrome P450 in the Endoplasmic Reticulum Membrane" *J. Cell Biol.* 107:457–470.

Morohashi et al., (1984) "Molecular Cloning and Nucleotide Sequence of cDNA for mRNA of Mitochondrial Cytochrome P–450(scc) of Bovine Adrenal Cortex" *Proc. Natl. Acad. Sci. USA* 81:4647–4651.

Murakami et al., (1987) "A Genetically Engineered P450 Monooxygenase: Construction of the Functional Fused Enzyme Between Rat Cytochrome P450c and NADPH–Cytochrome P450 Reductase" *DNA* 6:189–197.

Nakajin et al., (1985) "Cytochrome $b_5$ Promotes the Synthesis of $\Delta^{16}$–$C_{19}$ Steroids by Homogenous Cytochrome P–450 $C_{21}$ Side–Chain Cleavage from Pig Testis" *Biochem. and Biophys. Res. Comm.* 132:708–713.

Narhi et al., (1986) "Characterization of a Catlytically Self–sufficient 119,000–Dalton Cytochrome P–450 Monooxygenase Induced by Barbituates in *Bacillus megaterium*" *J. Biol. Chem.* 261:7160–7169.

Narhi et al., (1987) "Identification and Characterization of Two Functional Domains in Cytochrome P–450$_{BM-3}$, a Catlytically Self–sufficient Monooxygenase Induced by Barbituates in *Bacillus megaterium*" *J. Biol. Chem.* 262:6683–6690.

Nelson et al., (1993) "The P450 Superfamily: Update on New Sequences, Gene Mapping, Accession Numbers, Early Trivial Names of Enzymes, and Nomenclature" *DNA and Cell Biology* 12:1–51.

Okamura et al., (1985) "Molecular Cloning and Amino Acid Sequence of the Precursor Form of Bovine Adrenodoxin: Evidence for a Previously Unidentified COOH–terminal Peptide" *Proc. Natl. Acad. Sci. USA* 82:5705–5709.

Omdahl et al., (1992) "Molecular Cloning and Immunological Characterization of Porcine Kidney Ferredoxin" *Archives of Biochemistry and Biophysics* 293:213–218.

Palin et al., (1992) "Direct Expression of Mature Bovine Adrenodoxin in *Escherichia coli*" *Archives of Biochemistry and Biophysics* 295:126–131.

Picado–Leonard et al., (1988) "Human Adrenodoxin: Cloning of Three cDNAs and Cycloheximide Enhancement in JEG–3 Cells" *J. Biol. Chem.* 263:3240–3244.

Porter et al., (1985) "Coding Nucleotide Sequence if Rat NADPH–Cytochrome P–450 Oxidoreductase cDNA and Identification of Flavin–binding Domains" *Proc. Natl. Acad. Sci. USA* 82:973–977.

Rubin et al., (1991) "Expression of Human Apolipoprotein A–I in Transgenic Mice Results in Reduced Plasma Levels of Murine Apolipoprotein A–I and the Appearance of Two New High Density Lipoprotein Size Subclasses" *Proc. Natl. Acad. Sci. USA* 88:434–438.

Rubin et al., (1991) "Inhibition of Early Atherogenesis in Transgenic Mice by Human Apolipoprotein AI" *Nature* 353:265–267.

Ruettinger et al., (1989) "Coding Nucleotide, 5' Regulatory, and Deduced Amino Acid Sequences of P–450$_{BM-3}$, a Single Peptide Cytochrome P–450:NADPH–P–450 Reductase from *Bacillus megaterium*" *J. Biol. Chem.* 264:10987–10995.

Sagara et al., (1987) "Cloning and Sequence Analysis of Adrenodoxin Reductase cDNA from Bovine Adrenal Cortex" *J. Biochem.* 102:1333–1336.

Sakaki et al., (1990) "Expression of Bovine Cytochrome P450c21 and Its Fused Enzymes with Yeast NADPH–Cytochrome P450 Reductase in *Saccharomyces cerevisiae*" *DNA and Cell Biology* 9:603–614.

Santoro et al., (1991) "Identification of Single–Stranded–DNA–Binding Proteins That Interact with Muscle Gene Elements" *Mol. Cell. Biol.* 11:1944–1953.

Shibata et al., (1990) "Genetically Engineered P450 Monooxygenases: Construction of Bovine P450c17/Yeast Reductase Fused Enzymes" *DNA and Cell Biology* 9:27–36.

Solish et al., (1988) "Human Adrenodoxin Reductase: Two mRNAs Encoded by a Single Gene on Chromosome 17cen→q25 are Expressed in Steroidogenic Tissues" *Proc. Natl. Acad. Sci. USA* 85:7104–7108.

Wada et al., (1991) "Expression of Functional Bovine Cholesterol Side Chain Cleavage Cytochrome P450 (P450scc) in *Escherichia coli*" *Archives of Biochemistry and Biophysics* 290:376–380.

Wada et al., (1991) "Codon Usage Tabulated from the GenBank Genetic Sequence Data" *Nucleic Acids Research* 19:1981–1986.

Walsh, (1989) "Cross–Binding of Factors to Functionally Different Promoter Elements in c–fos and Skeletal Actin Genes" *Mol. Cell. Biol.* 9:2191–2201.

Yabusaki et al., (1988) "Genetically Engineered Modification of P450 Monooxygenases: Functional Analysis of the Amino–Terminal Hydrophobic Region and Hinge Region of the P450/Reductase Fused Enzyme" *DNA* 7:701–711.

Yamano et al., (1989) "Human NADPH–P450 Oxidoreductase: Complementary DNA Cloning, Sequence and Vaccinia Virus–Mediated Expression and Localization of the CYPOR Gene to Chromosome 7" *Molec. Pharm.* 35:83–88.

Yokode et al., (1990) "Diet–Induced Hypercholesterolemia in Mice: Prevention by Overexpression of LDL Receptors" *Science* 250:1273–1275.

Zuber et al., (1988) "Simultaneous Transfection of COS–1 Cells with Mitochondrial and Microsomal Steroid Hydorxylases: Incorporation of a Steroidogenic Pathway into Nonsteroidogenic Cells" *Proc. Natl. Adad. Sci. USA* 85:699–703.

Morohashi et al., (1987) "Gene Structure of Human Cytochrome P–450 (scc), Cholesterol Demolase" *J. Biochem.* 101:879–887.

```
                           GGGCGCTGAAGTGGAGCAGGTACAGTCACAGCTGTGGGGACAGC
     1                                      10
     Met Leu Ala Lys Gly Leu Pro Pro Arg Ser Val Leu Val Lys Gly
     ATG CTG GCC AAG GGT CTT CCC CCA CGC TCA GTC CTG GTC AAA GGC 20                                      30
     Tyr Gln Thr Phe Leu Ser Ala Pro Arg Glu Gly Leu Gly Arg Leu
     TAC CAG ACC TTT CTG AGT GCC CCC AGG GAG GGG CTG GGG CGT CTC

40
     Arg Val Pro Thr Gly Glu Gly Ala Gly Ile Ser Thr Arg Ser Pro
     AGG GTG CCC ACT GGC GAG GGA GCT GGC ATC TCC ACC CGC AGT CCT 50                                      60
     Arg Pro Phe Asn Glu Ile Pro Ser Pro Gly Asp Asn Gly Trp Leu
     CGC CCC TTC AAT GAG ATC CCC TCT CCT GGT GAC AAT GGC TGG CTA

70
     Asn Leu Tyr His Phe Trp Arg Glu Thr Gly Thr His Lys Val His
     AAC CTG TAC CAT TTC TGG AGG GAG ACG GGC ACA CAC AAA GTC CAC 80                                      90
     Leu His His Val Gln Asn Phe Gln Lys Tyr Gly Pro Ile Tyr Arg
     CTT CAC CAT GTC CAG AAT TTC CAG AAG TAT GGC CCG ATT TAC AGG

100
     Glu Lys Leu Gly Asn Val Glu Ser Val Tyr Val Ile Asp Pro Glu
     GAG AAG CTC GGC AAC GTG GAG TCG GTT TAT GTC ATC GAC CCT GAA 110                                     120
     Asp Val Ala Leu Leu Phe Lys Ser Glu Gly Pro Asn Pro Glu Arg
     GAT GTG GCC CTT CTC TTT AAG TCC GAG GGC CCC AAC CCA GAA CGA

130
     Phe Leu Ile Pro Pro Trp Val Ala Tyr His Gln Tyr Tyr Gln Arg
     TTC CTC ATC CCG CCC TGG GTC GCC TAT CAC CAG TAT TAC CAG AGA 140                                     150
     Pro Ile Gly Val Leu Leu Lys Lys Ser Ala Ala Trp Lys Lys Asp
     CCC ATA GGA GTC CTG TTG AAG AAG TCG GCA GCC TGG AAG AAA GAC

160
     Arg Val Ala Leu Asn Gln Glu Val Met Ala Pro Glu Ala Thr Lys
     CGG GTG GCC CTG AAC CAG GAG GTG ATG GCT CCA GAG GCC ACC AAG 170                                     180
     Asn Phe Leu Pro Leu Leu Asp Ala Val Ser Arg Asp Phe Val Ser
     AAC TTT TTG CCC CTG TTG GAT GCA GTG TCT CGG GAC TTC GTC AGT

190
     Val Leu His Arg Arg Ile Lys Lys Ala Gly Ser Gly Asn Tyr Ser
     GTC CTG CAC AGG CGC ATC AAG AAG GCG GGC TCC GGA AAT TAC TCG
```

FIG.1A

```
                          200                                    210
Gly Asp Ile Ser Asp Asp Leu Phe Arg Phe Ala Phe Glu Ser Ile
GGG GAC ATC AGT GAT GAC CTG TTC CGC TTT GCC TTT GAG TCC ATC

220
Thr Asn Val Ile Phe Gly Glu Arg Gln Gly Met Leu Glu Glu Val
ACT AAC GTC ATT TTT GGG GAG CGC CAG GGG ATG CTG GAG GAA CTA 230                                    240
Val Asn Pro Glu Ala Gln Arg Phe Ile Asp Ala Ile Tyr Gln Met
CTG AAC CCC GAG GCC CAG CGA TTC ATT GAT GCC ATC TAC CAG ATG

250
Phe His Thr Ser Val Pro Met Leu Asn Leu Pro Pro Asp Leu Phe
TTC CAC ACC AGC GTC CCC ATG CTC AAC CTT CCC CCA GAC CTG TTC 260                                    270
Arg Leu Phe Arg Thr Lys Thr Trp Lys Asp His Val Ala Ala Trp
CGT CTG TTC AGG ACC AAG ACC TGG AAG GAC CAT GTG GCT GCA TGG

280
Asp Val Ile Phe Ser Lys Ala Asp Ile Tyr Thr Gln Asn Phe Tyr
GAC GTG ATT TTC AGT AAA GCT GAC ATA TAC ACC CAG AAC TTC TAC 290                                    300
Trp Glu Leu Arg Gln Lys Gly Ser Val His His Asp Tyr Arg Gly
TGG GAA TTG AGA CAG AAA GGA AGT GTT CAC CAC GAT TAC CGT GGC

310
Met Leu Tyr Arg Leu Leu Gly Asp Ser Lys Met Ser Phe Glu Asp
ATG CTC TAC AGA CTC CTG GGA GAC AGC AAG ATG TCC TTC GAG GAC 320                                    330
Ile Lys Ala Asn Val Thr Glu Met Leu Ala Gly Gly Val Asp Thr
ATC AAG GCC AAC GTC ACA GAG ATG CTG GCA GGA GGG GTG GAC ACG

340
Thr Ser Met Thr Leu Gln Trp His Leu Tyr Glu Met Ala Arg Asn
ACG TCC ATG ACC CTG CAG TGG CAC TTG TAT GAG ATG GCA CGC AAC 350                                    360
Leu Lys Val Gln Asp Met Leu Arg Ala Glu Val Leu Ala Ala Arg
CTG AAG GTG CAG GAT ATG CTG CGG GCA GAG GTC TTG GCT GCG CGG

370
His Gln Ala Gln Gly Asp Met Ala Thr Met Leu Gln Leu Val Pro
CAC CAG GCC CAG GGA GAC ATG GCC ACG ATG CTA CAG CTG GTC CCC 380                                    390
Leu Leu Lys Ala Ser Ile Lys Glu Thr Leu Arg Leu His Pro Ile
CTC CTC AAA GCC AGC ATC AAG GAG ACA CTA AGA CTT CAC CCC ATC

400
Ser Val Thr Leu Gln Arg Tyr Leu Val Asn Asp Leu Val Leu Arg
TCC GTG ACC CTG CAG AGA TAT CTT GTA AAT GAC TTG GTT CTT CGA
```

FIG.1B

|  |  |  |  | 410 |  |  |  |  |  |  |  | 420 |
|---|---|---|---|---|---|---|---|---|---|---|---|---|
| Asp | Tyr | Met | Ile | Pro | Ala | Lys | Thr | Leu | Val | Gln | Val | Ala | Ile | Tyr |
| GAT | TAC | ATG | ATT | CCT | GCC | AAG | ACA | CTG | GTG | CAA | GTG | GCC | ATC | TAT |

|  |  |  |  |  |  |  |  | 430 |  |  |  |  |
|---|---|---|---|---|---|---|---|---|---|---|---|---|
| Ala | Leu | Gly | Arg | Glu | Pro | Thr | Phe | Phe | Phe | Asp | Pro | Glu | Asn | Phe |
| GCT | CTG | GGC | CGA | GAG | CCC | ACC | TTC | TTC | TTC | GAC | CCG | GAA | AAT | TTT |

|  |  |  |  | 440 |  |  |  |  |  |  |  | 450 |
|---|---|---|---|---|---|---|---|---|---|---|---|---|
| Asp | Pro | Thr | Arg | Trp | Leu | Ser | Lys | Asp | Lys | Asn | Ile | Thr | Tyr | Phe |
| GAC | CCA | ACC | CGA | TGG | CTG | AGC | AAA | GAC | AAG | AAC | ATC | ACC | TAC | TTC |

|  |  |  |  |  |  |  |  | 460 |  |  |  |  |
|---|---|---|---|---|---|---|---|---|---|---|---|---|
| Arg | Asn | Leu | Gly | Phe | Gly | Trp | Gly | Val | Arg | Gln | Cys | Leu | Gly | Arg |
| CGG | AAC | TTG | GGC | TTT | GGC | TGG | GGT | GTG | CGG | CAG | TGT | CTG | GGA | CGG |

|  |  |  |  | 470 |  |  |  |  |  |  |  | 480 |
|---|---|---|---|---|---|---|---|---|---|---|---|---|
| Arg | Ile | Ala | Glu | Leu | Glu | Met | Thr | Ile | Phe | Leu | Ile | Asn | Met | Leu |
| CGG | ATC | GCT | GAG | CTA | GAG | ATG | ACC | ATC | TTC | CTC | ATC | AAT | ATG | CTG |

|  |  |  |  |  |  |  |  | 490 |  |  |  |  |
|---|---|---|---|---|---|---|---|---|---|---|---|---|
| Glu | Asn | Phe | Arg | Val | Glu | Ile | Gln | His | Leu | Ser | Asp | Val | Gly | Thr |
| GAG | AAC | TTC | AGA | GTT | GAA | ATC | CAA | CAC | CTC | AGC | GAT | GTG | GGC | ACC |

|  |  |  |  | 500 |  |  |  |  |  |  |  | 510 |
|---|---|---|---|---|---|---|---|---|---|---|---|---|
| Thr | Phe | Asn | Leu | Ile | Leu | Met | Pro | Glu | Lys | Pro | Ile | Ser | Phe | Thr |
| ACA | TTC | AAC | CTC | ATT | CTG | ATG | CCT | GAA | AAG | CCC | ATC | TCC | TTC | ACC |

|  |  |  |  |  |  |  |  | 520 | 521 |
|---|---|---|---|---|---|---|---|---|---|
| Phe | Trp | Pro | Phe | Asn | Gln | Glu | Ala | Thr | Gln | Gln | OP |
| TTC | TGG | CCC | TTT | AAC | CAG | GAA | GCA | ACC | CAG | CAG | TGA | TCAGAGAGGAT |

GGCCTGCAGCCACATGGGAGGAAGGCCCAGGGGTGGGGCCCATGGGGTCTCTGCATCTT

CAGTCGTCTGTCCCAAGTCCTGCTCCTTTCTGCCCAGCCTGCTCAGCAGGTTGAATGGG

TTCTCAGTGGTCACCTTCCTCAGCTCAGCTGGGCCACTCCTCTTCACCCACCCCATGGA

GAC<u>AATAAA</u>CAGCTGAACCATCGAAAAAAAAAAAAAAAAAA

```
Pro Gly Pro Ala Glu Ala Ala Arg Gln Ala Ser Ala Ser Arg Ala Trp Gly Leu Arg Phe Arg Ser Pro Gln Gln Val Leu Pro Ser
CCA GGG CCG GAA GCG GCT GCC CGC CAG GCA TCG GCC CGT GCC TGG GGC CTC CGC TTC CGA AGC CCC CAG CAG GTG CTG CCC TCA
                            300                             310                             320
Pro Asp Gly Arg Arg Ala Ala Gly Val Val Arg Leu Ala Val Thr Arg Leu Asp Glu Ala Thr Arg Ala Val Pro Thr Gly Asp
CCA GAT GCG CGG CGG GCA GCA GGT GTC GTC CGC CTA GCA GTC ACT AGA CTG GAG GCC ACC CGT GCA GTG CCC ACG GGA GAC
         A                  330                             340                             350
Met Glu Asp Leu Pro Cys Gly Leu Val Leu Ser Ser Ile Gly Tyr Lys Arg Pro Val Asp Pro Ser Val Pro Phe Asp Ser Lys Leu
ATG GAA GAC CTC CCT TGT GGG CTG GTG CTC AGC AGC ATT GGG TAT AAG CGC CCT GTC GAC CCA AGC GTG CCC TTT GAC TCC AAG CTT
                            360                             370                             380
Gly Val Ile Pro Asn Val Gly ARg Val Met Asp Val Met Leu Pro Gly Tyr Cys Ser Leu Val Lys Arg Gly Pro Thr Gly Val Ile
GGG GTC ATC CCC AAT GTG GAG GGC CGG GTT ATG GAT GTG ATG CTG CCA GGC TAC TGC AGC CTC GTG AAG AGA GGA CCT ACA GGT GTC ATA
         290                                400                             410
Ala Thr Met Thr Asp Ser Phe Leu Thr Gly Gln Met Leu Leu Leu Gln Lys Ala Gly Leu Leu Pro Ser Gly Arg Pro Gly
GCC ACA ATG ACT GAC AGC TTC CTC ACC GGC CAG ATG CTG CTG CTG CAG AAG GCT GGG TTG CTC CCC TCT GGC AGG CCT GGC
         420                             430                             440
Tyr Ala Ala Ile Gln Ala Leu Ser Ser Arg Gly Val Arg Pro Val Ser Phe Asp Trp Lys Leu Asp Ala Glu Val Ala
TAC GCA GCC ATC CAG GCC CTG AGC AGC CGA GGG GTC CGG CCA GTC TCT TTC GAC TGG GAG AAG CTG GAT GCC GAG GTG GCC
         450                             460                             470
Arg Gly Gln Gly Thr Gly Lys Pro Arg Glu Lys Leu Val Asp Pro Gln Met Leu Arg Leu Leu Gly His OP
CGG GGC CAG GGC ACG GGG AAG CCC AGG GAG CAG AAG CTG GTG GAT CCT CAT GGG GAG ATG CTG CGC CTC CTG GGC CAC TGA
         480                             490                   497

CCAGCAGGGAAGGGATGAGTGTTGGGAGGGAAGGGCTGGCTCCGTCTGAGTGCTCTGCTGATCCGGCCCTGGCTTGGCTGCTCTTCCAGCGTCTC
TCCTCCCTCCTGGGAAGGTCGCCCTTGCGCGCGCAAGGTTTTAGCTTTCAGCAACTGAGGTAACCTTAGGACAGGTGGAGGTGTGGGCCGATCTAACCCCTTACCCATCTCTCTACTGCT
GGACTGTGGAGGGTCACCAGGTTGGGAACATGCTGCACCTGAAATAAACAGCTGCACCCAAAAAAAAAAAAAAAA
                                                               A
```

P450scc

Ad Red

Adx

GAPDH

P450scc

Ad Red

CHOLESTEROL DISPOSAL FUSION ENZYMES

CROSS REFERENCE TO RELATED APPLICATIONS

This application is the National Stage under 35 U.S.C. §371 of PCT/US94/06698 filed Jun. 9, 1994, and is a continuation-in-part of U.S. Ser. No. 08/075,193 filed Jun. 9, 1993, now U.S. Pat. No. 5,547,868.

ACKNOWLEDGEMENTS

This invention was supported in part by NIH grants DK37922, and DK42154. The U.S. Government has rights in this invention as a result of this support.

INTRODUCTION

1. Technical Field

The present invention relates generally to fused proteins and to genetic engineering of enzymes by production of polynucleotides and using them to express fusion proteins.

2. Background

Hypercholesterolemia is a common problem, affecting about 25% of Americans, and causing extensive mortality and morbidity. Therapeutic approaches include cholesterol-lowering drugs such as nicotinic acid or mevinolin, adsorption of dietary cholesterol to orally administered resins such as cholestyramine, and dietary modification to reduce dietary intake. Therapy by reduced dietary intake often requires reduction or elimination of red meat from the diet, as meat is a major dietary source of cholesterol. Cells may either synthesize cholesterol de novo from acetate or they may receive it by receptor-mediated endocytosis of Low Density Lipoprotein (LDL). Both the synthesis of cholesterol and the cellular uptake of LDL are tightly regulated, but, aside from small amounts of cholesterol secreted as bile acids, there is no cholesterol disposal pathway. Most cholesterol produced in animals is involved in the synthesis and maintenance of cell membranes; however, about 400 mg/day in humans is lost as bile salts (Vlahcevic et al 1990). Small amounts of cholesterol (30–50 mg/day) are converted to adrenal and gonadal steroid hormones (Carr and Simpson 1981, Gwynne and Strauss 1982). Steroidogenesis is initiated by converting cholesterol to pregnenolone, which is biologically and hormonally inactive, by the P450 cholesterol side-chain cleavage enzyme, ("P450scc") (for review see Miller 1988). In steroidogenic tissues, such as the adrenals, gonads, and placenta, pregnenolone is rapidly converted to biologically active steroids by other, tissue-specific enzymes (Miller 1988). When radio-labeled pregnenolone is administered intravenously, it is metabolized by the liver to pregnanediol, and pregnanediol and its sulfates and glucuronides, are excreted in the urine and are thus do not become substrates for steroid hormone synthesis (Arcos 1964; Berstein and Solomon 1970). Deficient P450scc activity causes lipoid adrenal hyperplasia, a generally lethal disease.

Cytochromes P450 comprise a large group of heme-containing proteins found in many prokaryotes and in apparently all eukaryotes (Nelson et al 1993). P450 enzymes metabolize exogenous drugs, environmental pollutants and toxins, and also metabolize endogenously produced steroids, vitamin D, bile acids, prostaglandins, biogenic amines, and leukotrienes. All P450 enzymes have about 500 amino acids and function as terminal oxidases in an electron-transport chain from NADPH. Vertebrate cytochrome P450 enzymes fall into two broad groups: the Type I ("mitochondrial") enzymes found in mitochondria, and the more abundant Type II ("microsomal") enzymes found in the endoplasmic reticulum. The Type I and II P450 enzymes differ substantially in their degree of amino acid sequence identity (Nelson et al 1993) and they differ categorically in the fashion in which they receive reducing equivalents from NADPH. Type I (mitochondrial) enzymes receive electrons through two intermediates: the flavoprotein ferredoxin reductase (also called adrenodoxin reductase ("AdRed")) and the iron-sulfur protein ferredoxin (also called adrenodoxin ("Adx"). Type II ("microsomal") enzymes receive electrons through the intermediary of a single flavoprotein, termed P450 oxido-reductase ("OR") (Gonzalez 1989; Yamano et al. 1989). Microsomal P450c17 apparently can receive electrons from either OR or cytochrome $b_5$ (Nakajin et al. 1985). Kumamoto et al. (1989) demonstrated that the N-terminal extension peptide (signal peptide) of bovine mitochondrial P450scc precursor contains sufficient information to target in vitro translated P450scc or adrenodoxin (as an extension peptide-adrenodoxin fusion construct having no P450scc activity) to bovine mitochondria.

Mitochondrial cytochrome P450scc converts cholesterol to pregnenolone by catalyzing three reactions on its single active site: 20α-hydroxylation, 22-hydroxylation, and scission of the C20,22 carbon bond (Lambeth and Pember 1983). Each of these reactions requires a pair of electrons donated by NADPH through protein intermediates. The electrons first pass to AdRed, then to Adx, and finally to P450scc.

Type II fusion enzymes, both naturally occurring and genetically engineered, exhibit first order kinetics rather than standard second order kinetics. P450BM3, a Type II enzyme of *Bacillus megaterium* where the P450 and ferredoxin reductase moieties comprise a single-chain 119 kD protein, is naturally occurring (Nahri and Fulco 1986, 1987; Ruettinger et al 1989). Naturally-occurring Type II fusion enzymes have not been found in eukaryotes. However eukaryotic Type II fusion enzymes, genetically-engineered and expressed in yeast, (Murakami et al 1987, Yabusuki et al 1988, U.S. Pat. No. 5,114,852, Shibata et al 1990, Sakaki et al 1990) yield enzymes with increased activity (Murakami et al 1987; Yabusuki et al 1988; Shibata et al 1990; Sakaki et al 1990).

Until the present invention, there were no known naturally occurring fusion proteins of Type I enzymes. It is not obvious that such a hybrid could function at all. As taught in the art, a single surface of the adrenodoxin molecule interacts with both adrenodoxin reductase and P450scc (Coghlan and Vickery 1991, 1992), which suggests that it is unlikely that Type I enzymes can form a ternary complex during catalysis. Coghlan and Vickery (1991, 1992) showed that the region of adrenodoxin from amino acids 68–86, including aspartic acid residues at 68, 72, 76, 79 and 86 and glutamic acid residues at 73, 74, interacts with both P450scc and adrenodoxin reductase. Of these residues, D72, E73, D76 and D79 appear to be the most important for interaction with P450scc while D76 and D79 are most important for interaction with adrenodoxin reductase. Using succinic anhydride to modify lysine residues in P450scc or P450scc cross-linked with adrenodoxin, Adamovich et al (1989) suggested that eleven lysines in bovine P450scc (residues 73, 109, 110, 126, 145, 148, 154, 267, 270, 338, and 342) were involved in interacting with adrenodoxin. However several of these residues lie in non-conserved regions that have no lysine residues at the corresponding human locus, so that it appears that residues 73, 109, 110, 126, and 148 (and possibly 338 and 342) in the bovine sequence are the most important. The nature and location of the "adrenodoxin docking site" on adrenodoxin reductase remains unknown. In addition the stringency of P450scc in accepting electrons from the mitochondrial electron transfer system was unknown. Furthermore, cytochrome P450scc is an especially slow enzyme, converting about 1 mole of cholesterol per mole of enzyme per second (Morisaki et al 1980).

Cholesterol degradation pathways can also be utilized in fermentation or semisynthetic methods to obtain commercially important steroids from cholesterol. Pregnenolone is now produced from limited supplies of sapogenin and diosgenin isolated from Mexican yams. Pregnenolone, a starting material in the synthesis of many steroids, is also be derived from P450scc degradation of cholesterol. U.S. Pat. No. 4,336,332 discloses the use of pregnenolone in a process for producing pharmacologically valuable 7-alpha-hydroxylated steroids by fermenting or reacting a 7-unsubstituted steroid, such as pregnenolone, with microorganisms of the genus Botryodiplodia or enzyme extracts thereof until hydroxylation occurs. The commercial synthesis of 18-hydroxyprogesterone and 18-hydroxydesoxycorticosterone, previously from plant alkaloids, has been superseded by a sequence starting from pregnenolone. Progesterone, useful to produce numerous gestagens that include hydroxyprogesterone hexanoate, medroxyprogesterone acetate, megestrol acetate, melengestrol acetate, medrogestone, and dihydrogesterone, can be produced via pregnenolone by a 3-betahydroxydehydrogenase and isomerization. Progesterone can be C-11 hydroxylated by Rhizophus nigricans on an industrial scale to yield 11-alpha-hydroxyprogesterone, which can be converted to hydrocortisone and cortisone, which in turn can be converted to corticosterone. Corticosteroids are useful in the treatment of collagen diseases, anaphylaxis, asthma, hay fever, serum sickness, adrenal insufficiency as occurs in Addison's disease, and various skin and eye disorders.

Accordingly, there is a need for improved compositions and techniques for the conversion of cholesterol to other steroidal products and for the degradation of cholesterol in living systems, particularly in the presence of hypercholesterolemia, and in animal-derived food products.

CITED LITERATURE

Adamovitch, T. B., Pikuleva, I. A., Chashchin, V. L., and Usanov, S. A. (1989) *Biophys Acta* 996:247–253.

Akiyoshi-Shibata, M., et al. (1991) *DNA Cel Biol.* 10:613–621.

Arcos, M., Gurpide, E., Vande Wiele, R. L., and Lieberman, S. (1964) *J Clin Endocrinol Metab* 24:237–245.

Argos, P. (1990) *J Mol Biol* 211:943–958.

Baker, K. P., and Schatz, G. (1991) *Nature (London)* 349:205–208.

Berstein, S. and Solomon, S. (1970) *Chemical and Biological Aspects of Steroid Conjugation.* New York, Springer-Verlag Black, S. D. (1992) *FASEB J.* 6:680–685.

Black, S. M., Szklarz, G. D., Harikrishna, J. A., Lin, D., Wolf, C. R., and Miller, W. L. (1993) *Endocrinology* 132:539–545.

Boddupalli, S. S., Oster, T., Estabrook, R. W., and Peterson, J. A. (1992) *J Biol. Chem.* 267:10375–10380.

Brandt, M. E. and Vickery, L. E. (1992) *Arch Biochem Biophys* 294:735–740.

Bredt, D. S., et al., (1991) *Nature* 351:714–718.

Brentano, S. T., Black, S. M., Harikrishna, J., Lin, D., and Miller, W. L. (1992) *Proc Natl Acad Sci USA* 89:4099–4103.

Brentano, S. T. and Miller, W. L. (1992) *Endocrinology* 131:3010–3018.

Brinster RL, Allen JM, Schringer RR, Gelinas RE, Palmiter RD (1988) *Proc. Natl. Acad. Sci. USA* 85:836.

Carr, B. R. and Simpson, E. R. (1981) *Endocr. Rev.* 2:306–326.

Chang, C. -Y., Wu, D. -A., Lai, C. -C., Miller, W. L., and Chung, B. (1988) *DNA* 7:609–615.

Chung, B., Matteson, K. J., Voutilainen, R., Mohandas, T. K., and Miller, W. L. (1986) *Proc. Natl. Acad. Sci. USA* 83:8962–8966.

Chung, B., Picado-Leonard, J., Haniu, M., Bienkowski, M., Hall, P. F., Shivley, J. E., and Miller, W. L. (1987) *Proc. Natl. Acad. Sci. USA* 84:407411.

Clark, B. J., and Waterman, M. R. (1991) *J. Biol. Chem.* 266:5898–5904.

Clark, A. J., et al. (1993) *Philos. Trans. R. Soc. Lond. Biol.* 339:225–232.

Coghlan, V. M. and Vickery, L. E. (1991) *J Biol. Chem.* 266:18606–18612.

Coghlan, V. M. and Vickery, L. E. (1992) *J Biol. Chem.* 267:8932–8935

Cook, R. F. et al. (1993) *Poult. Sci.* 72:554–567.

Cupp, J. R., and Vickery, L. E. (1988) *J. Biol. Chem.* 263:17418–17421.

Edlund, T., Walker, M. D., Barr, P. J., and Rutter, W. J. (1985) *Science* 230:912–916.

Ellis, L., Clauser, E., and Morgan, D. O. (1986) *Cell* 45:721–732.

Gonzalez, F. J. (1989) *Pharmacol. Rev.* 40:243–288.

Gorski K, Carneiro M, Schibler U (1986) *Cell* 47:767.

Graves RA, Tontonoz P, Spiegelman BM (1992) *Mol Cell Biol* 12:1202.

Gwynne, J. T. and Strauss, J. F. III (1982) *Endocr Rev* 3:299–329.

Hall, P. F. (1985) *Rec. Prog. Horn. Res.* 41:1–39.

Hanukoglu, I., and Jefcoate, C. (1980) *J Biol. Chem.* 255:3057–3061.

Hanukoglu, et al., (1987) *Eur. J. Biochem.* 169:449–455.

Hanukoglu, I., and Gutfinger, T. (1989) *Eur. J. Biochem.* 180:479–484.

Hanukoglu, I., Feuchtwanger, R., and Hanukoglu, A. (1990) *J Biol. Chem.* 265:20602–20608.

Hanukoglu, I., Suh, B. S., Himmelhoch, S., and Amsterdam, A. (1990) *J Cell Biol* 111:1373–1381.

Harikrishna, et al. (1993) *DNA Cell Biol.* 12:371–379.

Hartl, F. -U., and Newport, W. (1990) *Science* 247:930–938.

Iida, S., Papadopoulos, V., and Hall, P. F. (1989) *Endocrinology* 124:2619–2624.

Jefcoate, C. R., DiBartolomeis, M. J., Williams, C. A., and McNamara, B. C. (1987) *J. Steroid Biochem.* 27:721–729.

Kumamoto et al. (1989) *J. Biochem.* 105:72–78.

Kimura, T. (1981) *Mol. Cell. Biochem.* 36:105–122.

Lambeth, J. D. and Penber, S. O. (1983) *J Biol. Chem.* 258:5596–5602.

Lambeth, J. D., Seybert, D., and Kamin, H. (1979) *J Biol. Chem.* 254:7255–7264.

Lambeth, J. D., Xu, X. X., and Glover, M. (1987) *J. Biol. Chem.* 262:9181–9188.

Lange, R. and Vacanti, J. P. (1993) *Science* 260:920–926.

Lieberman, S., and Prasad, V. V. K. (1990) *Endocr. Rev.* 11:469.

Lin, D., Gitelman, S. E., Saenger, P., and Miller, W. L. (1991) *J. Clin. Invest.* 88:1955–1962.

Lin, D., Shi, Y., and Miller, W. L. (1990) *Proc. Natl. Acad. Sci. USA* 87:8516–8520.

Lin. D., Harikrishna, J. A., Moore, C. C. D., Jones, K. L., and Miller, W. L. (1991) *J. Biol. Chem* 266:15992–15998.

Lin, D., Black, S. M., Nagahama, Y., and Miller, W. L. (1993) *Endocrinology* 132:2498–2506.

Long, R. M., et al. (1992) "Atherogenesis in transgenic mice expressing humor apolipoprotein (a)" *Nature* 360:670–672.

Miller, W. L. (1988) *Endocr Rev* 9:295–318.

Monier, S., Van Luc, P., Kreibich, G., Sabatini, P. D., and Adesnik, M. (1988) *J. Cell. Biol.* 107:457–470.

Morisaki, M., Duque, C., Ikekawa, N., and Shikita, M. (1980) *J Steroid Biochem* 13:545–550.

Morohashi, K., Fujii-Kuriyama, Y., Okada, Y., Sogawa, K., Hirose, T., Inayama, S., and Omura, T. (1984) *Proc. Natl. Acad. Sci. USA* 81:4647–4651.

Morohashi, K., Sogawa, K., Omura, T., and Fujii-Kuriyama, Y. (1987) *J Biochem* 29:879–887.

Murukami, H., Yabusaki, Y., Sakaki, T,. Shibata, M., and Ohkawa, H. (1987) *DNA* 6:189–197.

Nakajin, S., Takahashi, M., Shinoda, M., and Hall, P. F. (1985) *Biochem. Biophys. Res. Commun.* 132:708–713.

Narhi, L. O., and Fulco, A. J. (1986) *J Biol. Chem.* 261:7160–7169.

Narhi, L. O. and Fulco, A. J. (1987) *J Biol. Chem.* 262:6683–6690.

Nelson, D. R., Kamataki, T., Waxman, D. J., Guengerich, F. P., Estabrook, R. W., Feyereisen, R., Gonzalez, F. J., Coon, M. J., Gunsalus, I. C., Gotoh, O., Okuda, K., and Nebert, D. W. (1993) *DNA Cell Biol* 12:1–51.

Okamura, et al., (1985) *PNAS* 82:5705–5709.

Omdahl, J. L., et al. (1992) *Arch. Biochem. Biophys.* 293:213–218.

Picado-Leonard, J., Voutilainen, R., Kao, L. -C., Chung, B., Strauss III, J. P., and Miller, W. L. (1988). *J Biol. Chem.* 263:3240–3244; corrected 11016.

Porter, T. D., and Kasper, C. B. (1985) *Proc. Natl. Acad. Sci. USA* 82:973–977.

Pursel, V. G. et al. (1990) *J. Reprod. Fertil. Suppl.* 41:77–87.

Plump, A. S., et al. (1992) "Severe hypercholesterolemia and atherosclerosis in apolipoprotein E-deficient mice created by homologous recombination in ES cells," *Cell* 71:343–353.

Rossant, J. et al. (1993) *Philos. Trans. R. Soc. Lond. Biol.* 339:207–215.

Rubin EM, Ishida BY, Clift SM, Krauss RM (1991) *Proc Natl Acad Sci USA* 88:434.

Rubin EM, Krauss RM, Spangler EA, Verstuyft JG, Clift SM (1991) *Nature* 353:265.

Ruetfinger, R. T., Wen, L. -P., and Fulco, A. J. (1989) *J Biol. Chem.* 264:10987–10995.

Sagara, Y., et al. (1987) *J. Biochem.* 102:1333–1336 with published errata at (1989) *J. Biochem.* 106:539 and (1990) *J. Biochem.* 108:1070.

Sakaki, T., Shibata, M., Yabusaki, Y., Murakami, H., and Ohkawa, H. (1990) *DNA Cell Biol* 9:603–614.

Santoro IM, Yi TM, Walsh K (1991) *Mol Cell Biol* 11:1944.

Shibata, M., Sakaki, T., Yabusaki, Y., Murakami, H., and Ohkawa, H. (1990) *DNA Cell Biol* 9:27–36.

Simpson, E. R. (1979) *Mol. Cell. Endocrinol.* 13:213–227.

Solish, S. B., Picado-leonard, J., Morel, Y., Kuhn, R. W., Mohandas, T. K.,

Hanukoglu, I., and Miller, W. L. (1988). *Proc Natl Acad Sci USA* 85:7104–7108.

Sparkes, R. S., Klisak, I., and Miller, W. L. (1991) *DNA Cell Biol* 10:359–365.

Tokunaga, K., Nakamura, Y., Sakata, K., Fujimori, K., Ohkubo, M., Sawada, K., and Sakiyama, S. (1987) *Cancer Res* 47:5616–5619.

Takahashi, M., et al. (1993) "Rainbow trout ovarian cholesterol side chain cleavgae cytochrome P450 (P450scc): CDNA cloning and MRNA expression during oogenesis," *FEBS Letters* 319:4548.

Vick, L. et al. (1993) *Philos. Trans. R. Soc. Lond. Biol.* 251:179–182.

Vlahcevic, Z. R., Heuman, D. M., and Hylemon, B. (1990) *Hepatology—A Textbook of Liver Disease, 2nd Edition* D. Zakim and T. D. Boyer, Eds. W. B. Saunders, Philadelphia pp 341–377.

Wada, A., et al. (1991) *Arch. Biochem. Biophys.* 290:376–380.

Walsh, K. (1989) *Mol Cell Biol* 9:2191.

Wickner, W. T., and Lodish, H. F. (1985) *Science* 23:400407.

Yabusaki, Y., Murakami, H., Sakaki, T., Shibata, M., and Ohkawa, H. (1988) *DNA* 7:701–711.

Yamano, S., Aoyama, T., McBride, O. W., Hardwick, J. P., Gelboin, H. V., and

Gonzalez, F. J. (1989) *Mol. Pharmacol.* 35:83–88.

Yokode M, Hammer RE, Ishibashi S, Brown MS, Goldstein JL (1990) *Science* 250:1273.

Zuber, M. X., Mason J. I., Simpson, E. R., and Waterman, M. R. (1988) *Proc Natl Acad Sci USA* 85:699–703.

SUMMARY OF THE INVENTION

Polynucleotide constructs encoding fusion enzymes of a P450scc enzyme and at least one electron transfer-protein, such as fusion of P450scc, Adx, and AdRed or of P450scc and OR, are provided for synthesis of fusion enzymes capable of cholesterol disposal. The fusion enzymes can be used advantageously in the production of steroids from cholesterol. Both the polynucleotide constructs and the fusion enzymes themselves also find use in the therapy of atherosclerosis and other disorders in which a reduction in cholesterol level is desired, as well as in the disposal of cholesterol from meat products. At least one of the enzyme fusions, $H_3N$-P450scc-AdRed-Adx-COOH, is about five-fold faster than the natural three component system in converting cholesterol to pregnenolone.

BRIEF DESCRIPTION OF THE DRAWINGS

Numerous aspects and advantages of the invention will be apparent to those skilled in art in light of the following detailed description of specific embodiments when considered together with the drawings that form a part of this specification, wherein:

FIG. 1 shows the sequence of human P450scc cDNA (SEQ ID NO: 1) and the corresponding deduced amino acid sequence (SEQ ID NO: 2). The amino acid positions are numbered beginning with the methionine initiation codon.

FIG. 2 shows the sequence of human adrenodoxin reductase ("AdRed") cDNA (SEQ ID NO: 3) and the corresponding deduced amino acid sequence (SEQ ID NO: 4). The amino acid positions are numbered beginning with the methionine initiation codon. The downward arrow between amino acids 32 and 33 indicates the cleavage site resulting in removal of the mitochondrial signal peptide. The brackets [] delineate amino acids 204 to 209 that are found in an inactive form of AdRed arising from alternate mRNA splicing and not in the active form used in the instant invention.

FIG. 3 shows the sequence of human adrenodoxin ("Adx") cDNA (SEQ ID NO: 5) and the corresponding deduced amino acid sequence (SEQ ID NO: 6). The amino acid positions are numbered beginning with the methionine initiation codon. The cleavage sites that yield mature adrenodoxin from the prepro-protein are between amino acids 56 and 57 and between amino acids 170 and 171.

FIG. 6A depicts a time course of pregnenolone production. Incubations with 5 $\mu$M 22-hydroxycholesterol were for the times shown, followed by immunoassay of pregnenolone. The data are from three independent transfections, each done with different plasmid preparations and measured in triplicate. Pregnenolone values in ng/ml of culture medium are shown ±SEM and are normalized for transfection efficiency as determined by co-transfection with RSV-$\beta$-gal. FIG. 6B depicts a Lineweaver-Burke analysis. Cells triply transfected with equimolar amounts of vectors expressing P450scc, Adx, and AdRed (diamonds, upper line) or transfected with an equimolar amount of vector expressing F2 (squares, lower line) were incubated with 0.5 to 5.0 $\mu$M 22R-hydroxycholesterol. Data are averaged from three individual transfections, each done with different plasmid preps and assayed in triplicate.

FIG. 7D) as a control for RNA loading.

FIG. 12A depicts a Western blot of P450c17. Fifty µg samples of protein from COS-1 cells transfected with vector (pECE) or from cells transfected with vectors expressing either P450c17 wild type (c17WT) or P450c17 with a P450IIB1 leader peptide (2B-c17) were displayed and analyzed with rabbit anti-human P450c17. FIG. 12B shows the enzymatic activity of the cells shown in FIG. 12A. Before the cells were harvested, they were incubated with [$^{14}$C] progesterone ("PROG") for 2 h and the production [$^{14}$C] 17α-hydroxyprogesterone ("17OHP") was assayed by thin layer chromatography of the culture medium.

DESCRIPTION OF SPECIFIC EMBODIMENTS

Figure 4:
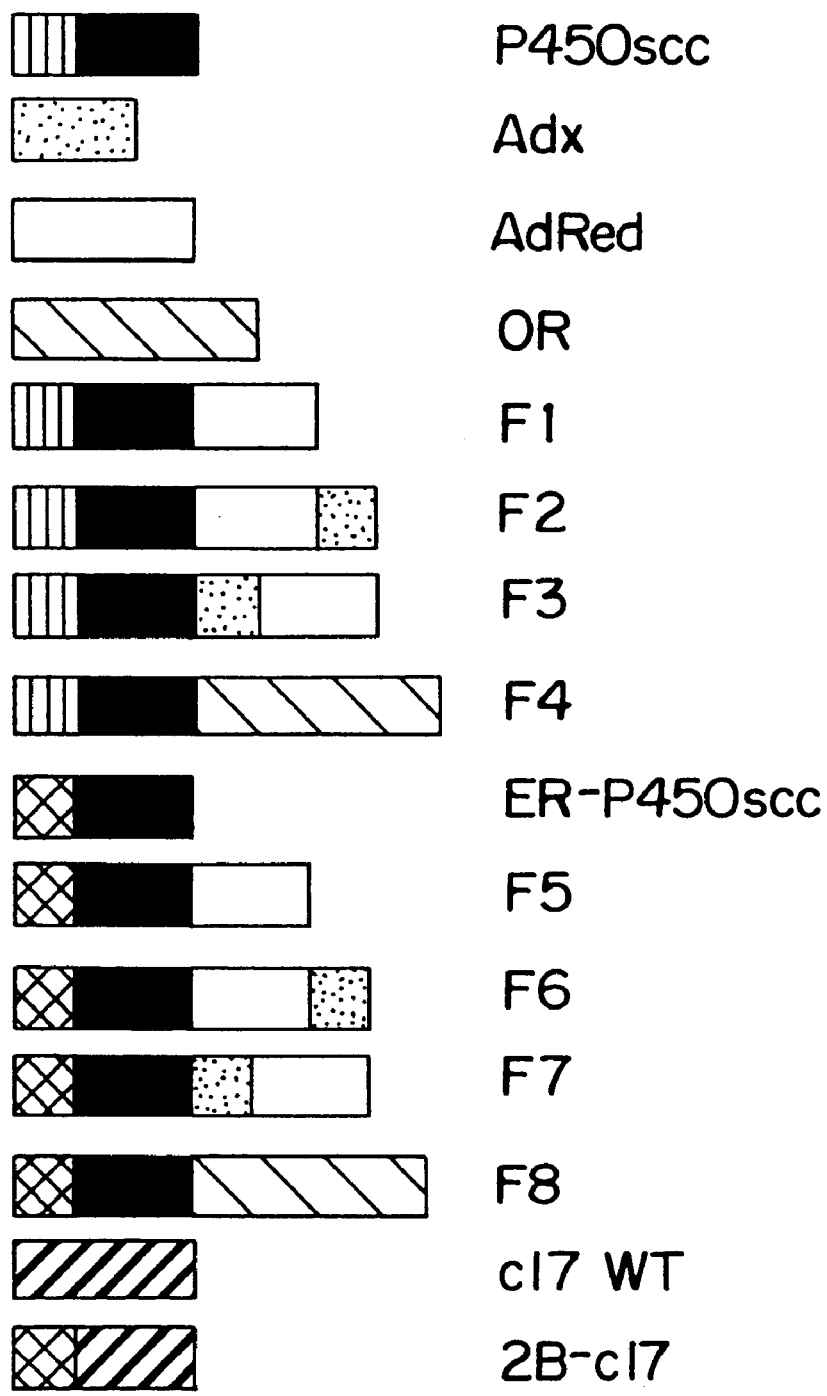
FIG. 4 is a schematic demonstrating the polynucleotide DNA constructions used in this study. Leader sequences at the amino-terminus (5' end, left) are the 39-amino-acid mitochondrial leader sequence of human P450scc (vertical lines), or the 23-amino-acid microsomal (endoplasmic reticulum) leader sequence of rat P450IIB1 (checked boxes). Mature-protein coding regions follow the leader sequences: black box, P450scc; grey box, adrenodoxin ("Adx"); white box, adrenodoxin reductase ("Ad Red"); wavy striped box, P450 oxidoreductase ("OR"). The vertical bar(s) in the F1AR+, F2AR+ and F2DM constructions indicate the presence of the extra sequences in the 18+ form of AdRed or the 3 mutated Cys residues in Adx. The c17WT construction expresses the wild-type human P450c17 protein (diagonal lines), and 2B-c17 has the same P450IIHB1 microsomal leader sequence used in ER-P450scc and F5–8. Also shown in this diagram are the constructions expressing wild-type human adrenodoxin and adrenodoxin reductase, which use their own endogenous mitochondrial leader sequences (Brentano and Miller 1992), and the construction expressing human P450 oxidoreductase (Lin et al. 1993), which uses its own endogenous microsomal leader sequence.

The present invention is directed to a fusion enzyme comprising P450scc and at least one electron-transfer protein. "Fusion enzyme" here and elsewhere in this specification refers to a single polypeptide chain containing two or more sequences of amino acids that are found in the indicated single protein sources (here P450scc and the electron-transfer protein or proteins). Each of the sequences is capable of functioning in the same manner as the original protein (e.g., can still function to transfer electrons) although the properties as expressed mathematically (e.g., rate of electron transfer) can vary from that of the original molecule. In cases where the function is diminished it differs preferably by less than 10-fold, more preferably by less than 2-fold, most preferable by less than 25%. In at least some cases, as discussed below, desirable properties such as overall reaction rate are enhanced for the fusion protein relative to the individual proteins acting separately.

The particular electron transfer protein (or proteins) coupled with P450scc to form the fused enzyme is not limited other than in its ability to transfer electrons to P450scc. In preferred embodiments, electron-transfer proteins are selected from the group consisting of adrenodoxin reductase, adrenodoxin, P450 oxidoreductase, and cytochrome b5, whether these materials are from human or other sources. One embodiment of this type is F4 in which the electron transfer protein is P450 oxidoreductase. The electron transfer protein can utilize a separate electron transfer protein that is not part of the fusion protein. A specific embodiment of this type is example below F1 which contains adrenodoxin reductase that can use endogenous adrenodoxin as an intermediate electron transfer protein. A second embodiment of this type is F9, fusion H$_2$N-P450scc-Adx-COOH, which is the same as F3 but without the adrenodoxin reductase sequence. Enzymes or domains of enzymes having electron-transfer function, such as a reductase domain of nitric oxide synthetase (Bredt 1991), are candidates for providing the electron-transfer function of the instant fusion enzymes. Preferred are fusion enzymes containing adrenodoxin reductase wherein adrenodoxin reductase has at least 90% sequence identity with the sequence of human adrenodoxin reductase (SEQ ID NO: 3) from amino acids 33 to 497, excluding amino acids 204 to 209, set forth in FIG. 2 (or with another such listing of known compounds having adrenodoxin reductase activity from a different species, such as bovine, porcine, or fish, e.g. trout (Takahashi 1993)). Particularly preferred are fusion enzymes containing adrenodoxin reductase wherein adrenodoxin reductase has the sequence of human adrenodoxin reductase (SEQ ID NO: 3) from amino acids 33 to 497, excluding amino acids 204 to 209, set forth in FIG. 2. Specific examples of preferred embodiments of this type include fusions selected from the group consisting of F1, F2, and F3 from the following examples. In alternative preferred embodiments adrenodoxin reductase has a corresponding bovine adrenodoxin reductase sequence provided by Hanukoglu and Gutfinger (1989) or Sagara et al (1987). Fragments of these specific sequences that retain electron-transfer activity are also preferred. In other embodiments the AdRed sequence is provided as the 18+ form sequence (Solish et al. 1988; Lin etal. 1990), such as in F1AR+ or F2AR+.

In the fusion enzyme it is preferred that P450scc has at least 90% sequence identity with the amino acid sequence 40 to 521 of human P450scc (SEQ ID NO: 1) set forth in FIG. 1 (or with another such listing of known compounds having P450scc activity from a different species, such as bovine or porcine) and has cholesterol side chain cleaving activity. In a specific preferred embodiment, the P450scc enzyme has the same sequence of human P450scc (SEQ ID NO: 1) from amino acid 40 to 521 set forth in FIG. 1. In another preferred embodiment the P450scc enzyme has a corresponding bovine sequence provided by Morohashi et al. (1984). Fragments of these specific sequences that retain the side chain cleavage activity of P450scc are also preferred.

Figure 3:
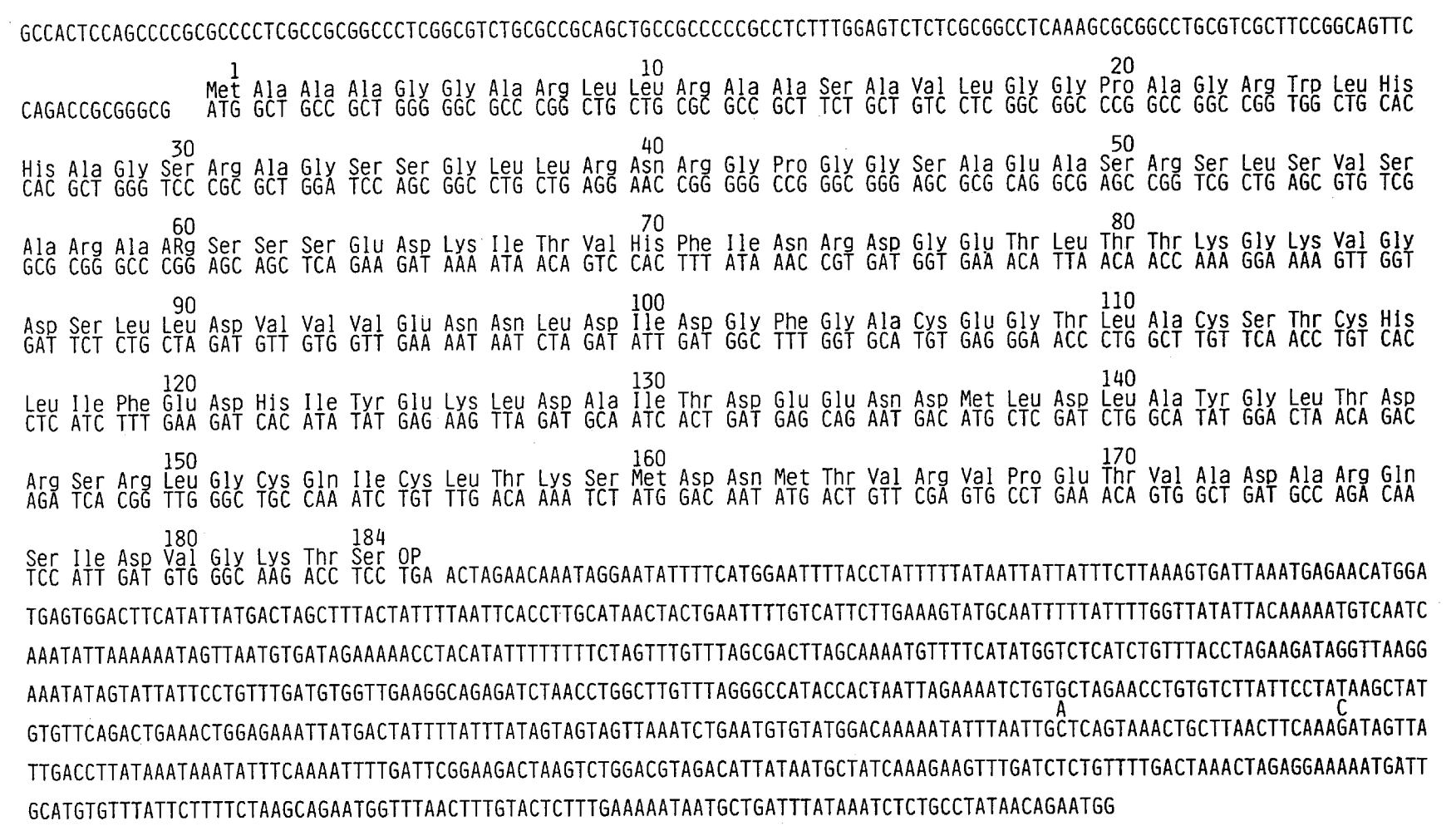

Fusion enzymes are preferred which comprise, in addition to P450scc and adrenodoxin reductase, a third amino acid sequence that encodes adrenodoxin or a fragment of an adrenodoxin molecule retaining the ability to transfer electrons from adrenodoxin reductase to P450scc (called here "adrenodoxin electron-transfer activity"). Fusion enzymes are preferred when the single polypeptide chain has adrenodoxin electron-transfer activity and the adrenodoxin-electron-transfer activity encoding sequence has at least 90% sequence identity with amino acids 57 to 170 set forth in FIG. 3 (SEQ ID NO: 5) (or with another such listing of known compounds having P450scc activity from a different species, such as bovine or porcine). In alternative preferred embodiments, the adrenodoxin sequence is obtained from a bovine adrenodoxin sequence set forth in Okamura et al. (1985) or a porcine renodoxin sequence set forth by Omdahl et al. (1992). In the most preferred embodiments the adrenodoxin portion of the fusion enzyme has the same sequence of human adrenodoxin (SEQ ID NO: 5) from amino acid 57 to 170 set forth in FIG. 3 or is a functional fragment of that sequence. Specific preferred embodiments of this tripartite peptide comprise fusions F2 and F3 from the following examples.

When forming a fusion enzyme of the invention, the amino acid segments that correspond to segments (or entire molecules) of the active species forming the enzyme complex can be attached directly to each other, or they can be attached to each other by organic or biochemical linkers. Preferred linkers are short peptides that link P450scc to the electron-transfer protein. These short peptides are not restricted in their sequences, although it is preferred that the linkers be flexible (rather than forming rigid alpha helix segments) and that they have a length of from 1 to 50 alpha-amino acids, preferably 2 to 25, more preferably 3 to 10 and most preferably 4 to 7. Preferred linkers are those having an extended structure, contain small (glycine) and polar (serine or threonine) residues which impart flexibility yet maintain conformation in solution, generally lack large and bulky hydrophobic amino acids and contain amino acids most preferred by natural linkers. Proline may be included in linker sequences. Argos (1990) discloses additional preferred linkers suitable for carrying out the invention. Examples of linking peptides are Thr-Asp-Gly-Thr-Ser (SEQ ID NO: 9) or Thr-Asp-Gly-Ala-Ser (SEQ ID NO: 10). Examples of useful fusion enzymes utilizing linkers are those in which at least one linking peptide links P450scc to adrenodoxin, P450scc to adrenodoxin reductase, or adrenodoxin to adrenodoxin reductase.

Linker amino acid sequences and consequently the nucleic acid sequences encoding them are optionally designed to also introduce one or more unique restriction enzyme sites not found in the enzyme-encoding regions. Such polynucleotide enzyme-encoding sequences with flanking restriction sites are easily manipulatable modules that provide the advantage of allowing rapid construction of additional fusion enzyme-encoding polynucleotides by insertion, deletion or rearrangement of the same, new or modified enzyme-encoding modules to rapidly screen for active fusions. Design and use of such linkers and the manipulation of resulting DNA modules are provided in the examples.

The order in which the various active segments are attached to each other is not critical if one is interested in obtaining minimal activity, but the order of fusions can affect activity of the complex, as shown in the detailed examples below. Tripartite enzymes in which P450scc is at the N-terminal end are one class of fusion enzymes that are preferred, as are those in which adrenodoxin is at the C-terminal end.

Since the complex will be prepared in assembled form, signal peptide sequences are normally absent. However, their inclusion will not adversely affect enzyme activity, and a signal peptide, either naturally- or nonnaturally-occurring, can be included at the N-terminus (or elsewhere in the usual manner) to direct expression of the entire complex and transportation to the desired location, such as preferably to the mitochondria of a cell. Specific embodiments of the invention F5 through F8 contain a targeting peptide that directs the fusion protein to the endoplasmic reticulum. Although enhanced levels of pregnenolone synthesis were not detected in the environment under which these fusion were employed, it is expected that activity would be observed for these fusions in a different environment, such as a reconstituted production system. An example of a fusion enzyme with a missing signal sequence is one in which at least the P450 oxidoreductase N-terminal amino acids that direct association of P450 oxidoreductase to the endoplasmic reticulum membrane are absent, preferably at least the 56 N-terminal amino acids of human P450 oxidoreductase as in fusion F4. The mitochondria signal peptide of yeast cytochrome c oxidase subunit IV is preferred for targeting fusion enzymes to yeast mitochondria. The absence of a signal peptide results in cytosolic expression. See for example Akiyoshi-Shibata et al. 1991.

In addition to the fusion enzymes themselves, the present invention also encompasses polynucleotide sequences encoding the fusion enzymes, including all of the embodiments described above such as fusion enzymes containing linkers, those attached in different orders of active segments, and those with heterologous signal sequences.

In preferred embodiments a polynucleotide sequence encoding P450scc has at least 90% sequence identity with the sequence encoding amino acids 40 to 521 of human P450scc (SEQ ID NO: 1) set forth in FIG. 1 and encodes a polypeptide having P450 side chain cleaving activity. Even more preferred are polynucleotide sequences in which a P450scc polypeptide segment is encoded by the sequence of human P450scc DNA (SEQ ID NO: 1) set forth in FIG. 1. Other preferred embodiments are those in which an adrenodoxin reductase (SEQ ID NO: 3) amino acid segment is encoded by the DNA sequence of human adrenodoxin reductase excluding the sequence encoding amino acids 204 to 209 set forth in FIG. 2. Other preferred polynucleotide constructs are those in which a sequence encoding adrenodoxin has at least 90% sequence (SEQ ID NO: 5) identity with the sequence encoding amino acids 57 to 170 set forth in FIG. 3 and encodes a polypeptide having adrenodoxin electron-transfer activity, especially one in which the sequence encoding adrenodoxin is identical to the sequence encoding human adrenodoxin (SEQ ID NO: 5) from amino acid 57 to 170 set forth in FIG. 3.

In some cases directed expression of a fusion enzyme will be desired, such as when one intends to direct expression of the fusion enzyme to a particular tissue or even cell organelle. In such cases appropriate signal sequences should be encoded by the polynucleotide such as when the polynucleotide further encodes a signal peptide fused to the N-terminal of the fusion enzyme. A preferred signal sequence is one which directs transport of the fusion enzyme to mitochondria. Examples of plasmids that have been constructed in accordance with this aspect of the invention are shown in the examples as F1, F2, F3, F4, F1AR+, and F2AR+. Embodiments F5, F6, F7, and F8 contain a signal peptide that direct the expressed fusion protein to the endoplasmic reticulum.

As will be understood by those of ordinary skill in the art of protein expression from nucleotide sequences, a functional polynucleotide construct capable of expressing the fusion enzyme of the invention will generally comprise (a) a transcription initiation region functional in a host (unicellular or other) organism, (b) a polynucleotide sequence encoding the fusion enzyme, and (c) a transcription termination region. Such constructs are exemplified by plasmids F1, F2, F3, F4, F5, F6, F7, F8, F1AR+, and F2AR+ in the following examples. When intended for expression in a eukaryotic cell, the functional polynucleotide sequence can be interrupted by one or more intron.

In addition minor variations of the previously mentioned peptides and DNA molecules are also contemplated as being equivalent to those peptides and DNA molecules that are set forth in more detail, as will be appreciated by those skilled in the art. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the biological activity of the resulting molecule, especially if the replacement does not involve an amino acid at an active site or a binding site. Whether a change results in a functioning peptide is readily determined by incubating the resulting peptide in a solution comprising cholesterol, co-factors, and the supplementary P450scc, flavoprotein, and/or iron-sulfur protein and monitoring the appearance of pregnenolone. If pregnenolone is detected, the replacement is immaterial, and the molecule being tested is equivalent to those of the Figures, although the rate may vary from that of the specific peptide shown. Peptides in which more than one replacement has taken place are readily tested in the same manner. Suitable reconstitution assays useful for testing are described, for example, by Palin et al. (1992) and Kuwada et al. (1991). Alternatively, the modifications are tested by modifying a DNA construct of the invention by well known recombinant DNA techniques such that upon expression in a host cell, the resulting fusion protein contains the desired modification, and is assayed as taught in the Examples.

DNA molecules that code for such peptides can readily be determined from a list of equivalent codons and are likewise contemplated as being equivalent to the DNA sequences of the Figures. In fact, since there is a fixed relationship between DNA codons and amino acids in a peptide, any discussion in this application of a replacement or other change in a peptide is equally applicable to the corresponding DNA sequence or to the DNA molecule, recombinant vector, or transformed microorganism in which the sequence is located (and vice versa).

In addition to the specific nucleotides in the expressed portion of the sequences identified in the Figures, DNA (or corresponding RNA) molecules of the invention can have additional nucleotides preceding or following the coding region other than those that are specifically listed. For example, poly A can be added to the 3'-terminal, short (e.g., fewer than 20 nucleotides) sequence can be added to either terminal to provide a terminal sequence corresponding to a restriction endonuclease site, stop codons can follow the peptide sequence to terminate transcription, and the like. Additionally, DNA molecules containing a promoter or enhancer region or other control region upstream from the gene can be produced.

In addition to the constructs themselves, the invention also encompasses a procaryotic or eukaryotic host cell comprising a polynucleotide construct of the invention, such as a mammalian host cell, particularly a COS or CHO cell. The host cell may be steroidogenic or non-steroidogenic depending on the particular use. Non-steroidogenic host cells are preferred for use in production of pregnenolone or for production of a transgenic animal. A preferred mammalian host cell is one in which the host cell is a precursor to a transgenic animal (especially bovine). The invention thus encompasses non-human transgenic organisms comprising a polynucleotide construct of the invention. Preferred non-human transgenic organisms include those in which the transcription initiation region of the polynucleotide construct is expressible in adipocyte-specific or liver-specific fashion, being even more preferred when the transgenic organism is a livestock animal used for meat production. However, reduction of cholesterol levels in such animals need not be accomplished by producing a transgenic animal; instead, the fusion enzyme of the invention can be administered directly to the animal. Yeast, bacteria, such as *E. coli*, and mycobacterium expressing fusion enzymes of the invention are examples of alternative non-mammalian host cell embodiments.

Expression of a fusion enzyme of the invention can be enhanced by including multiple copies of the fusion gene in a transformed host, by selecting a vector known to reproduce in the host or by using techniques and vectors that yield multiple genome-integrated copies, thereby producing large quantities of protein from exogenous inserted DNA (such as pUC8, ptac12, or pIN-III-ompA1, 2, or 3), or by any other known means of enhancing peptide expression.

In all cases, fusion enzymes will be expressed when the DNA sequence is functionally inserted into the vector. By "functionally inserted" is meant in proper reading frame and orientation, as is well understood by those skilled in the art. Typically, a fusion enzyme gene will be inserted downstream from a promoter and will be followed by a stop codon, although production as a secreted hybrid protein comprised of the fusion protein and a targeting or tag sequence, optionally followed by cleavage of the targeting or tag sequence, may be used if desired.

In addition to the above general procedures which can be used for preparing recombinant DNA molecules and transformed unicellular and multicellular organisms in accordance with the practices of this invention, other known techniques and modifications thereof can be used in carrying out the practice of the invention. In particular, techniques relating to genetic engineering have recently undergone explosive growth and development. Many recent U.S. patents disclose plasmids, genetically engineering microorganisms, and methods of conducting genetic engineering which can be used in the practice of the present invention. For example, U.S. Pat. No. 4,273,875 discloses a plasmid and a process of isolating the same. U.S. Pat. No. 4,304,863 discloses a process for producing bacteria by genetic engineering in which a hybrid plasmid is constructed and used to transform a bacterial host. U.S. Pat. No. 5,240,831 discloses vectors and methods for genetic expression of biologically active eukaryotic cytochrome P450 17α-hydroxylase in bacteria. U.S. Pat. No. 4,419,450 discloses a plasmid useful as a cloning vehicle in recombinant DNA work. U.S. Pat. No. 4,362,867 discloses recombinant cDNA construction methods and hybrid nucleotides produced thereby which are useful in cloning processes. U.S. Pat. No. 4,403,036 discloses genetic reagents for generating plasmids containing multiple copies of DNA segments. U.S. Pat. No. 4,363,877 discloses recombinant DNA transfer vectors. U.S. Pat. No. 4,356,270 discloses a recombinant DNA cloning vehicle and is a particularly useful disclosure for those with limited experience in the area of genetic engineering since it defines many of the terms used in genetic engineering and the basic processes used therein. U.S. Pat. No. 4,336,336 discloses a fused gene and a method of making the same. U.S. Pat. No. 4,349,629 discloses plasmid vectors and the production and use thereof. U.S. Pat. No. 4,332,901 discloses a cloning vector useful in recombinant DNA. U.S. Pat. No. 5,164,313 discloses use of a vaccinia virus vector for gene expression. Although some of these patents are directed to the production of a particular gene product that is not within the scope of the present invention, the procedures described therein can easily be modified to the practice of the invention described in this specification by those skilled in the art of genetic engineering.

Administration of the fusion enzyme to an animal can occur for a variety of reasons but is typically used to reduce cholesterol levels, including treatment of clinical conditions such as hypercholesterolemia. When so administered to humans, administration is typically in the form of a pharmaceutical composition comprising a fusion enzyme and a pharmaceutically acceptable carrier. The fusion protein used in such a process can be produced by growing a host organism, typically a unicellular organism, containing a polynucleotide construct of the invention under conditions wherein the fusion enzyme is expressed by the host, and then isolating the expressed fusion enzyme.

When peptides of the invention are utilized in the treatment of disorders in which a patient is being treated to reduce an in vivo cholesterol concentration, a functional fusion enzyme is administered to the patient in an amount effective to reduce the concentration to desired levels. The term concentration here is used in its broadest sense to include deposits of cholesterol that have formed on arterial walls and in other in vivo interior spaces. Reduction of elevated serum cholesterol levels is also a goal of the present invention.

Administration can be by any means in which peptides are administered to the location in which a reduction in cholesterol concentration is desired. Since reductions in blood concentrations are particularly important, intravenous injection is a preferred method of administration. However, other techniques that will result in introduction of an effective amount of a fusion enzyme to the desired location can be utilized. Examples include intramuscular and subcutaneous injections. Because of enzymatic degradation in the stomach and small intestine, oral administration is less desirable although oral administration may be useful in case of high oral intake of cholesterol by acting to degrade cholesterol before it is absorbed and before the fusion enzyme itself is degraded. Recent advances in preparing compositions containing proteins for oral ingestion, typically developed for oral administration of insulin, can be utilized.

Alternative routes of administration of the peptides of the invention are gene transfer into a patient's somatic cells and tissue engineering wherein cells expressing the peptides of the invention are introduced into a patient, for example as a graft, a tissue or organ replacement or as part of a cell transplant device. Langer and Vacanti (1993) provide a review of recent techniques of tissue engineering.

When a fusion enzyme of the invention is administered by itself, its activity can depend on the presence of endogenous amounts of the remainder of the electron transport system. For example, fusion $H_2N$-P450scc-AdRed-COOH requires adrenodoxin. Therefore, the invention is also carried out by administering a fusion enzyme concurrently with an exogenous supplementary protein. One useful way to administer a fusion enzyme, particularly with a supplementary protein, is in the form of liposomes.

The effective amount to be administered will vary from patient to patient depending on the amount of endogenous enzyme activity that is present and the degree to which cholesterol levels are high and in need of reduction. Accordingly, effective amounts are best determined by the physician administering the fusion enzyme. However, a useful initial amount for administration is in the range of from 0.1 to 100 mg, preferably from 1 to 10 mg for a 70-kg adult. After allowing sufficient time for the fusion enzyme to take effect (typically 24 hours), analysis of the current cholesterol level and comparison to the initial level prior to administration will determine whether the amount being administered is too low, within the right range, or too high. It has been demonstrated that reduction of serum cholesterol levels even to levels higher than those considered normal for the age and sex of the patient being treated result in an increased lifespan for a patient so treated. Reduction of serum cholesterol to normal levels is even more advantageous.

A particularly preferred use for the fusion enzymes of the invention is in the conversion of cholesterol to pregnenolone for use in the semi-synthetic production of steroids. Fermentation methods utilizing transformed or transfected cells or those from a transgenic animal of the invention are preferred. In one embodiment, host cells of the invention can be treated with inhibitors of enzymes of cholesterol degradation pathways (steroid synthesis and degradation pathways) to cause accumulation of a desired intermediate or product either within the cell or culture medium. In another embodiment, fermentation methods use mutants of host cells of the invention that are defective in a particular step in cholesterol degradation or steroid synthesis such that accumulation of desired products occurs. Such mutants can be obtained starting with fusion-expressing host cells of the invention using known mutagenesis techniques, and preferably, recombinant DNA gene ablation techniques. Alternatively, enzyme extracts, containing fusion proteins of the invention, are obtained from the transformed, transfected, or transgenic host cells of the invention and are used to produce steroids. In one embodiment reconstitution systems, such as those described by Palin et al. 1992, Kuwada et al. 1991, Akiyoshi-Shibata et al. 1991 and Wada et al 1991, are useful for the production of pregnenolone from cholesterol or P450scc substrates.

Pregnenolone, obtained using P450scc-fusion enzymes or host cells expressing same, is a precursor in the synthesis of many important biologically active steroids. For example, U.S. Pat. No. 4,336,332 (1982) discloses the use of pregnenolone in a process for producing pharmacologically valuable 7-alpha-hydroxylated steroids comprising fermenting or reacting a 7-unsubstituted steroid, such as pregnenolone, with microorganisms of the genus Botryodiplodia or enzyme extracts thereof until hydroxylation occurs. 18-hydroxyprogesterone and 18-hydroxydesoxycorticosterone are synthesized starting from pregnenolone. U.S. Pat. No. 3,856,780 discloses the synthesis from pregnenolone of 25-hydroxycholesterol, which is an important intermediate in the synthesis of 25-hydroxycholecalciferol. Allopregnanedione, which can be used in the synthesis of progesterone (FR 845,034), can be prepared by hydrogenation of pregnenolone (Pappas and Nace, 1959 *J. Am. Chem. Soc.* 81:4556). 3,20-Testosterone is isolated in minute amounts from testes, especially bull testes (David et al., *Z. Physiol. Chem.* 233, 281 (1935)) and biosynthetically from pregnenolone. Allopregnan-3β-ol-20-one can be obtained from steroid precursors such as pregnenolone (Mancera et al., 1951 *J. Org. Chem.* 16:192; Pappas and Nace, 1959 *J. Am. Chem. Soc.* 81:4556). Pregnenolone is an intermediate in the biosynthesis of progesterone, in which pregnenolone is converted by a 3-beta-hydroxydehydrogenase and isomerase to progesterone. Progesterone, in turn leads to the production of additional important steroids. C-17 hydroxylation of progesterone by an enzyme in the microsomes of the adrenals, ovaries, or testes yields 17-hydroxyprogesterone. This is hydroxylated at C-21 in adrenal microsomes to yield 11-desoxycortisol, which is hydroxylated to hydrocortisone by an 11-beta-hydroxylase in adrenal mitochondria. Hydrocortisone can be oxidized to cortisone. Corticosterone is biosynthesized in a manner similar to cortisone from progesterone via 11- and 21-hydroxylation. From progesterone numerous gestagens can be derived that include hydroxyprogesterone hexanoate, medroxyprogesterone acetate, megestrol acetate, melengestrol acetate, and medrogestone. The drug testolactone can be obtained by microbial transformation of progesterone or testosterone (Fried et al., 1953 *J. Am. Chem. Soc.* 75:5764). Cortisone is produced on an industrial scale by *Rhizophus nigricans* by microbiological C-11 hydroxylation of progesterone to yield 11-alpha-hydroxyprogesterone which can be converted to hydrocortisone and cortisone. Cortisone can be converted to corticosterone. Pregnanediol is a metabolite of progesterone, that can be isolated from pregnancy urine of women (Marrian, 1929 *Biochem. J.* 23:1090) and of cows, mares, and chimpanzees (Fish et al., 1942 *J. Biol. Chem.* 143:716). Accordingly, a preferred method of pregnanediol production is from isolated, pregnanediol producing animal cells genetically engineered according to the instant invention to produce increased levels of pregnenolone.

The fusion enzymes are used in the normal manner for enzyme-catalyzed chemical conversions and can be used in commercial enzyme reactors without significant modification of structure or procedure by those of ordinary skill in such processes. One method for production of steroids or their precursors and intermediates uses reconstituted systems similar to those, for example, of Palin et al. (1992), Akiyoshi-Shibata et al. (1991) or Wada et al. (1991), wherein the fusion proteins of the invention or cell extracts containing them replace corresponding single enzyme preparations.

A preferred use is the generation of transgenic livestock yielding low-cholesterol meat. Preferred transgenic livestock are cattle, sheep and pigs that contain constructs comprised of sequence encoding fusion enzymes of the invention comprised of proteins homologous to the host animal. Preferred non-human hosts contain minigene expression constructs that bear one or more introns so that the transcribed DNA product is processed similarly to naturally occurring DNA, thereby increasing expression efficiency. Particularly preferred hosts are those bearing minigene constructs comprising a transcriptional regulatory element that is tissue-specific for expression, and most preferably adipocyte-specific.

A preferred process of disposing or of lowering of cholesterol from meat comprises growing a transgenic non-human animal of the invention under conditions such that the fusion enzyme is expressed, and then isolating its meat. An alternative process for lowering cholesterol content of meat is to administer a fusion enzyme to a livestock animal, and then isolate its meat. Meat may also be contacted directly with the fusion enzyme under conditions allowing fusion enzyme activity and resultant cholesterol degradation.

To test for a suitable in vivo construct useful in livestock in a comparatively rapid, efficient, and cost-effective fashion, transgenic mice bearing minigenes are currently preferred. First a fusion enzyme expression construct is created and selected based on expression in cell culture as described in the Examples. Then a minigene capable of expressing that fusion enzyme is constructed using known techniques. Clark et al. (1993), among others, disclose minigenes that are adaptable by one of ordinary skill in the art to expression of fusion enzymes of the invention. A preferred minigene expresses the F2 construct.

Transgenic mice expressing the F2 minigene are made using known techniques, involving, for example, retrieval of fertilized ova, microinjection of the DNA construct into male pronuclei, and re-insertion of the fertilized transgenic ova into the uteri of hormonally manipulated pseudopregnant foster mothers. Alternatively, chimeras are made using known techniques employing, for example, embryonic stem cells (Rossant et al 1993) or primordial germ cells (Vick et al. 1993) of the host species. Insertion of the transgene is evaluated by Southern blotting of DNA prepared from the offspring mice. Such transgenic mice are then back-crossed to yield homozygotes. Changes in the amount of cholesterol in blood, fat, muscle and liver of the transgenic mice will be monitored. A preferred transgenic mouse strain is a strain with a genetic background predisposed to developing hypercholesterolemia and secondary tissue changes (atherosclerosis), which facilitates evaluating the effectiveness of a cholesterol disposal fusion enzyme. Blood concentrations of HDL and LDL cholesterol, tissue content of cholesterol and histologic changes in the vasculature as well as transgene expression at the RNA and protein level are monitored.

Preferred fusion enzyme constructs for creating the DNA transgene constructs to be microinjected into ova are those most effective in transiently transfected COS-1 cells. Particularly preferred constructs express F2 and its derivatives. F2 as disclosed in the Examples is a cDNA construction lacking introns or a tissue-specific promoter. It is now well-established that transgenes are expressed more efficiently if they contain introns at the 5' end, and if these are the naturally occurring introns (Brinster et al. 1988; Yokode et al. 1990). A particularly preferred class of minigenes contains two portions of the P450scc genomic gene substituting for the corresponding cDNA region (as described below), wherein P450scc is at the N-terminal end of the fusion enzyme. A preferred F2 minigene construct substitutes two portions of the P450scc genomic gene for the corresponding cDNA region. The whole P450scc gene is over 20 kb long (Morohashi et al. 1987) and contains a large intron >10 kb between exons 1 and 2 (Morohashi et al. 1987). PCR-amplification is used to create the substitution. PCR is used to amplify a 2 kb segment extending from the 3' end of exon 3 to the 5' end of exon 5, and a 2 kb segment extending from the 3' end of exon 6 to the 5' end of exon 9. The PCR-amplified segments of genomic DNA are subcloned, sequenced to ensure there are no PCR artifacts, and substituted for the corresponding segments of the P450scc cDNA in the F2 construct. This strategy furnishes the needed introns, preserves the ATG translational start site, and permits linkage of the desired promoter upstream. Alternatively, preferred minigenes are constructed having the 0.6 kb intron from rabbit β-globin gene inserted between a 5' enhancer and proximal promoter and a 3' fusion enzyme cDNA sequence. For liver-specific expression, the promoter/enhancer of the mouse albumin gene, where the sequences conferring liver-specific expression have been mapped (Gorski et al. 1986), is preferred. The promoter (−177 to +22 or alternatively −170 to −55) is then fused to base 46 of the P450scc gene by blunt-end ligation, and the whole construct is propagated in pUC19. Alternatively, the mouse albumin promoter is fused to the rabbit β-globin intron, which is in turn fused to the P450scc fusion cDNA. For adipocyte-specific expression, the distal enhancer from the −5.4 kb to −4.9 kb region of mouse adipocyte-specific aP2 gene (Graves et al. 1992) is preferred, since it is well characterized and has been shown to direct adipocyte-specific gene expression in transgenic mice. The 518 bp or the 183 bp region identified as the enhancer (Graves et al. 1993) are preferably used. For muscle-specific expression the proximal muscle-specific regulatory element of the skeletal muscle actin promoter (Walsh 1989; Santoro et al. 1991) is prepared similarly. The aP2 enhancer, unlike the promoter/enhancers of albumin and actin, has not previously been used to create transgenic mice. To ensure that these sequences, or others, are indeed sufficient to confer tissue-specific expression, they can be fused to the β-galactosidase gene and used to create transgenic mice. β-galactosidase activity in various tissues is assayed colorimetrically to demonstrate tissue-specific expression.

Transgenic mice expressing an F2 minigene are created using established procedures for creating transgenic mice, preferably in the C57BL/6 strain (Rubin et al. 1991 *Proc Natl Acad Sci USA;* Rubin et al. 1991 *Nature*). This strain is not usually used for transgenic mouse experiments, as the microinjections are more difficult and the number and size of the transgenic litters are small. However, when fed an atherogenic diet these mice consistently develop atherosclerotic lesions within 14–18 weeks, whereas BALB-C develop few, and C3H mice develop no such lesions even after eating the atherogenic diet for a year. The appearance or lack of appearance of the atherosclerotic plaques in the aortas of transgenic C57BL/6 mice provides a very sensitive and highly reliable indication that the cholesterol disposal enzyme is having a general effect to reduce total body cholesterol. Preferred strains, those susceptible to atherosclerosis, include mice deficient in apolipoprotein E ("apo(E)") or overproducing apolipoprotein (a) ("apo(a)"). Preferred strains can be made by genetic manipulation, for example, by genetic engineering to create recombinant BALB-C strains with altered apo(E) or apo(a) expression (Plump et al. 1992; Long et al. 1992).

Transgenic mice are constructed using now standard methods (Brinster et al. 1988; Yokode et al. 1990; Rubin et al. 1991 Proc Natl Acad Sci USA; Rubin et al. 1991 Nature). C57BL/6 mice are preferred. Fertilized eggs from timed matings are harvested from the oviduct by gentle rinsing with PBS and are microinjected with up to 100 nanoliters of a DNA solution, delivering about $10^4$ DNA molecules into the male pronucleus. Successfully injected eggs are then re-implanted into pseudopregnant foster mothers by oviduct transfer. Less than 5% of microinjected eggs yield transgenic offspring and only about ⅓ of these actively express the transgene: this number is presumably influenced by the site at which the transgene enters the genome.

Transgenic offspring are identified by demonstrating incorporation of the microinjected transgene into their genomes, preferably by preparing DNA from short sections of tail and analyzing by Southern blotting for presence of the transgene ("Tail Blots"). The preferred probe is a segment of a minigene fusion construct that is uniquely present in the transgene and not in the mouse genome. In the case of the F2 minigene exemplified herein, the human P450scc intron 1 is the probe and is prepared by PCR-amplification. When polynucleotides encoding fusion enzymes homologous to the host are integrated, the probe can comprise the nucleotide sequence encoding a novel joint region between enzymes in the fusion, for example, or other region unique to the transgene but not the host genome. Alternatively, substitution of a natural sequence of codons in the transgene with a different sequence that still encodes the same peptide yields a unique region identifiable in DNA and RNA analysis. Transgenic "founder" mice identified in this fashion are bred with normal mice to yield heterozygotes, which are back-crossed to create a line of transgenic mice. Tail blots of each mouse from each generation are examined until the strain is established and homozygous. Each successfully created founder mouse and its strain vary from other strains in the location and copy number of transgenes inserted into the mouse genome, and hence have widely varying levels of transgene expression. Selected animals from each established line are sacrificed at 2 months of age and the expression of the transgene is analyzed by Northern blotting of RNA from liver, muscle, fat, kidney, brain, lung, heart, spleen, gonad, adrenal and intestine.

Successfully constructed mouse lines are maintained on two different atherogenic diets and a low-fat control diet. Two different high-fat atherogenic diets are used to ensure that results are not unique to one particular diet (Rubin et al. 1991). The low-fat control is most preferably Purina laboratory mouse chow 5001, but any laboratory mouse chow which contains only about 4.5% (w/w) animal fat, less than about 0.03% cholesterol, and preferably no sodium cholate or casein is preferred. The preferred atherogenic diet is a cocoa butter diet containing about 15% fat, about 1.25% cholesterol, about 0.5% sodium cholate and about 7.5% casein. A second preferred atherogenic diet is the dairy butter diet containing about 15% fat, about 1.0% cholesterol, about 0.5% sodium cholate and about 20% casein.

The success of the cholesterol-disposal enzyme is assessed by measurement of serum cholesterol, triglycerides and lipoprotein, by measurement of tissue cholesterol, and by examining the formation of atherosclerotic plaques in the transgenic mice. Lipoproteins are isolated from blood plasma of sacrificed animals by buoyant density ultracentrifugation, and are analyzed by electrophoresis on nondenaturing 4–30% polyacrylamide gradient gels. Plasma lipids are measured colorimetrically using a microtiter plate reader; total plasma and tissue cholesterol and HDL-cholesterol and triglycerides are measured enzymatically. Atherosclerotic lesions in the aorta are quantitated on serial histologic sections stained with oil red O and measured microscopically using a calibrated eyepiece; data are summed as mean lesion area per animal. Mean lesion area and lipoprotein levels are compared by the two-tailed t-test and significance is confirmed by the Mann-Whitney U-test. Analysis of variance is used to test if changes in lesion areas can be attributed to lipoprotein differences in control and transgenic mice. Cholesterol disposal fusion enzyme MRNA is measured in tissues by Northern blotting and the protein by Western blotting. In the case of the F2 fusion, anti-human P450scc antisera is used.

Minigene constructs resulting in cholesterol disposal activity in transgenic mice or cholesterol cleavage activity in cell culture are selected for use in producing transgenic livestock. As is known to those of ordinary skill in the art of recombinant DNA and transgene technology, a polynucleotide of the invention is transferred, if necessary, from the selected minigene to an appropriate host minigene vector, or the minigene can be suitably revised, to achieve introduction, integration, and tissue-specific expression in a livestock transgenic host cell such that transgenic animal lines of the invention are obtained. Such techniques and vectors available for each species of livestock are well known to those in the field. For example, Cook et al. (1993) recently demonstrated that liver-specific expression by a rat promoter was retained in transgenic chickens. Pursel et al. (1990) produced transgenic pigs expressing human genes driven by mouse promoters.

In addition to the above procedures, which can be used for preparing recombinant DNA molecules and transformed host animals in accordance with the practices of this invention, other known techniques and modifications thereof can be used in carrying out the practice of the invention. Many recent U.S. patents disclose plasmids, genetically engineered cells and embryos, and methods of conducting transgenic animal engineering that can be used in the practice of the present invention. For example, U.S. Pat. No. 4,736,866 discloses vectors and methods for production of a transgenic non-human eukaryotic animal whose germ cells and somatic cells contain a gene sequence introduced into the animal, or an ancestor of the animal, at an embryonic stage. U.S. Pat. No. 5,087,571 discloses a method of providing a cell culture comprising (1) providing a transgenic non-human mammal, all of whose germ cells and somatic cells contain a recombinant gene sequence introduced at an embryonic stage; and (2) culturing one or more of said somatic cells. U.S. Pat. No. 5,175,385 discloses vectors and methods for production of a transgenic mouse whose somatic and germ cells contain and express a gene at sufficient levels to provide the desired phenotype in the mouse, the gene having been introduced into said mouse or an ancestor of said mouse at an embryonic stage, preferably by microinjection. A partially constitutive promoter, the metallothionein promoter, was used to drive heterologous gene expression. U.S. Pat. No. 5,175,384 discloses a method of introducing a transgene into an embryo by infecting the embryo with a retrovirus containing the transgene. U.S. Pat. No. 5,175,383 discloses DNA constructs having a gene, homologous to the host cell, operably linked to a heterologous and inducible promoter effective for the expression of the gene in the urogenital tissues of a mouse, the transgene being introduced into the mouse at an embryonic stage to produce a transgenic mouse. Even though a homologous gene is introduced, the gene can integrate into a chromosome of the mouse at a site different from the location of the endogenous coding sequence. The viral MMTV promoter was disclosed as a suitable inducible promoter. U.S. Pat. No. 5,162,215 discloses methods and vectors for transfer of genes in avian species, including livestock species such as chickens, turkeys, quails or ducks, utilizing pluripotent stem cells of embryos to produce transgenic animals. Transgenic chickens expressing a heterologous gene are disclosed. U.S. Pat. No. 5,082,779 discloses pituitary-specific expression promoters for use in producing transgenic animals capable of tissue-specific expression of a gene. U.S. Pat. No. 5,075,229 discloses vectors and methods to produce transgenic, chimeric animals whose hemopoietic liver cells contain and express a functional gene driven by a liver-specific promoter, by injecting into the peritoneal cavity of a host fetus the disclosed vectors such that the vector integrates into the genome of fetal hemopoietic liver cells.

Although some of the above-mentioned patents and publications are directed to the production or use of a particular gene product or material that are not within the scope of the present invention, the procedures described therein can easily be modified to the practice of the invention described in this specification by those skilled in the art of fermentation, genetic engineering or steroid synthesis.

Fusion enzymes of the invention may also be used as a standard in immunoassays and other assays intended to determine the presence of the normal individual enzymes in humans. Polypeptides of the invention may be used to prepare antisera and monoclonal antibodies to the regions of assembly between the enzymes comprising the fusion proteins.

The invention now being generally described, the same will be better understood by reference to the following detailed examples, which are provided for illustration of the invention and are not intended to be limiting of the invention unless so specified.

EXAMPLES

EXAMPLE 1

MATERIALS AND METHODS

Strains, cell and vectors

E. coli strains XL-1 Blue recA$^-$ (recA1, lac$^-$, endA1, gyrA96, thi, hsdR17, supE44, relA1, (F' proAB, lacI$^q$, lacZDeltaM15, Tn10)) and GM2163 (Fara-14, leuB6, tonA31, lacY1, tsx-78, supE44, galK2, galT22, hisG4, rpsL136, xyl-5, mtl-1, thi-1, dam-13::Tn9, dcm-6, hsdR2, mcrB$^-$, mcrA$^-$) were used for all cloning and sequencing. COS-1 cells were obtained from the ATCC. Mammalian expression vector pECE (Ellis et al 1986) and transfection control vector RSV β-Gal (Edlund et al 1984) were obtained from W. Rutter (UCSF), pUC19 from Pharmacia LKB Biotechnology (Alameda Calif.) and pBluescript KS was purchased from Stratagene (La Jolla Calif.). The vectors expressing P450scc and Adx alone are pEscc and pEadx (Brentano and Miller 1992) and the vector expressing AdRed is pE-AR- (Brentano et al 1992).

Amplification of cDNAs

The cDNAs for human P450scc (SEQ ID NO: 1) (FIG. 1; Chung et al 1986; U.S. Pat. No. 5,045,471), for the short, 18-form of AdRed (SEQ ID NO: 3) (FIG. 2; Solish et al 1988) and for Adx (SEQ ID NO: 5) (FIG. 3; Picado-Leonard et al 1988), were isolated as EcoRI fragments purified from a 1% agarose gel using Geneclean II (Bio 101 Inc., La Jolla Calif.). Each 100 μl PCR reaction contained 10 ng of template DNA, 10 mM Tris, pH 8.0, 50 mM KCl, 150 μg/ml bovine serum albumin, 200 μM each of dGTP, dATP, dTTP and dCTP, 0.2 μM of each of the two phosphorylated primers used and 1 unit of Taq DNA polymerase. Amplifications were carried out with Taq polymerase in a thermal cycler programmed for 25 cycles of denaturation at 95° C. for 1 min, annealing at 55–60° C. for 1 min, extension at 72° C. for 2–2.5 min and final extension at 72° C. for 7 min. The sizes of the resulting PCR products were analyzed by electrophoresis in 1.5% agarose gel stained with ethidium bromide. The PCR products were purified from agarose gel using Geneclean II and subcloned as blunt-ended fragments into the SmaI site of pBluescript KS for dideoxy sequencing and subsequent cloning.

Cell Culture and Transfection

COS-1 cells were propagated in Dulbecco's Modified Eagle's medium containing 4.5 g glucose, 10% fetal bovine serum and 50 μg/ml gentamycin. Cells were maintained at 37° C. in 5% $CO_2$. Cultures of sub-confluent COS-1 were split such that each 10 cm tissue culture dish received an equal number of cells. The cells were allowed to adhere overnight and were transfected by calcium phosphate precipitates with plasmid DNA samples prepared by CsCl gradient centrifugation plus either 5 μg RSV β-gal or 5 μg of RSV Luc as an internal control of transfection efficiency. After 16 h the medium was replaced with fresh medium and the cells allowed to grow for 48 h. The medium was then replaced with fresh medium without serum containing 0.5, 1.0, 2.0, 3.0, or 5 μM 22-hydroxycholesterol, and the medium and cells were harvested 24 h later.

Immunoassay of Pregnenolone

Cholesterol side-chain cleavage activity was measured by pregnenolone formation in cell culture using a RIA. The culture medium (1 or 2 ml) was extracted with 10 vol diethyl ether, and the extract was dried under nitrogen, then purified by partition chromatography on System II Celite microcolumns by stepwise elution with isooctane (3.5 ml) and 5% ethyl acetate in isooctane (2 ml). Microcolumns were prepared by packing 2 g diatomaceious earth (Sigma) into 5-ml pipettes. The samples were dried under nitrogen, resuspended in assay buffer, and incubated with antipregnenolone antiserum and [$^3$H] pregnenolone (both from ICN Biomedicals, Inc., Carson, Calif.) for 16 h at 4 C. Unbound pregnenolone was adsorbed with charcoal and centrifuged at 3000×g for 15 min at 4 C, and the supernatant was counted in a liquid scintillation counter. All samples were assayed in triplicate. Inter- and intraassay variations were less than 10%. Data are reported as the mean ±SEM of three experiments assayed in triplicate, and statistical comparisons were performed with paired t tests.

Results were normalized for variations in transfection efficiency by measuring either β-galactosidase or firefly luciferase activity of cells harvested 72 hours after transfection. Cells were lysed by incubation in 150 μl 250 mM Tris pH 7.5, 0.1% Triton X 100, on ice for 5 min. The cell lysate was cleared by microcentrifugation for 10 minutes and 50 μl of the supernatant was used either for the measurement of β-galactosidase or luciferase activities. For β-galactosidase activity 50 μl of supernatant was combined with 450 μl of 100 mM Na$_2$HPO$_4$, 10 mM KCL, 5% β-mercaptoethanol, 1 mM MgCl$_2$ and 100 μl 4 mg/ml ONPG was added to initiate the reaction. Samples were incubated at 30° C. for 1 h and the β-galactosidase activity was determined by absorbance at 420 nm. For luciferase activity 50 μl of supernatant was added to 200 μl luciferase assay buffer (25 mM glycyglycine, 15 mM MgSO$_4$, 4 mM EGTA, 15 mM potassium phosphate, pH7.8, 1 mM DTF, 2 mM ATP). The reaction was initiated by the addition of 100 μl of 0.2 mM luciferin then read on a luminometer.

Northern and Western Blotting

Northern blotting was done in MOPS formaldehyde/1.0% agarose gels with isolated cDNA inserts for human P450scc (SEQ ID NO: 1) (FIG. 1; Chung et al 1986), Adx (SEQ ID NO: 5) (FIG. 3; Picado-Leonard et al 1988), AdRed (SEQ ID NO: 1) (FIG. 2; Solish et al 1988), and GAPDH (Tokunaga et al 1987). For Western immunoblotting, transfected cells were harvested by centrifugation 72 hours after transfection, washed twice in phosphate buffered saline (PBS) then treated for 5 min in PBS without Mg$^{2+}$ and Ca$^{2+}$. The cells were stripped from the plate using a rubber policeman and pelleted at 1000 g for 2 min, resuspended in Sucrose buffer (2.5 M sucrose, 50 mM ethanolamine, Tris-HCl, pH 7.5, 1 mM EDTA) and subjected to 2×5 sec bursts with a sonicator (Artek Systems) at a setting of 20. Proteins were separated on NaDodSO$_4$/4–20% polyacrylamide gradient gels, electroblotted to nitrocellulose, and probed with antisera to human P450scc, and AdRed, as follows. Total protein content was determined after cell disruption with two 5 sec bursts using a sonicator (Artek Systems Corp.) at a setting of 20, and an equal volume of 2× loading buffer (50 mM Tris-HCl pH 6.8, 2% NaDodSO$_4$, 5% β-mercaptoetanol, 10% glycerol, 0.005% bromophenol blue) was added. Samples were boiled for 5 min and then separated by electrophoresis on NaDodSO$_4$, 4–20% acrylamide gradient gels. The proteins were then electro-transferred to nitrocellulose in Tris-HCl pH 8.4, 193 mM glycine, 20% methanol for 1 h at 4° C., and immunoblotting was done using antisera specific to human P450scc, Adx, AdRed (Black et al 1993), P450c17 (Lin et al 1993), and OR (a generous gift from C. R. Wolf) as described (Black et al 1993). The amounts of RNA or protein loaded were normalized for transfection efficiency.

RESULTS

Design and Construction of the Fusion Proteins

Figure 5:
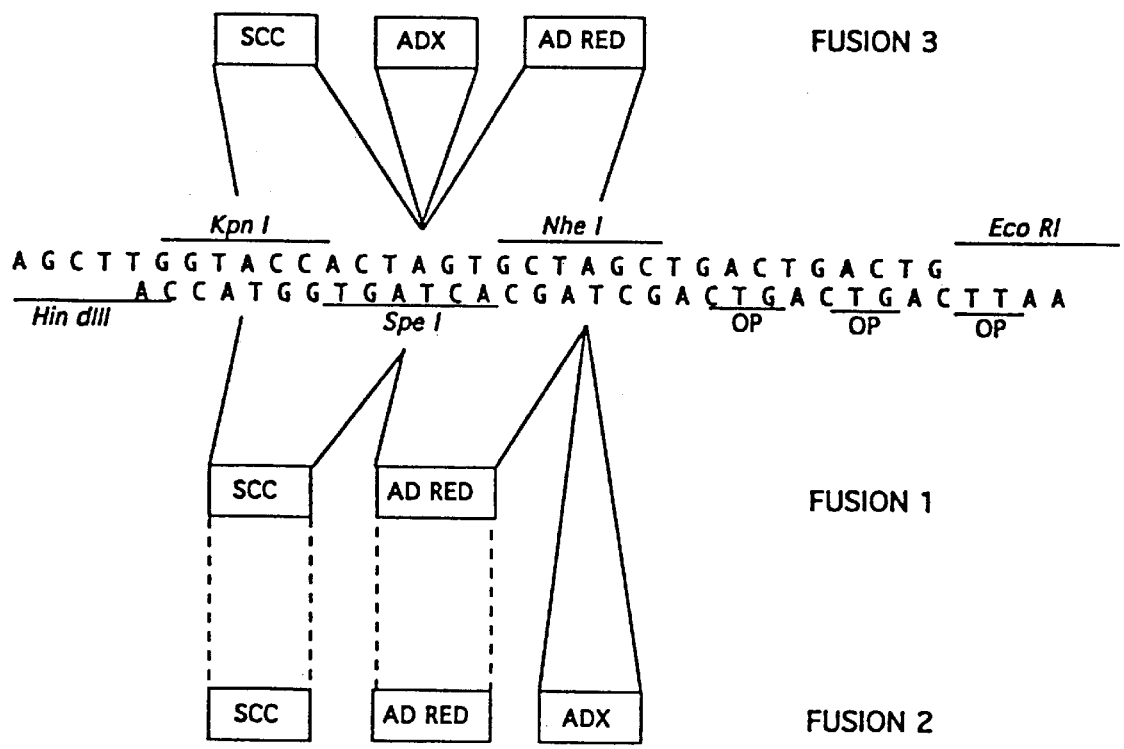
FIG. 5 is a schematic demonstrating the specific design of expression vectors and fusion proteins F1, F2 and F3. The double-stranded oligonucleotide (SEQ ID NO: 7; SEQ ID NO. 8) shown was synthesized and substituted for the HindIII/EcoRI segment of polylinker in pUC18, to yield the intermediate cloning vector pUC-SF. cDNA fragments for P450scc, Adx, and AdRed were prepared by PCR and replacement cloning as described in the methods. The PCR primers also functioned as linkers encoding hinge protein sequences and contained the unique KpnI, SpeI, and NheI sites shown; this permitted their assembly into open reading frames encoding the three fusion proteins shown. The assembled sequences were excised, sub-cloned into pECE and expressed in transfected COS-1 cells.

The human cDNAs for P450scc (SEQ ID NO: 1), Adx (SEQ ID NO: 5) and AdRed (SEQ ID NO: 3) were re-engineered by PCR amplification tactics so they could be assembled in a cassette-like fashion in the order depicted in FIG. 5. This was facilitated by constructing an intermediate carrier vector by replacing the pUC polylinker with a linker providing the required cloning sites and downstream translational stop codons in each reading frame as well as unique sites to permit excision of the cDNA fusion construction for cloning in the expression vector pECE. Two complementary 33-base oligonucleotides (SEQ ID NO: 7; SEQ ID NO: 8) were synthesized and annealed to produce the desired polylinker (FIG. 5). This was substituted for the HindII/EcoRI region of the pUC19 polylinker to yield the vector pUC-SF, which was used to assemble the PCR-modified cDNAs for P450scc, Adx and AdRed. These were then cloned into the expression vector pECE (Ellis et al 1986). pUC-SF includes KpnI, SpeI and NheI sites for subcloning the DNAs for P450scc (between the KpnI and SpeI sites), AdRed (between the SpeI and NheI sites) and Adx (into the NheI site only or into the SpeI site. The linker encodes stop codons in each reading frame after the NheI site (COOH end in all constructions); the KpnI and EcoRI sites, which are unique in all three constructions, allow directional subcloning of the fusion constructions into pECE.

Three fusion ("F") constructions were made (FIG. 5). F1, H$_3$N-P450scc-AdRed-COOH, was built to test the possibility that the iron-sulfur protein, which functions as an electron shuttle protein for all mitochondrial forms of P450 (Lambeth et al 1979, Hanukoglu and Jefcoate 1980), might be eliminated, since the more plentiful microsomal P450 enzymes employ a flavoprotein analogous to AdRed, but require no iron-sulfur protein (Miller 1988). F3, H$_3$N-P450scc-Adx-AdRed-COOH, mimics the sequence in which electrons are passed endogenously. F2, H$_3$N-P450scc-AdRed-Adx-COOH, was built to increase the rotational mobility of Adx to potentially enhance its interaction with both P450scc and AdRed; hence in F2 Adx was placed on a short "tether" at the carboxyl terminus of the fusion protein. All fusions retained P450scc at the amino-terminus because previous fusion constructions with microsomal P450 enzymes were active only when the P450 moiety was at the amino-terminus (Sakaki et al 1990).

The mitochondrial leader signal of P450scc was retained in each fusion protein but the leaders of Adx and AdRed, and the translational stop codons and 3' untranslated regions of all three cDNAs were removed. The final expression vector provides appropriate 3' untranslated regions and polyadenylation signals. The 1562 bp P450scc sequence (full length P450scc sequence, SEQ ID NO: 1) was amplified using primers #1 (GGGTACCATGCTGGCCAAGGGTC) (SEQ ID NO: 11) and #4 (GACTAGTGCCGTCGGTCTGC TGGGTTGCTTCCTG) (SEQ ID NO: 12); the central ApaI/EcoRV fragment, which contained PCR errors, was replaced with the corresponding fragment of the cDNA. To avoid PCR errors, the ends of the 1367 bp AdRed coding sequence (full length AdRed sequence, SEQ ID NO: 3) were amplified as 200–300 bp fragments using primers #5 (GACTAGTTCCACACAGGAGAAGACC) (SEQ ID NO: 13) and #6 (TGACATTCTCACCTCGGG) (SEQ ID NO: 14) for the 5' end, and primers #7 (GTATAAG AGCCGCCCTGTCGAC) (SEQ ID NO: 15) and #8 (GGCTAGCGCCGTCGGTGTGGCCCAGGAGGCGCAG) (SEQ ID NO: 16) for the 3' end. The middle portion of the AdRed coding sequence (full length Adx sequence; SEQ ID NO: 5) was isolated as a BclI/SalI fragment and joined to the PCR products. The 371 bp Adx coding sequence (full length Adx sequence, SEQ ID NO: 5) was amplified using primers #9 (GGCTAGCAGCAGCTCAGAAGAT) (SEQ ID NO: 17) and #10 (GGGCTAGCGCCGTCGGTGGAGGTCT TGCCCAC) (SEQ ID NO: 18).

Primers #1, #4, #5, #8, #9 and #10 (SEQ ID NOS: 11, 12, 13, 16, 17 and 18, respectively) introduced the additional sequences needed to create the peptide hinges and to provide the unique restriction sites needed to assemble the fusion constructions. The length and amino acid sequences of the hinges were based on a study of the hinge regions of naturally occurring multi-domain proteins (Argos 1990) and on the need to place unique restriction sites in each hinge that were not found in the human P450scc (SEQ ID NO: 1), Adx (SEQ ID NO: 3), or AdRed (SEQ ID NO: 5) cDNA sequences used in the constructions. Of course the unique restriction sites are for convenience in the generation of cassettes that facilitate creation of desired fusions and are not a limitation of the instant invention. Primer #4 (SEQ ID NO: 12) encodes the hinge sequence Thr-Asp-Gly-Thr-Ser (SEQ ID NO: 9) containing a unique SpeI site and primers #8 (SEQ ID NO: 16) and #10 (SEQ ID NO: 18) encode the hinge sequence Thr-Asp-Gly-Ala-Ser (SEQ ID NO: 10)

containing a unique NheI site. Thus each linker sequence contained several hydrophilic residues. Human cells contain two forms of AdRed MRNA that arise by alternate splicing and differ by 18 bases (Solish et al 1988, Lin et al 1990). The longer, 18+ form of AdRed represents only about 1% of total AdRed MRNA (Brentano et al 1992), and is inactive (Lin et al 1990, Brandt and Vickery 1992). Hence only the abundant 18- form of AdRed was used in the constructions. All constructions were sequenced in their entirety to rule out PCR artifacts or other errors.

Enzymatic Activity of the Fusion Proteins

The various constructions were transfected into COS-1 cells and enzymatic activity was assessed by measuring the conversion of 22-hydroxycholesterol to pregnenolone using radioimmunoassay. This assay proved to be substantially more sensitive and reproducible than conversion of radio-labelled mevalonolactone or cholesterol to pregnenolone. Controls consisted of cells transfected with the pECE vector alone, with a pECE vector expressing P450scc alone, and with various combinations of pECE vectors separately expressing P450scc, Adx and AdRed. Doubly and triply transfected cells received equimolar amounts of each plasmid so that the abundance of P450scc would be rate-limiting, as P450scc is the least abundant of the three components in various steroidogenic tissues (Hanukoglu et al 1990).

Initial experiments measured pregnenolone production after 24 hours of incubation with concentrations of 22-hydroxycholesterol from 0.5 to 5.01-$\mu$M (Table 1).

Table 1 shows the production of pregnenolone by COS-1 transfected cells. Cells were transfected with masses of plasmid DNAs calculated to provide equimolar amounts of P450scc sequences. Cells were incubated with the indicated concentrations of 22-hydroxycholesterol for 24 h, then the culture medium was harvested and pregnenolone was measured in triplicate for each transfection. Data are from three separate transfections, each with a different plasmid preparation, and are shown, normalized for transfection efficiency, (in ng/ml) as mean ±SEM (n=3). The vectors are named in the text; "/" indicates co-transfection; AR+ and AR- refer to the 18+ and 18- forms of AdRed, respectively.

1988) and adrenodoxin reductase (Brentano et al 1992) are expressed in all tissues examined. Previous studies (Zuber et al 1988) have shown that COS-1 kidney cells contain both of these electron transport proteins. Cells doubly transfected with vectors expressing P450scc and either the 18+ or 18- form of AdRed produced no more pregnenolone than cells transfected with the vector expressing P450scc alone. This suggests that the amount of endogenous AdRed produced by the COS-1 cells was sufficient to saturate the P450scc produced by the vector, so that no additional pregnenolone production was seen. However cells doubly transfected with P450scc and Adx produced more pregnenolone at high substrate concentrations, and cells triply transfected with all three vectors made 1.5 to 2-fold more pregnenolone (Table 1). This indicates that the endogenously produced COS-1 cell adrenodoxin appears to be insufficient for maximal P450scc activity. The F1 fusion was essentially equivalent to the triple transfections, but the F2 fusion produced substantially more pregnenolone than the other transfections, especially when incubated with 3–5 $\mu$M substrate. The F3 fusion initially appeared more active, but results with this construction were variable, as shown by the larger standard errors (Table 1).

Figure 6A:
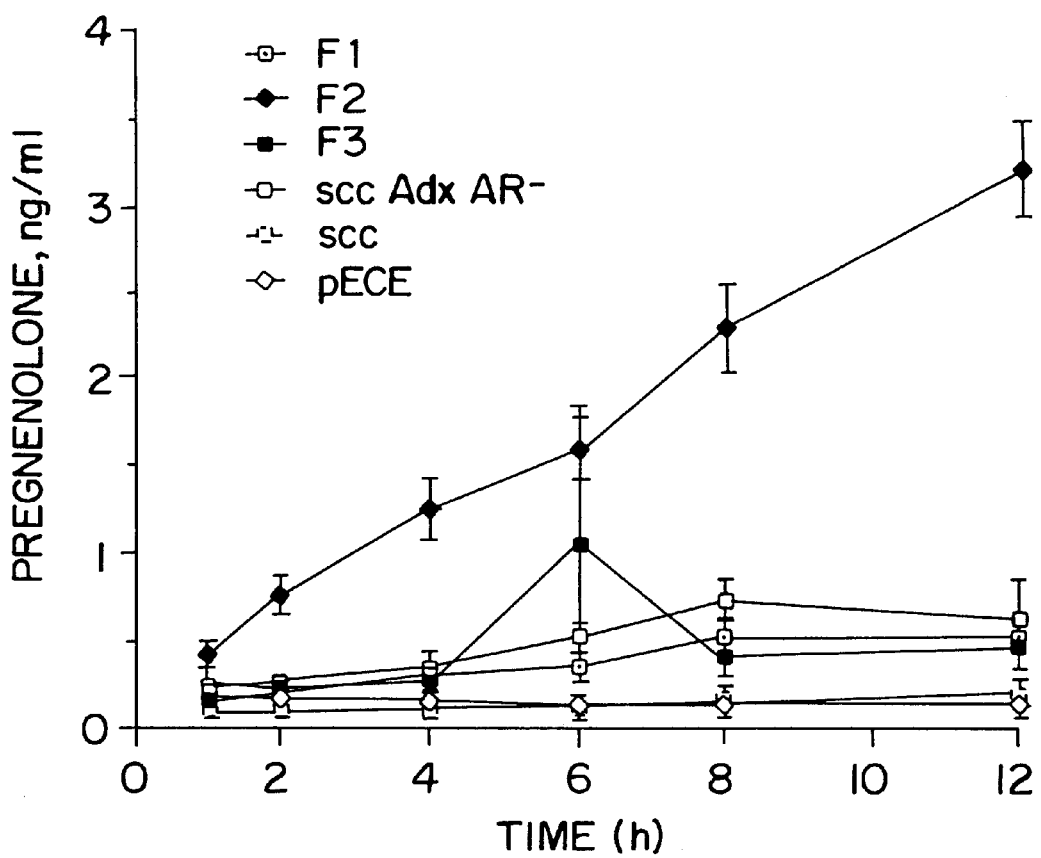
FIGS. 6A and 6B are schematics demonstrating the production of pregnenolone by transfected COS-1 cells. Cultures at about 60% confluence in 10 cm dishes (Falcon) were transfected with plasmids in masses varied to yield amounts of P450scc sequences equivalent to 2 pmol of the vector expressing P450scc alone.
Figure 6B:
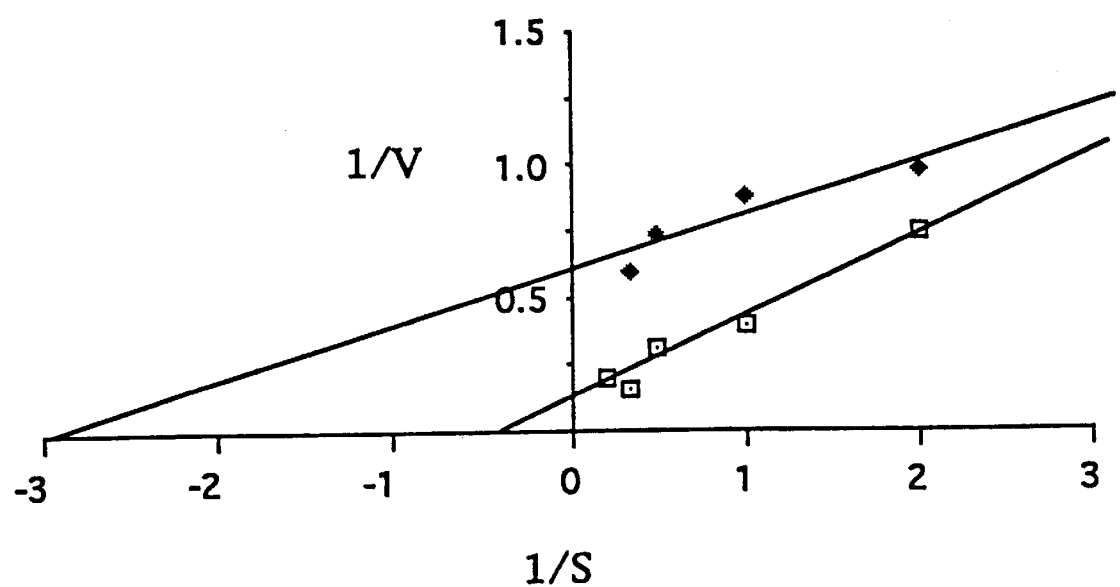
Figure 7A:
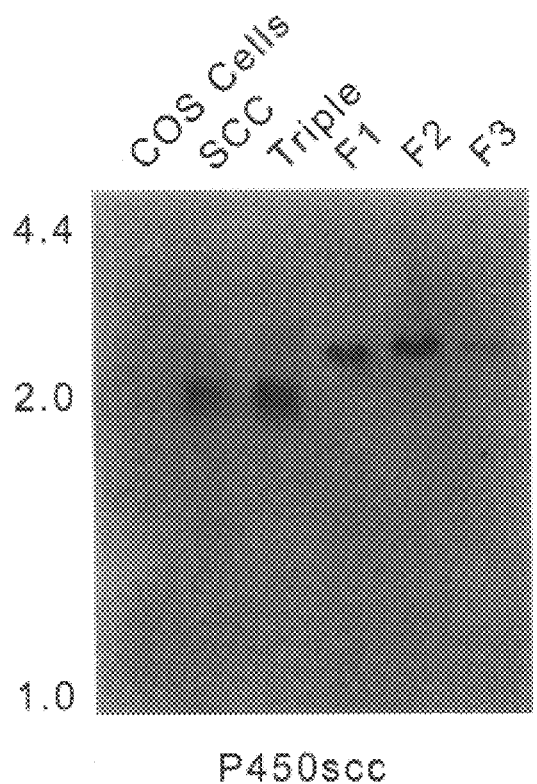
FIGS. 7A–7D are schematics depicting RNA produced by the fusion vectors as determined by Northern blotting. Cells were transfected as in FIG. 6A, harvested 48 hrs later, and 10 $\mu$g of total cellular RNA was run in each lane. The molecular size markers in kb are from bacteriophage $\lambda$ cut with HindIII and run in another lane. The blot was probed sequentially with $^{32}$P-labeled cDNAs for P450scc (FIG. 7A), AdRed (FIG. 7B), Adx (FIG. 7C), and glyceraldehyde phosphate dehydrogenase (GAPDH.
Figure 7B:
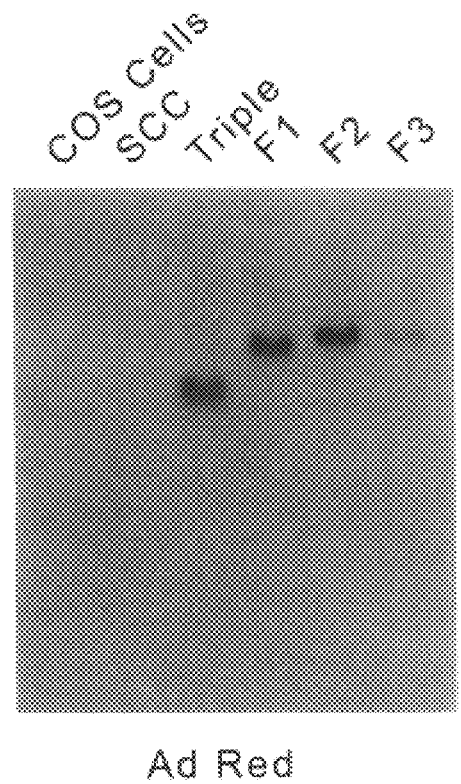
Figure 7C:
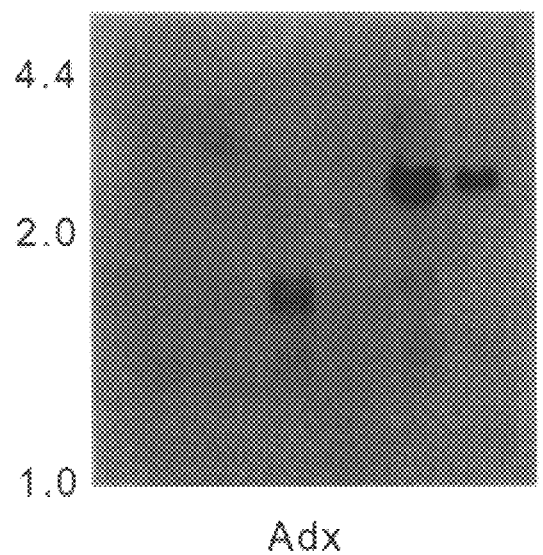
Figure 7D:
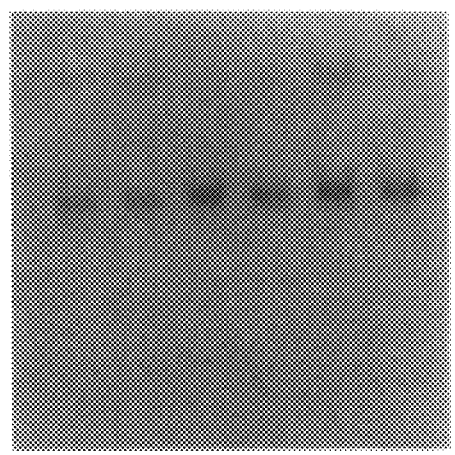

To examine the kinetics of pregnenolone production by the three fusion proteins incubations of various transfectants were done for various times up to 12 h (FIG. 6a). The triply transfected cells and those transfected with F1 again produced similar amounts of pregnenolone which were greater than those produced by cells transfected with the vector expressing P450scc alone. The F3 construction again gave inconsistent results. However cells transfected with the vector expressing construction F2 consistently produced abundant pregnenolone; after 12 hours of incubation F2 produced 5 to 6 times as much pregnenolone as did the other cultures. Lineweaver-Burke analysis of dose-response data for triply transfected cells yielded a Km of 0.37 $\mu$M, and a Vmax of 1.7 ng pregnenolone/ml of culture medium/24 h for P450scc. Similar analysis of the F2 construction yielded a Km of 2.85 and a Vmax of 9.1 ng/ml/24 h (FIG. 6b). Previous measurements of the Km for P450scc range widely from the nano-to milli-molar range because of differences in

TABLE 1

| TRANSFECTED VECTOR(s) | CONCENTRATION ($\mu$M) OF ADDED 22OH-CHOLESTEROL | | | | | |
|---|---|---|---|---|---|---|
| | 0 | 0.5 | 1.0 | 2.0 | 3.0 | 5.0 |
| pECE | 0.05 ± 0.03 | 0.11 ± 0.05 | 0.14 ± 0.04 | 0.14 ± 0.03 | 0.18 ± 0.01 | 0.16 ± 0.03 |
| scc | 0.07 ± 0.01 | 0.69 ± 0.29 | 0.83 ± 0.40 | 0.70 ± 0.38 | 0.76 ± 0.47 | 0.80 ± 0.45 |
| scc/AR+ | 0.07 ± 0.03 | 0.29 ± 0.09 | 0.48 ± 0.13 | 0.53 ± 0.17 | 0.51 ± 0.17 | 0.54 ± 0.18 |
| scc/AR− | 0.10 ± 0.01 | 0.65 ± 0.32 | 0.87 ± 0.44 | 0.71 ± 0.29 | 0.87 ± 0.37 | 0.62 ± 0.17 |
| scc/Adx | 0.08 ± 0.01 | 1.07 ± 0.60 | 0.86 ± 0.32 | 1.22 ± 0.47 | 0.66 ± 0.31 | 1.32 ± 0.56 |
| scc/Adx/AR+ | 0.10 ± 0.01 | 1.18 ± 0.59 | 1.15 ± 0.44 | 1.58 ± 0.67 | 1.53 ± 0.55 | 1.72 ± 0.69 |
| scc/Adx/AR− | 0.14 ± 0.03 | 1.03 ± 0.42 | 1.43 ± 0.39 | 1.38 ± 0.73 | 1.68 ± 1.09 | 1.00 ± 0.23 |
| F1 | 0.09 ± 0.01 | 1.68 ± 0.72 | 1.93 ± 0.50 | 2.15 ± 0.54 | 1.61 ± 0.86 | 1.61 ± 0.30 |
| F2 | 0.11 ± 0.02 | 1.35 ± 0.37 | 2.52 ± 0.83 | 3.22 ± 0.27 | 6.22 ± 1.37 | 5.01 ± 1.10 |
| F3 | 0.13 ± 0.03 | 4.35 ± 2.72 | 6.31 ± 4.19 | 6.98 ± 4.04 | 5.34 ± 1.92 | 7.55 ± 3.70 |

Substrate concentrations of 3–5 $\mu$M appeared to be saturating for all constructions. Cells transfected with the vector expressing P450scc alone consistently made small amounts of pregnenolone that were that were significantly greater than the background measured in cells transfected with the pECE vector alone, indicating that the COS-1 cells have low levels of Adx and AdRed or of other proteins able to substitute for their activity. The expression of P450scc is confined to steroidogenic tissues (for review see Miller 1988), whereas both adrenodoxin (Picado-Leonard et al techniques and difficulty in purifying the enzyme. Our values for P450scc and F2 were calculated in identical systems, and thus can be used directly to compare the differences in Km and Vmax in these two enzymes, although the actual units cannot be compared directly to other systems. The F2 construction converts cholesterol to pregnenolone more efficiently than does the natural, three-component system: the Vmax of F2 was five-fold greater (9.1 vs 1.7 ng/ml/day). This suggests that the slowness of the endogenous reaction is not determined solely by access of free cholesterol substrate to the P450scc moiety. The increased Vmax of the F2 fusion suggests that the time needed for the association of AdRed with Adx and for the subsequent association of Adx with P450scc contributes significantly to the low turnover number of the endogenous P450scc system.

Expression and Stability of the Fusion mRNAs and Proteins

Northern blotting of RNA from COS-1 cells transfected with the various fusion constructions and controls showed that all of the constructions were transcribed into stable mRNAs of the predicted sizes and that each fusion MRNA contained the predicted components (FIG. 7). The low endogenous levels of AdRed and Adx mRNAs present in COS-1 cells cannot be seen in the RNA samples from untransfected COS-1 cells or cells transfected with the P450scc vector alone, but all three individual components are readily seen in the triply transfected cells. The RNA encoded by the F1 construction hybridizes to both P450scc and AdRed probes but not to the Adx probe, while the RNA encoded by the F2 and F3 constructions hybridizes to all three probes, as predicted. Even though the same mass of F2 and F3 plasmids were transfected, FIG. 7 and other experiments consistently showed less F3 RNA. Since the expression vectors were built identically, this may be due to decreased stability of F3 RNA.

Figure 8A:
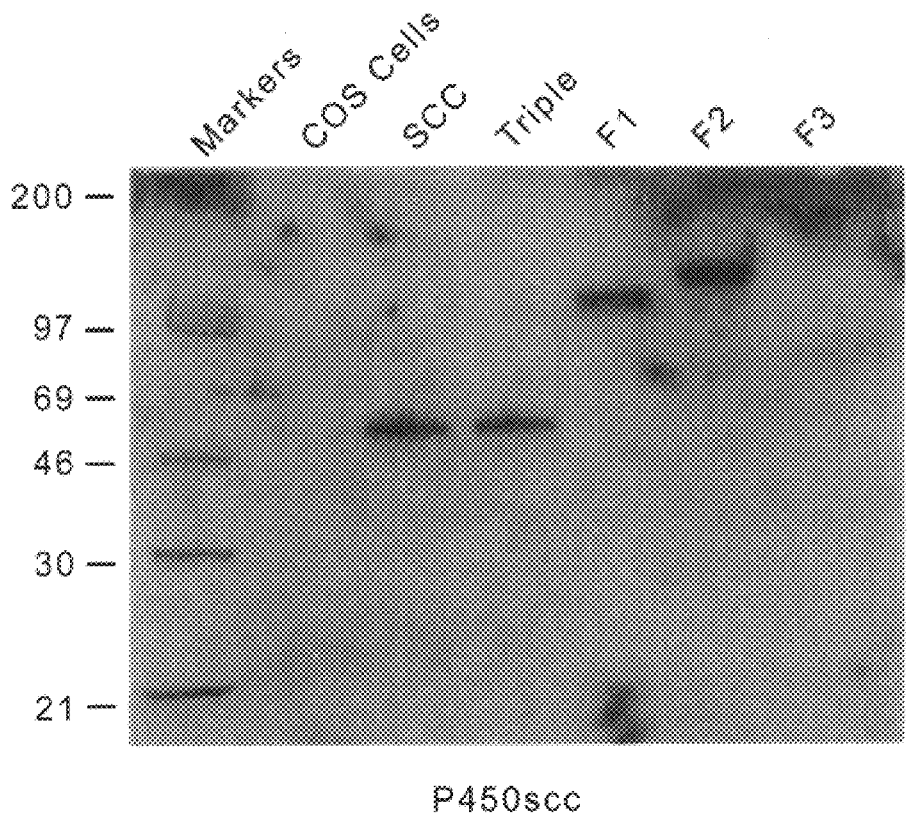
FIGS. 8A and 8B are schematics depicting proteins produced by the fusion vectors as determined by Western blotting. Each lane contains an equivalent amount of protein as assayed colorimetrically and corrected for transfection efficiency. Molecular sizes of standards are in kilo Daltons. Duplicate gels were probed with antibodies to human P450scc (FIG. 8A) and AdRed (FIG. 8B).
Figure 8B:
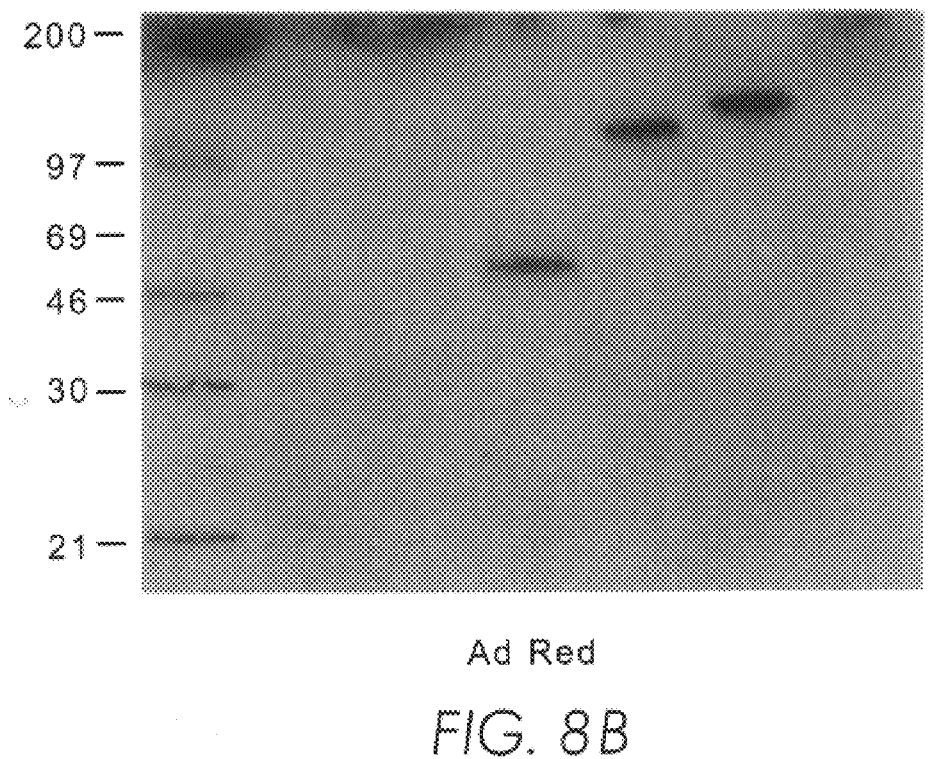
Figure 9A:
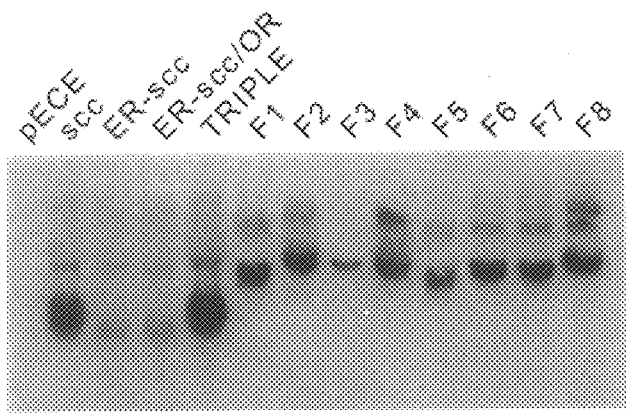
FIGS. 9A–9D are schematics depicting RNA produced by the fusion vectors as determined by Northern blotting. RNA was prepared from COS-1 cells transfected with the various constructions indicated. "ER-P450scc/OR" designates an RNA sample from cells doubly transfected with two vectors, one expressing ER-P450scc and the other expressing OR. "Triple transfection" designates cells transfected with equimolar amounts of three vectors separately expressing normal human P450scc, AdRed and Adx. "pECE" is the expression vector with no cDNA insert. Samples of 20 $\mu$g of RNA were electrophoresed through a MOPS-formaldehyde-1% agarose gel and transferred to Hybond-N nylon membrane (Amersham). A single blot was sequentially probed with $^{32}$P-labeled cDNAs for human P450scc (FIG. 9A), Adx (FIG. 9B), AdRed (FIG. 9C), and OR (FIG. 9D). The blot was boiled in 10 mM Tris, pH 7.4, 5 mM EDTA, 1% NaDodSO$_4$, and re-autoradiographed between probings to ensure that all radioactivity from the previous probe had been removed. HindIII-cut bacteriophage PM-2, run in another lane, were used as markers and permitted alignment of the corresponding bands in the four autoradiographs.
Figure 9B:
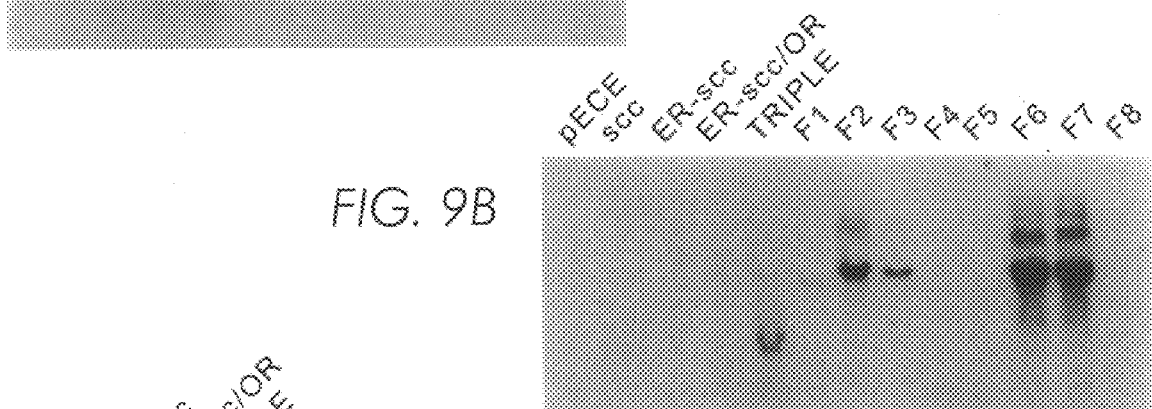
Figure 9C:
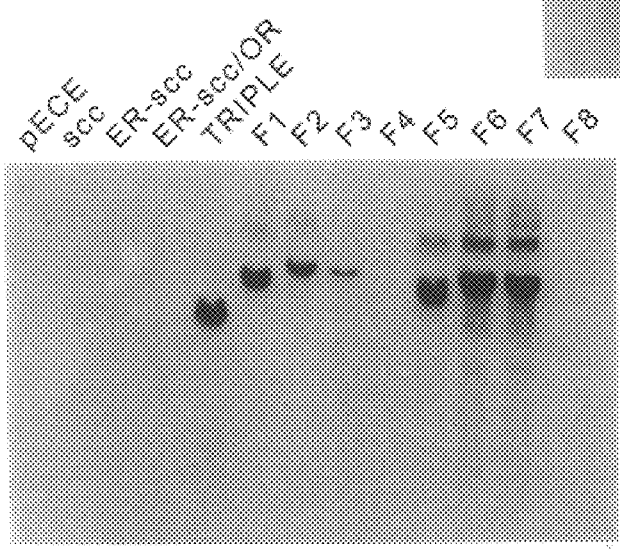
Figure 9D:
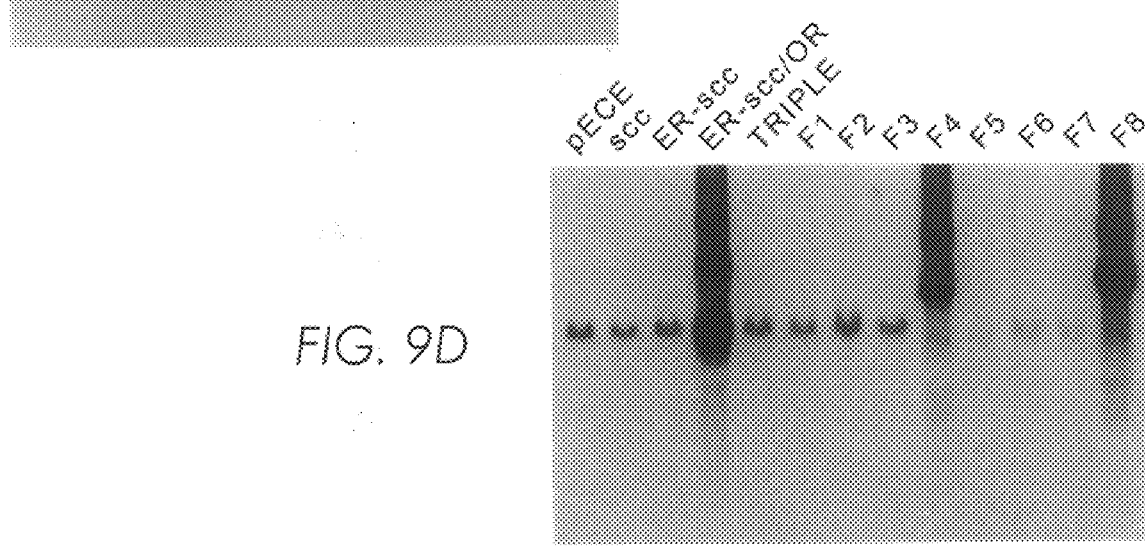
Figure 10A:
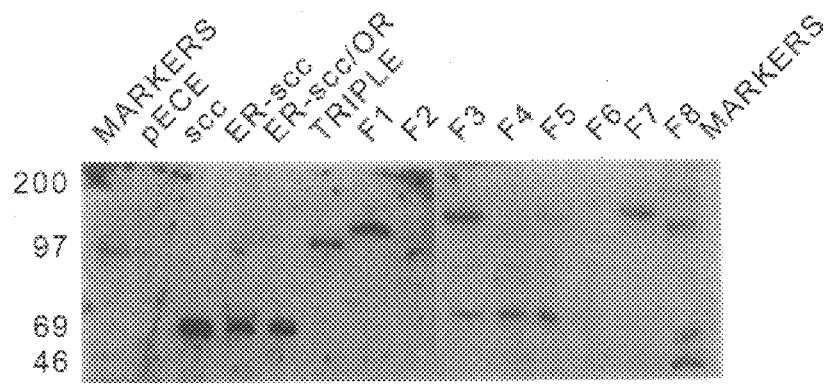
FIGS. 10A–10D are schematics depicting proteins produced by the fusion vectors as determined by Western blotting. Varying amounts of protein were loaded in each. Each lane contains an equivalent amount of protein as determined by normalization to a constant ratio of protein to transfection efficiency. Each gel presents proteins from COS-1 cells transfected with the vector alone (pECE), with vectors separately expressing P450scc ("scc"), adrenodoxin ("Adx"), adrenodoxin reductase ("AdRed") or P450scc targeted to the endoplasmic reticulum ("ER-scc"), from cells doubly transfected with vectors separately expressing ER-P450scc and P450 oxidoreductase ("ER-scc/OR") or from cells transfected with vectors expressing fusion proteins F1 to F8. Blots were probed with rabbit-anti-human antibodies to P450scc (FIG. 10A), Adx (FIG. 10B), AdRed (FIG. 10C) and OR (FIG. 10D).
Figure 10B:
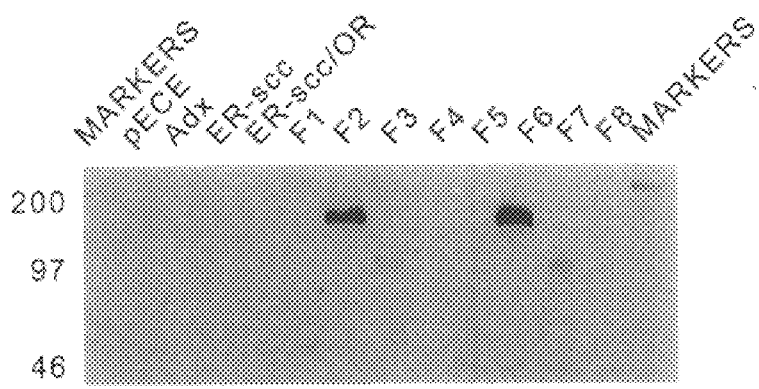
Figure 10C:
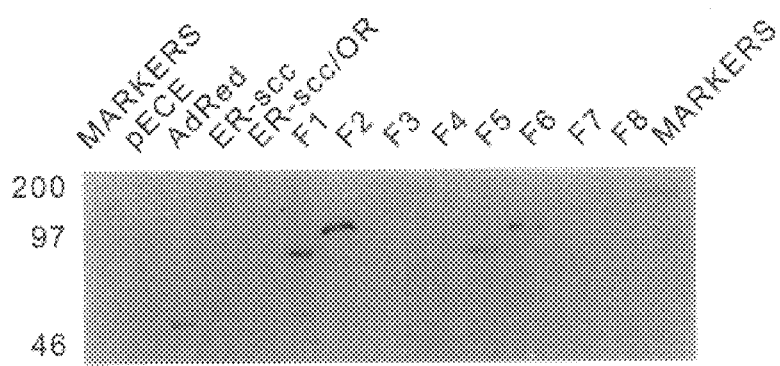
Figure 10D:
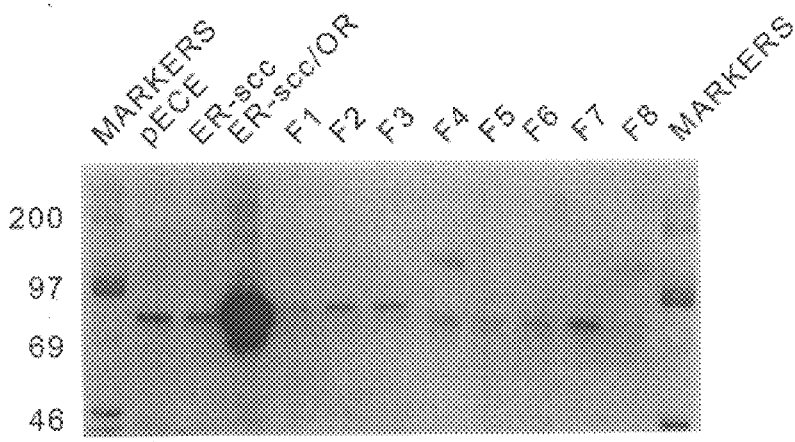

Western blotting of mitochondrial proteins from the various transfections shows that the mRNAs for P450scc, AdRed, F1 and F2 were translated into comparable amounts of stable proteins. The sizes of P450scc, AdRed, F1 and F2 seen on the gel correspond to the predicted sizes (FIG. 8). However, in multiple experiments very little F3 protein was seen. Longer autoradiographic exposures show a band of protein reacting with anti-P450scc antibody having a migration greater than P450scc but less than F1; this apparently represents proteolytic cleavage of the carboxyl-terminal AdRed moiety as the band has the size expected for a P450scc/Adx fusion and fails to react with antisera to AdRed, although it does react with antisera to P450scc and Adx. This may account for the variable results seen with the F3 construction in Table 1 and in FIG. 6a. The experiments in FIGS. 7 and 8 suggest that the F3 mRNA and protein may be unstable. It is formally possible that the variable results with F3 could be due to differences in the transcription of this construct. However, all the constructions described used exactly the same promoter sequences, and these sequences were linked to P450scc by identical sequences in F1, F2, and F3; thus it seems unlikely that F3 is transcribed differently. A more stable derivative of F3 could have substantially greater activity.

EXAMPLE 2

MATERIALS AND METHODS

Construction of P450scc-OR Fusion Plasmids

To test the electron-transport requirements of P450scc and to test whether this enzyme requires the mitochondrial environment, a series of 18 expression vectors were constructed; their encoded proteins are diagrammed in FIG. 4. F1 is H$_3$N-P450scc-AdRed-COOH, F2 is H$_3$N-P450scc-AdRed-Adx-COOH, and F3 is H$_3$N-P450scc-Adx-AdRed-COOH described in Example 1. Protein F4, which is a fusion between P450scc and NADPH-dependent P450 oxidoreductase, was constructed to examine the stringency of P450scc in accepting electrons from the mitochondrial electron transfer system. The cDNA sequence that encodes the first 56 amino acids of OR, which are thought to be involved in the association of OR with the ER membrane (Porter and Kasper 1985), was deleted and replaced with a linker that encodes a unique SpeI site and also encodes the hydrophilic hinge peptide Thr-Asp-Gly-Thr-Ser. Fusions F1 to F4 all possess the 39-residue amino-terminal signal sequence of P450scc, which is responsible for targeting the protein to mitochondria. In the proteins designated ER-P450scc and F5 to F8, these 39 amino acids were replaced by the endoplasmic reticulum insertion/halt-transfer sequence of rat P450IIB1.

The construction of the plasmids expressing Adx and AdRed are described above. To construct fusion protein F4 (H$_3$N-P450scc-OR-COOH), the P450scc moiety was first prepared exactly as described for F1 to F3. The NADPH-dependent P450 oxidoreductase cDNA (Yamano et al. 1989) was modified by PCR to remove its microsomal leader sequence, which consists of the first 56 amino acids (Porter and Kasper 1985). A 418 bp segment from the 5' end of the OR cDNA was amplified using primers #11 (5' GACTAG-TATTCAGACATTGACCTCC 3') (SEQ ID NO: 19) and #12 (5' CAACCCCAGCTCAAAGATGC 3') (SEQ ID NO: 20). Use of primer #11 (SEQ ID NO: 19) removes the leader sequence, adds an SpeI site for cloning, and encodes the hinge sequence Thr-Asp-Gly-Thr-Ser (SEQ ID NO: 9) to allow translation through both the P450scc and OR moieties to produce a fusion enzyme. The downstream primer #12 (SEQ ID NO: 20) was chosen at a naturally occurring NarI site, allowing ligation to the remainder of the OR cDNA.

For the plasmids designated F4 through F8, the mitochondrial targeting sequence encoded by P450scc (amino acids 1–39) was replaced by the endoplasmic reticulum insertion/halt-transfer sequence of rat P450IIB1 (Monier et al. 1988). This was done using upstream oligonucleotide #13 (5' GGGTACCATGGAGCCCAGTATCTTG 3') (SEQ ID NO: 21) and downstream oligonucleotide #14 (5' GACTAA-GAGTAACAAGAAGCC 3') (SEQ ID NO: 22) to prepare a 69 bp fragment encoding the endoplasmic reticulum targeting sequence (the first 23 residues) of rat P450IIB1. Primer #13 (SEQ ID NO: 21) adds a KpnI site for cloning, and primer #14 (SEQ ID NO: 22) generates a blunt-ended site. A similar method was used to remove the mitochondrial targeting sequence from P450scc to yield a blunt-ended fragment. Upstream oligonucleotide #15 (5' ATCTCCAC-CCGCAGTCCTCGC 3') (SEQ ID NO: 23) generated a blunt-ended cDNA fragment beginning at the codon for amino acid 40 of P450scc (SEQ ID NO: 1) (i.e., the first residue of the processed mature intra-mitochondrial protein), and downstream oligonucleotide #16 (5' TTGGGGCCCTCGGACTTAAAG 3') (SEQ ID NO: 24) extended to the ApaI site at codon 140. The two sequences were then ligated together and subcloned into vector pUC-SF (Harikrishna et al. 1993) as described in Example 1. A KpnI/EcoRV fragment was then isolated from this plasmid and used to replace the equivalent sequence in the F1 through F4 vectors. Similarly, the segment encoding the insertion/halt-transfer sequence (amino acids 1–17) of human P450c17 cDNA (Chung et al. 1987) was removed using PCR and replaced with the rat P450IIB1 sequence. All PCR fragments and ligation junctions were sequenced to verify that no errors had occurred in the amplification or subcloning.

For the plasmids F1AR+ and F2AR+ expressing fusion proteins F1AR+ and F2AR+, the common, 18- form of AdRed cDNA was replaced with the alternately spliced 18+ form of AdRed cDNA (Solish et al. 1988; Lin et al. 1990) by substitution into the SpeI/NheI site as described above (see also Harikrishna et al. 1993, which is hereby specifically incorporated by reference). To construct plasmid F2DM which expresses fusion protein F2DM ("DM" stands for double mutation where both AdRed and Adx are mutated), the F2AR+ construction was mutagenized by PCR using upstreamoligo #17 (5' TCTAGATATTGATGGCTTTGGT-GCAT<u>A</u>TGAGGGAACCCTGGCTT<u>A</u>TTCAAC CT<u>A</u>T 3') and downstream oligo #10 (Solish et al. 1988). Oligo #17 creates cysteine to tyrosine mutations at amino acid positions 47, 52 and 55 in the Adx moiety of F2AR+, referred to as mutations C47W, C52W and C55W, by changing three TGT (Cys) codons to TAT (Tyr), thus destroying three of the four cysteines that coordinate the Fe++ ion in Adx (Cupp and Vickery 1988). All PCR fragments and ligation junctions were sequenced to verify that no errors had occurred in the amplification or subcloning.

Transfection of COS-1 Cells

COS-1 cells were transfected using either a calcium chloride method or DEAE-Dextran method. Plasmid DNA purified by cesium chloride density gradients (>95% supercoiled) was used for each transfection. Each 10 cm dish (Falcon) received 2 pmol of vector plasmid and 5 μg of an RSV-LUC plasmid to control for transfection efficiency. After transfections were carried out on cultures at 60% confluency for 16 h at 37° C. in 5% $CO_2$, the medium was replaced with fresh DME-H21 containing 4.5 g/l glucose, 10% fetal calf serum and 50 μg/ml gentamicin. After 48 h of transfection, the medium was removed from the cells and replaced with a depleted medium containing only 0.5% fetal calf serum but supplemented with $5 \times 10^{-6}$ M 22R-hydroxycholesterol. 24 h later, cells were harvested for luciferase activity measurement, and pregnenolone in the medium was measured by RIA as discussed above. (Black et al. 1993).

RNA and Protein Analysis 48 h after transfection, cells were washed twice in phosphate buffered saline (PBS) and harvested with either 8 M guanidinium-HCl for RNA preparation or into sucrose buffer (0.25 M sucrose, 50 mM ethanolamine, 10 mM Tris-HCl pH 7.4, 1 mM EDTA) for protein analysis. Northern analysis of RNA was done using MOPS-formaldehyde denaturing gels and $^{32}$P-labeled EcoRI-fragments from human cDNA clones containing P450scc (Chung et al. 1986), Adx (Picado-Leonard et al. 1988), AdRed (Solish et al. 1988) and OR (Yamano et al. 1989) as probe. Total protein content was determined after cell disruption with two 5 sec bursts using a sonicator (Artek Systems Corp.) at a setting of 20, and an equal volume of 2x loading buffer (50 mM Tris-HCl pH 6.8, 2% $NaDodSO_4$, 5% β-mercaptoetanol, 10% glycerol, 0.005% bromophenol blue) was added. Samples were boiled for 5 min and then separated by electrophoresis on $NaDodSO_4$, 4–20% acrylamide gradient gels. The proteins were then electro-transferred to nitrocellulose in Tris-HCl pH 8.4, 193 mM glycine, 20% methanol for 1 h at 4° C., and immunoblotting was done using antisera specific to human P450scc, Adx, AdRed (Black et al. 1993), P450c17 (Lin et al. 1993), and OR (a generous gift from C. R. Wolf) as described (Black et al. 1993).

RESULTS

Transcription of the cDNA Expression Vectors

To examine the expression of the various cDNA expression constructions, RNA from transfected COS-1 cells was prepared and analyzed by Northern blotting with probes for P450scc, Adx, AdRed, and OR (FIG. 9). All of the vectors expressed RNAs of the predicted sizes that contained hybridizing sequences predicted by their designs. The vector expressing ER-P450scc, either when transferred alone or when co-transfected with a vector expressing OR, expressed less mRNA than the corresponding normal P450scc vector with a mitochondrial leader sequence, either when it was transfected alone or triply transfected with vectors separately expressing AdRed and Adx. The reason for this is unclear. The abundances of the mRNAs produced by vectors F5 through F8 encoding microsomal proteins are very similar to the abundances of the mRNAs produced by the corresponding vectors F1 through F4, which express mitochondrial proteins. Thus, the presence of the leader sequence from rat P450IIB1 and the junction between this leader and P450scc cannot be responsible for the poor expression (or poor mRNA stability) of the ER-P450scc construction. When the same Northern blot is reprobed with cDNAs for human Adx (FIG. 9B), AdRed (FIG. 9C) and OR (FIG. 9D), only the constructions predicted to encode these RNA segments are detected, and the sizes of the hybridizing bands on these different probings of the same gel correspond precisely. Although Adx (Picado-Leonard et al. 1988) and AdRed (Brentano et al. 1992) are expressed in all tissues, the endogenous level of expression of these mRNAs in COS-1 cells is below the level of detection on this Northern blot. By contrast, endogenous COS-1 cell OR mRNA is seen in all lanes (FIG. 9D).

Expression of Fusion Proteins

To examine the translation of the mRNAs encoded by the expression vectors shown in FIG. 4, total protein from cells transfected with each of the fusion constructions was isolated and analyzed by Western blotting with antibodies to human P450scc, Adx, AdRed, and OR (FIG. 10). The fusion proteins react with the expected antisera: F1 and F5 react with antibodies to P450scc and AdRed but not with antibodies to Adx or OR; F2 and F6 react with antisera to P450scc, AdRed and Adx, but not with antisera or OR; and F4 and F8 react with antisera to P450scc and OR but not with antisera to AdRed or Adx. Proteins encoded by the F3 and F7 constructions, which should be the same size as the F2 and F6 proteins, could not be detected with the P450scc or AdRed antibodies. However, a smaller (~100 k Dalton) band is detected with the Adx antibody, suggesting lability due to a proteolytic cleavage. With both F3 and F7, this same band can be detected with the P450scc antibody, suggesting that there is a proteolytic cleavage that removes and degrades the AdRed moiety. The amount of protein produced by the constructions that target proteins to the endoplasmic reticulum is generally lower than the amount of the corresponding protein targeted to the mitochondria, even after normalization for differences in transfection efficiency. This may be due to an inherent instability in the proteins caused by the presence in a cellular compartment where they are not normally found.

Enzymatic Activities of Fusion Proteins

Figure 11:
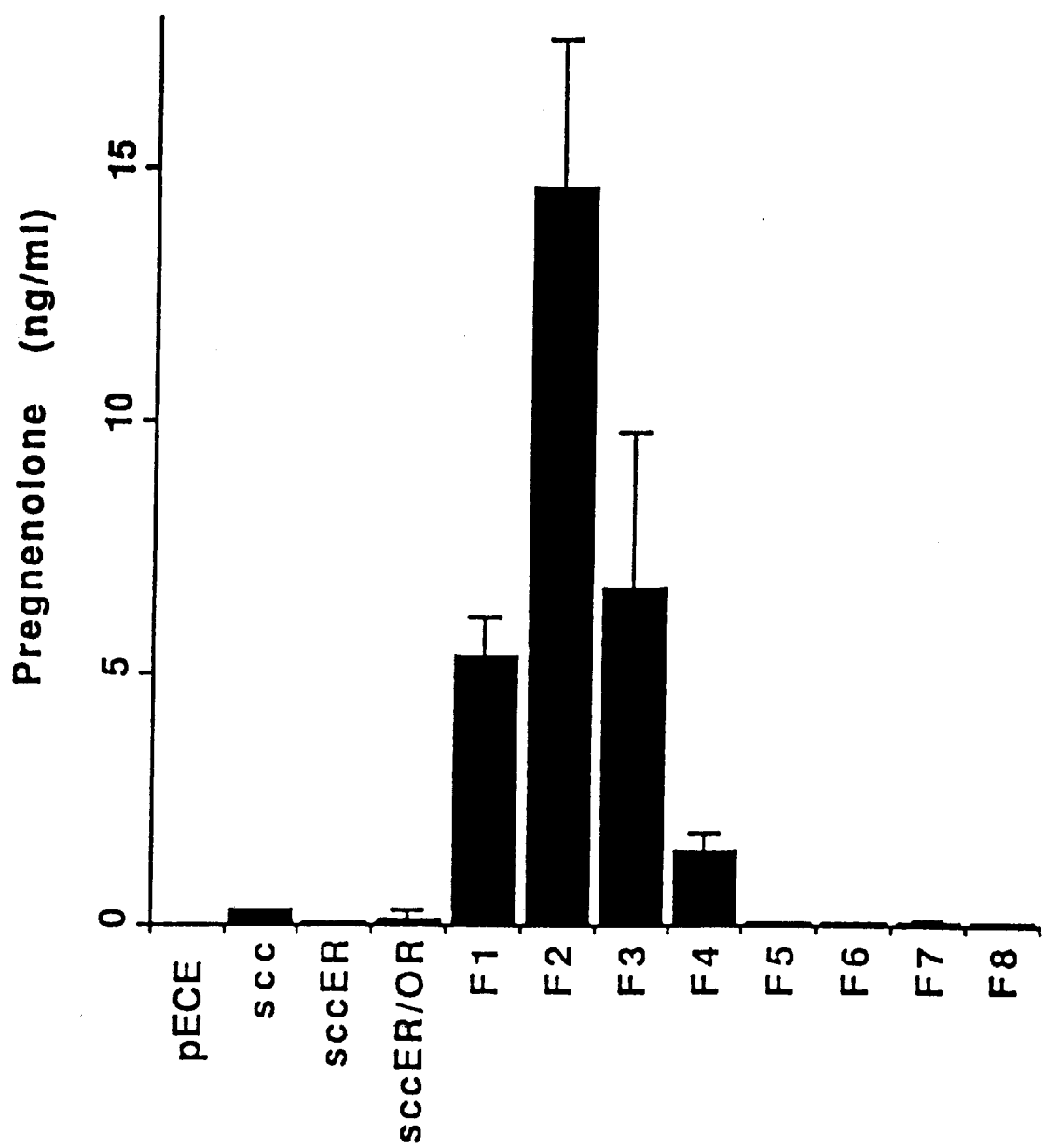
FIG. 11 is a schematic depicting the biological activity of the fusion proteins. Conversion of 22-hydroxycholesterol to pregnenolone was measured by RIA and is displayed as ng pregnenolone per ml of culture medium, corrected for transfection efficiency (FIG. 11). "N.D." signifies Not Detectable. COS-1 cells transfected with various expression vectors are designated as in FIGS. 9A–D and 10A–D.

The enzymatic activity of each fusion protein was measured by the abilities of the corresponding transfected cells to convert 22-R hydroxycholesterol to pregnenolone (FIG. 11). 22-R hydroxycholesterol was chosen as a substrate because it is soluble and freely diffusible in the cell so that it is equally accessible to enzymes in the endoplasmic reticulum and the mitochondria. Only those proteins expressed in the mitochondria exhibit detectable enzymatic activity, while those expressed in the endoplasmic reticulum show no appreciable ability to convert 22-hydroxycholesterol to pregnenolone. Thus it appears that the mitochondrial (reducing) environment is required for P450scc activity.

The four-fold increase in pregnenolone produced by F4 compared to P450scc alone shows that P450scc can receive electrons from OR as well as from AdRed. Thus, the ability of F1 through F4 to convert cholesterol to pregnenolone shows that P450scc can accept electrons from a variety of electron-transfer proteins. However, the lower activity of F4 suggests there may be some structural bias for the natural electron donor.

Replacement of the active, 18- form of AdRed in F1 with the alternately spliced, 18+ form of AdRed, as described above, resulted in fusion protein F1AR+ that had only modestly reduced activity. Similarly when the 18- form of AdRed in F2 was replaced with the 18+ form, the activity of F2AR+ was unchanged. In contrast it has been reported that the 18+ form of AdRed is inactive in assays in vitro (Brandt and Vickery 1992; Lin et al. 1990). The F2DM fusion protein expressed from construct F2DM, in which three of the four Cys residues that coordinate the Fe++ ion of Adx were mutated, was completely inactive. These results confirm that the P450scc moiety of F2 (or of F2AR+) is catalytically active by receiving its electrons from the covalently linked Adx moiety and not from interaction with endogenous cellular Adx. Although the invention is not to be limited by any mechanism of action proposed herein, these results are consistent with the teaching that F1 and F4 constructions are catalytically active by receiving electrons from their covalently linked AdRed or OR moieties, rather than from endogenous COS-1 cell Adx, and support the teaching herein that P450scc can have a rather broad range of acceptable electron donors.

Testing the Function of the Rat P450IIB1 Leader Sequence

Figure 12A:
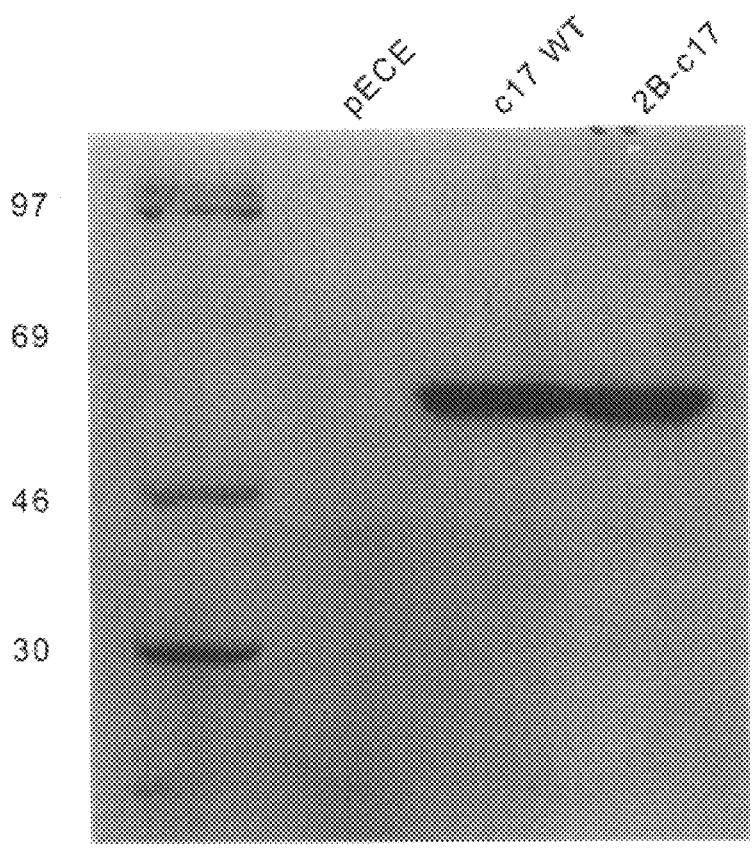
FIGS. 12A and 12B depict targeting of a protein to the endoplasmic reticulum by the P450IIB1 leader sequence.
Figure 12B:
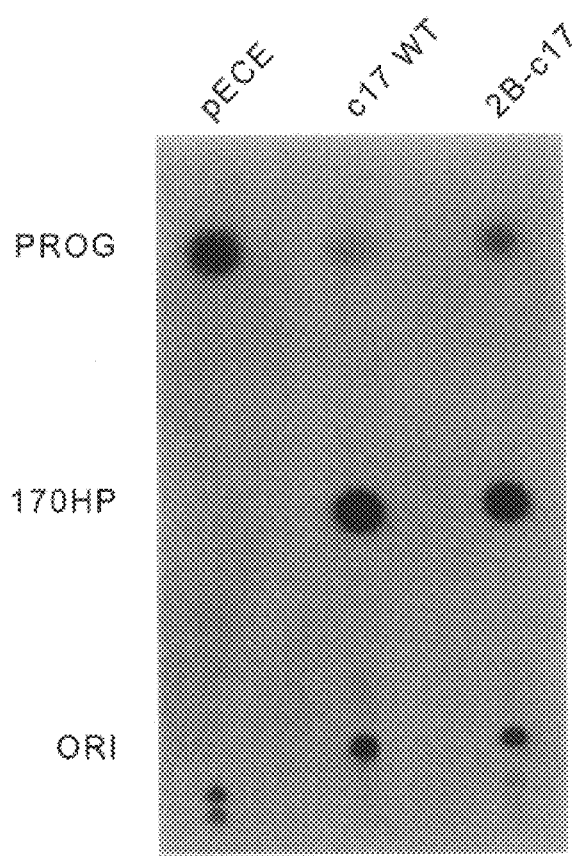

Since all the constructions containing the insertion/halt-transfer sequence of rat P450IIB1 failed to produce active proteins, whether this leader sequence might somehow be unsuitable for steroidogenic P450 enzymes was determined by testing the suitability of using this leader to target P450c17, another steroidogenic P450 enzyme that is normally found in the endoplasmic reticulum (FIG. 12). P450c17 activity is easily assayed (Lin et al. 1993; Lin et al. 1991 *J. Biol. Chem*), and removal of its targeting sequence results in a cystolic form of the protein that is enzymatically inactive and rapidly degraded (Clark and Waterman 1991).

pECE vectors expressing P450c17 wild type with its own leader sequence (c17WT), or P450c17 with the leader sequence from P450IIB1 (2B-c17) encode proteins that specifically cross-react with the P450c17 antiserum (FIG. 12A). The intensity of each is similar, indicating that each protein is produced in similar amounts after transfection, and that both proteins are stable. To determine if P450c17 containing the P405IIB1 leader is enzymatically active, the ability of the 2B-c17 protein to catalyze the conversion of pregnenolone to 17-hydroxypregnenolone was measured (FIG. 12B). COS-1 cells transfected with the pECE vector cannot convert pregnenolone to 17 hydroxypregnenolone while c17WT and 2B-c17 exhibit comparable levels of 17α-hydroxylase activity. Thus the rat P450IIB1 insertion/halt-transfer sequence can localize steroidogenic cytochrome P450 enzymes to the endoplasmic reticulum in a functional manner.

Subcellular targeting was further examined by preparing cytosol, mitochondria and endoplasmic reticulum from cells transfected with plasmids F2, F6 and the pECE vector. Western blotting with antiserum to the Adx showed the expected F2 protein band in the mitochondria of cells transfected with plasmid F2, but no F2 protein in the cytosol or endoplasmic reticulum. Similarly the F6 protein was found only in the endoplasmic reticulum, but not in the cytosol or mitochondria. The mitochondrial leader from P450scc and the endoplasmic reticulum leader from P450IIHB1 correctly target fusion proteins to the predicted cellular organelles.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A polynucleotide sequence encoding a fusion enzyme, having an N-terminal and a C-terminal end, comprising (1) P450scc or a fragment thereof retaining cholesterol-side-chain-cleavage activity and (2) an electron-transfer protein having the ability to transfer electrons to said p450ssc.

2. The polynucleotide sequence of claim 1, wherein the electron-transfer protein is selected from the group consisting of adrenodoxin reductase, adrenodoxin, P450 oxidoreductase, cytochrome b5, and fragments thereof retaining ability to transfer electrons to said p450ssc.

3. The polynucleotide sequence of claim 1, wherein the sequence encoding P450scc has at least 90% sequence identity with the sequence encoding amino acids 40 to 521 of human P450scc (SEQ ID NO: 1) set forth in FIG. 1 and encodes a polypeptide having P450 side chain cleaving activity.

4. The polynucleotide sequence of claim 3, wherein the P450scc is encoded by the sequence of human P450scc (SEQ ID NO: 1) set forth in FIG. 1.

5. The polynucleotide sequence of claim 2, wherein the adrenodoxin reductase has at least 90% sequence identity with the amino acid sequence of human adrenodoxin reductase (SEQ ID NO: 3) from amino acids 33 to 497, excluding amino acids 204 to 209, set forth in FIG. 2.

6. The polynucleotide sequence of claim 5, wherein the adrenodoxin reductase is encoded by the sequence of human adrenodoxin reductase (SEQ ID NO: 3) excluding the sequence encoding amino acids 204 to 209 set forth in FIG. 2.

7. The polynucleotide sequence of claim 2, wherein the sequence encoding adrenodoxin has at least 90% sequence identity with the sequence (SEQ ID NO: 5) encoding amino acids 57 to 170 set forth in FIG. 3 and encodes a polypeptide having adrenodoxin electron-transfer activity.

8. The polynucleotide sequence of claim 7, wherein sequence encoding adrenodoxin is identical to the sequence encoding human adrenodoxin (SEQ ID NO: 5) from amino acid 57 to 170 set forth in FIG. 3.

9. The polynucleotide sequence of claim 2, wherein the protein sequences are comprised of sequences from bovine sources.

10. The polynucleotide sequence of claim 1, which further comprises a sequence encoding a linking peptide that links said P450scc or a fragment thereof retaining cholesterol-side-chain-cleaving activity to the electron-transfer protein.

11. The polynucleotide sequence of claim 2, wherein the electron-transfer protein comprises (1) adrenodoxin or a fragment thereof and (2) adrenodoxin reductase or a fragment thereof.

12. The polynucleotide sequence of claim 1, wherein P450scc or a fragment thereof retaining cholesterol-side-chain-cleaving activity is at the N-terminal end.

13. The polynucleotide sequence of claim 1, which further comprises a sequence encoding a signal peptide fused to the N-terminal of the fusion enzyme.

14. The polynucleotide sequence of claim 13, wherein the signal peptide is a mitochondrial-targeting signal peptide.

15. The polynucleotide sequence of claim 2, wherein adrenodoxin or a format thereof is at the C-terminal end.

16. The polynucleotide sequence of claim 10, wherein a linking peptide links said P450scc or a fragment thereof retaining cholesterol-side-chain-cleaving activity to adrenodoxin or a fragment thereof or to adrenodoxin reductase or a fragment thereof, or wherein a linking peptide links adrenodoxin or a fragment thereof to adrenodoxin reductase or a fragment thereof.

17. The polynucleotide sequence of claim 16, wherein any one or more of the linking peptides are Thr-Asp-Gly-Thr-Ser (SEQ ID NO: 9) or Thr-Asp-Gly-Ala-Ser (SEQ ID NO: 10).

18. The polynucleotide sequence of claim 11, wherein said sequence contains at least one codon different from a corresponding codon in a naturally occurring sequence.

19. A functional polynucleotide construct comprising (a) a transcription initiation region functional in a unicellular organism, (b) a polynucleotide sequence of claim 1, and (c) a transcription termination region, wherein expression of said construct in said unicellular organism results in production of the fusion enzyme encoded by said polynucleotide sequence.

20. The functional polynucleotide construct of claim 19, selected from plasmids F1, F2, F3, F4, F1AR+, and F2AR+.

21. The functional polynucleotide construct of claim 19 which further comprises an intron.

22. A procaryotic or eukaryotic host cell comprising a polynucleotide construct of claim 19.

* * * * *

SEQUENCE LISTING (1) GENERAL INFORMATION:

(iii) NUMBER OF SEQUENCES: 24

(2) INFORMATION FOR SEQ ID NO:1:

(i) SEQUENCE CHARACTERISTICS:
      (A) LENGTH: 1839 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (ix) FEATURE:
      (A) NAME/KEY: CDS
      (B) LOCATION: 45..1607

(xi) SEQUENCE DESCRIPTION: SEQ ID NO:1:

```
GGGCGCTGAA GTGGAGCAGG TACAGTCACA GCTGTGGGGA CAGC ATG CTG GCC AAG      56
                                              Met Leu Ala Lys
```

-continued

1

| | |
|---|---|
| GGT CTT CCC CCA CGC TCA GTC CTG GTC AAA GGC TAC CAG ACC TTT CTG<br>Gly Leu Pro Pro Arg Ser Val Leu Val Lys Gly Tyr Gln Thr Phe Leu<br>5                     10                     15                     20 | 104 |
| AGT GCC CCC AGG GAG GGG CTG GGG CGT CTC AGG GTG CCC ACT GGC GAG<br>Ser Ala Pro Arg Glu Gly Leu Gly Arg Leu Arg Val Pro Thr Gly Glu<br>                       25                     30                     35 | 152 |
| GGA GCT GGC ATC TCC ACC CGC AGT CCT CGC CCC TTC AAT GAG ATC CCC<br>Gly Ala Gly Ile Ser Thr Arg Ser Pro Arg Pro Phe Asn Glu Ile Pro<br>                 40                     45                     50 | 200 |
| TCT CCT GGT GAC AAT GGC TGG CTA AAC CTG TAC CAT TTC TGG AGG GAG<br>Ser Pro Gly Asp Asn Gly Trp Leu Asn Leu Tyr His Phe Trp Arg Glu<br>         55                     60                     65 | 248 |
| ACG GGC ACA CAC AAA GTC CAC CTT CAC CAT GTC CAG AAT TTC CAG AAG<br>Thr Gly Thr His Lys Val His Leu His His Val Gln Asn Phe Gln Lys<br>70                     75                     80 | 296 |
| TAT GGC CCG ATT TAC AGG GAG AAG CTC GGC AAC GTG GAG TCG GTT TAT<br>Tyr Gly Pro Ile Tyr Arg Glu Lys Leu Gly Asn Val Glu Ser Val Tyr<br>85                     90                     95                 100 | 344 |
| GTC ATC GAC CCT GAA GAT GTG GCC CTT CTC TTT AAG TCC GAG GGC CCC<br>Val Ile Asp Pro Glu Asp Val Ala Leu Leu Phe Lys Ser Glu Gly Pro<br>                     105                 110                 115 | 392 |
| AAC CCA GAA CGA TTC CTC ATC CCG CCC TGG GTC GCC TAT CAC CAG TAT<br>Asn Pro Glu Arg Phe Leu Ile Pro Pro Trp Val Ala Tyr His Gln Tyr<br>         120                     125                     130 | 440 |
| TAC CAG AGA CCC ATA GGA GTC CTG TTG AAG AAG TCG GCA GCC TGG AAG<br>Tyr Gln Arg Pro Ile Gly Val Leu Leu Lys Lys Ser Ala Ala Trp Lys<br>                 135                 140                 145 | 488 |
| AAA GAC CGG GTG GCC CTG AAC CAG GAG GTG ATG GCT CCA GAG GCC ACC<br>Lys Asp Arg Val Ala Leu Asn Gln Glu Val Met Ala Pro Glu Ala Thr<br>150                     155                     160 | 536 |
| AAG AAC TTT TTG CCC CTG TTG GAT GCA GTG TCT CGG GAC TTC GTC AGT<br>Lys Asn Phe Leu Pro Leu Leu Asp Ala Val Ser Arg Asp Phe Val Ser<br>165                     170                 175                 180 | 584 |
| GTC CTG CAC AGG CGC ATC AAG AAG GCG GGC TCC GGA AAT TAC TCG GGG<br>Val Leu His Arg Arg Ile Lys Lys Ala Gly Ser Gly Asn Tyr Ser Gly<br>                     185                 190                 195 | 632 |
| GAC ATC AGT GAT GAC CTG TTC CGC TTT GCC TTT GAG TCC ATC ACT AAC<br>Asp Ile Ser Asp Asp Leu Phe Arg Phe Ala Phe Glu Ser Ile Thr Asn<br>         200                     205                     210 | 680 |
| GTC ATT TTT GGG GAG CGC CAG GGG ATG CTG GAG GAA CTA CTG AAC CCC<br>Val Ile Phe Gly Glu Arg Gln Gly Met Leu Glu Glu Val Val Asn Pro<br>                 215                 220                 225 | 728 |
| GAG GCC CAG CGA TTC ATT GAT GCC ATC TAC CAG ATG TTC CAC ACC AGC<br>Glu Ala Gln Arg Phe Ile Asp Ala Ile Tyr Gln Met Phe His Thr Ser<br>230                     235                     240 | 776 |
| GTC CCC ATG CTC AAC CTT CCC CCA GAC CTG TTC CGT CTG TTC AGG ACC<br>Val Pro Met Leu Asn Leu Pro Pro Asp Leu Phe Arg Leu Phe Arg Thr<br>245                     250                 255                 260 | 824 |
| AAG ACC TGG AAG GAC CAT GTG GCT GCA TGG GAC GTG ATT TTC AGT AAA<br>Lys Thr Trp Lys Asp His Val Ala Ala Trp Asp Val Ile Phe Ser Lys<br>                 265                 270                 275 | 872 |
| GCT GAC ATA TAC ACC CAG AAC TTC TAC TGG GAA TTG AGA CAG AAA GGA<br>Ala Asp Ile Tyr Thr Gln Asn Phe Tyr Trp Glu Leu Arg Gln Lys Gly<br>         280                     285                     290 | 920 |
| AGT GTT CAC CAC GAT TAC CGT GGC ATG CTC TAC AGA CTC CTG GGA GAC<br>Ser Val His His Asp Tyr Arg Gly Met Leu Tyr Arg Leu Leu Gly Asp<br>                 295                 300                 305 | 968 |
| AGC AAG ATG TCC TTC GAG GAC ATC AAG GCC AAC GTC ACA GAG ATG CTG<br>Ser Lys Met Ser Phe Glu Asp Ile Lys Ala Asn Val Thr Glu Met Leu | 1016 |

-continued

```
           310                 315                 320
GCA GGA GGG GTG GAC ACG ACG TCC ATG ACC CTG CAG TGG CAC TTG TAT    1064
Ala Gly Gly Val Asp Thr Thr Ser Met Thr Leu Gln Trp His Leu Tyr
325                 330                 335                 340

GAG ATG GCA CGC AAC CTG AAG GTG CAG GAT ATG CTG CGG GCA GAG GTC    1112
Glu Met Ala Arg Asn Leu Lys Val Gln Asp Met Leu Arg Ala Glu Val
                345                 350                 355

TTG GCT GCG CGG CAC CAG GCC CAG GGA GAC ATG GCC ACG ATG CTA CAG    1160
Leu Ala Ala Arg His Gln Ala Gln Gly Asp Met Ala Thr Met Leu Gln
            360                 365                 370

CTG GTC CCC CTC CTC AAA GCC AGC ATC AAG GAG ACA CTA AGA CTT CAC    1208
Leu Val Pro Leu Leu Lys Ala Ser Ile Lys Glu Thr Leu Arg Leu His
        375                 380                 385

CCC ATC TCC GTG ACC CTG CAG AGA TAT CTT GTA AAT GAC TTG GTT CTT    1256
Pro Ile Ser Val Thr Leu Gln Arg Tyr Leu Val Asn Asp Leu Val Leu
    390                 395                 400

CGA GAT TAC ATG ATT CCT GCC AAG ACA CTG GTG CAA GTG GCC ATC TAT    1304
Arg Asp Tyr Met Ile Pro Ala Lys Thr Leu Val Gln Val Ala Ile Tyr
405                 410                 415                 420

GCT CTG GGC CGA GAG CCC ACC TTC TTC TTC GAC CCG GAA AAT TTT GAC    1352
Ala Leu Gly Arg Glu Pro Thr Phe Phe Phe Asp Pro Glu Asn Phe Asp
                425                 430                 435

CCA ACC CGA TGG CTG AGC AAA GAC AAG AAC ATC ACC TAC TTC CGG AAC    1400
Pro Thr Arg Trp Leu Ser Lys Asp Lys Asn Ile Thr Tyr Phe Arg Asn
            440                 445                 450

TTG GGC TTT GGC TGG GGT GTG CGG CAG TGT CTG GGA CGG CGG ATC GCT    1448
Leu Gly Phe Gly Trp Gly Val Arg Gln Cys Leu Gly Arg Arg Ile Ala
        455                 460                 465

GAG CTA GAG ATG ACC ATC TTC CTC ATC AAT ATG CTG GAG AAC TTC AGA    1496
Glu Leu Glu Met Thr Ile Phe Leu Ile Asn Met Leu Glu Asn Phe Arg
    470                 475                 480

GTT GAA ATC CAA CAC CTC AGC GAT GTG GGC ACC ACA TTC AAC CTC ATT    1544
Val Glu Ile Gln His Leu Ser Asp Val Gly Thr Thr Phe Asn Leu Ile
485                 490                 495                 500

CTG ATG CCT GAA AAG CCC ATC TCC TTC ACC TTC TGG CCC TTT AAC CAG    1592
Leu Met Pro Glu Lys Pro Ile Ser Phe Thr Phe Trp Pro Phe Asn Gln
                505                 510                 515

GAA GCA ACC CAG CAG TGATCAGAGA GGATGGCCTG CAGCCACATG GGAGGAAGGC    1647
Glu Ala Thr Gln Gln
            520

CCAGGGGTGG GGCCCATGGG GTCTCTGCAT CTTCAGTCGT CTGTCCCAAG TCCTGCTCCT   1707

TTCTGCCCAG CCTGCTCAGC AGGTTGAATG GGTTCTCAGT GGTCACCTTC CTCAGCTCAG   1767

CTGGGCCACT CCTCTTCACC CACCCCATGG AGACAATAAA CAGCTGAACC ATCGAAAAAA   1827

AAAAAAAAAA AA                                                       1839
```

(2) INFORMATION FOR SEQ ID NO:2:

(i) SEQUENCE CHARACTERISTICS:
        (A) LENGTH: 521 amino acids
        (B) TYPE: amino acid
        (D) TOPOLOGY: linear (ii) MOLECULE TYPE: protein (xi) SEQUENCE DESCRIPTION: SEQ ID NO:2:

```
Met Leu Ala Lys Gly Leu Pro Pro Arg Ser Val Leu Val Lys Gly Tyr
 1               5                  10                  15

Gln Thr Phe Leu Ser Ala Pro Arg Glu Gly Leu Gly Arg Leu Arg Val
             20                  25                  30
```

-continued

```
Pro Thr Gly Glu Gly Ala Gly Ile Ser Thr Arg Ser Pro Arg Pro Phe
            35                  40                  45
Asn Glu Ile Pro Ser Pro Gly Asp Asn Gly Trp Leu Asn Leu Tyr His
     50                  55                  60
Phe Trp Arg Glu Thr Gly Thr His Lys Val His Leu His His Val Gln
 65                  70                  75                  80
Asn Phe Gln Lys Tyr Gly Pro Ile Tyr Arg Glu Lys Leu Gly Asn Val
                 85                  90                  95
Glu Ser Val Tyr Val Ile Asp Pro Glu Asp Val Ala Leu Leu Phe Lys
                100                 105                 110
Ser Glu Gly Pro Asn Pro Glu Arg Phe Leu Ile Pro Pro Trp Val Ala
            115                 120                 125
Tyr His Gln Tyr Gln Arg Pro Ile Gly Val Leu Leu Lys Lys Ser
        130                 135                 140
Ala Ala Trp Lys Lys Asp Arg Val Ala Leu Asn Gln Glu Val Met Ala
145                 150                 155                 160
Pro Glu Ala Thr Lys Asn Phe Leu Pro Leu Leu Asp Ala Val Ser Arg
                165                 170                 175
Asp Phe Val Ser Val Leu His Arg Arg Ile Lys Lys Ala Gly Ser Gly
                180                 185                 190
Asn Tyr Ser Gly Asp Ile Ser Asp Leu Phe Arg Phe Ala Phe Glu
        195                 200                 205
Ser Ile Thr Asn Val Ile Phe Gly Glu Arg Gln Gly Met Leu Glu Glu
210                 215                 220
Val Val Asn Pro Glu Ala Gln Arg Phe Ile Asp Ala Ile Tyr Gln Met
225                 230                 235                 240
Phe His Thr Ser Val Pro Met Leu Asn Leu Pro Pro Asp Leu Phe Arg
                245                 250                 255
Leu Phe Arg Thr Lys Thr Trp Lys Asp His Val Ala Ala Trp Asp Val
            260                 265                 270
Ile Phe Ser Lys Ala Asp Ile Tyr Thr Gln Asn Phe Tyr Trp Glu Leu
        275                 280                 285
Arg Gln Lys Gly Ser Val His His Asp Tyr Arg Gly Met Leu Tyr Arg
290                 295                 300
Leu Leu Gly Asp Ser Lys Met Ser Phe Glu Asp Ile Lys Ala Asn Val
305                 310                 315                 320
Thr Glu Met Leu Ala Gly Gly Val Asp Thr Thr Ser Met Thr Leu Gln
                325                 330                 335
Trp His Leu Tyr Glu Met Ala Arg Asn Leu Lys Val Gln Asp Met Leu
            340                 345                 350
Arg Ala Glu Val Leu Ala Ala Arg His Gln Ala Gln Gly Asp Met Ala
        355                 360                 365
Thr Met Leu Gln Leu Val Pro Leu Leu Lys Ala Ser Ile Lys Glu Thr
370                 375                 380
Leu Arg Leu His Pro Ile Ser Val Thr Leu Gln Arg Tyr Leu Val Asn
385                 390                 395                 400
Asp Leu Val Leu Arg Asp Tyr Met Ile Pro Ala Lys Thr Leu Val Gln
                405                 410                 415
Val Ala Ile Tyr Ala Leu Gly Arg Glu Pro Thr Phe Phe Asp Pro
        420                 425                 430
Glu Asn Phe Asp Pro Thr Arg Trp Leu Ser Lys Asp Lys Asn Ile Thr
            435                 440                 445
Tyr Phe Arg Asn Leu Gly Phe Gly Trp Gly Val Arg Gln Cys Leu Gly
450                 455                 460
```

```
Arg Arg Ile Ala Glu Leu Glu Met Thr Ile Phe Leu Ile Asn Met Leu
465                 470                 475                 480

Glu Asn Phe Arg Val Glu Ile Gln His Leu Ser Asp Val Gly Thr Thr
                485                 490                 495

Phe Asn Leu Ile Leu Met Pro Glu Lys Pro Ile Ser Phe Thr Phe Trp
            500                 505                 510

Pro Phe Asn Gln Glu Ala Thr Gln Gln
            515                 520
```

(2) INFORMATION FOR SEQ ID NO:3:

(i) SEQUENCE CHARACTERISTICS:
        (A) LENGTH: 1848 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 21..1511

(xi) SEQUENCE DESCRIPTION: SEQ ID NO:3:

```
GGGGGTTGCT GCTCCCAGCC ATG GCT TCG CGC TGC TGG CGC TGG TGG GGC          50
                     Met Ala Ser Arg Cys Trp Arg Trp Trp Gly
                      1               5                  10

TGG TCG GCG TGG CCT CGG ACC CGG CTG CCT CCC GCC GGG AGC ACC CCG        98
Trp Ser Ala Trp Pro Arg Thr Arg Leu Pro Pro Ala Gly Ser Thr Pro
                15                  20                  25

AGC TTC TGC CAC CAT TTC TCC ACA CAG GAG AAG ACC CCC CAG ATC TGT       146
Ser Phe Cys His His Phe Ser Thr Gln Glu Lys Thr Pro Gln Ile Cys
            30                  35                  40

GTG GTG GGC AGT GGC CCA GCT GGC TTC TAC ACG GCC CAA CAC CTG CTA       194
Val Val Gly Ser Gly Pro Ala Gly Phe Tyr Thr Ala Gln His Leu Leu
        45                  50                  55

AAG CAC CCC CAG GCC CAC GTG GAC ATC TAC GAG AAA CAG CCT GTG CCC       242
Lys His Pro Gln Ala His Val Asp Ile Tyr Glu Lys Gln Pro Val Pro
    60                  65                  70

TTT GGC CTG GTG CGC TTT GGT GTG GCG CCT GAT CAC CCC GAG GTG AAG       290
Phe Gly Leu Val Arg Phe Gly Val Ala Pro Asp His Pro Glu Val Lys
75                  80                  85                  90

AAT GTC ATC AAC ACA TTT ACC CAG ACG GCC CAT TCT GGC CGC TGT GCC       338
Asn Val Ile Asn Thr Phe Thr Gln Thr Ala His Ser Gly Arg Cys Ala
                95                 100                 105

TTC TGG GGC AAC GTG GAG GTG GGC AGG GAC GTG ACG GTG CCG GAG CTG       386
Phe Trp Gly Asn Val Glu Val Gly Arg Asp Val Thr Val Pro Glu Leu
            110                 115                 120

CAG GAG GCC TAC CAC GCT GTG GTG CTG AGC TAC GGG GCA GAG GAC CAT       434
Gln Glu Ala Tyr His Ala Val Val Leu Ser Tyr Gly Ala Glu Asp His
        125                 130                 135

CGG GCC CTG GAA ATT CCT GGT GAG GAG CTG CCA GGT GTG TGC TCC GCC       482
Arg Ala Leu Glu Ile Pro Gly Glu Glu Leu Pro Gly Val Cys Ser Ala
    140                 145                 150

CGG GCC TTC GTG GGC TGG TAC AAC GGG CTT CCT GAG AAC CAG GAG CTG       530
Arg Ala Phe Val Gly Trp Tyr Asn Gly Leu Pro Glu Asn Gln Glu Leu
155                 160                 165                 170

GAG CCA GAC CTG AGC TGT GAC ACA GCC GTG ATT CTG GGG CAG GGG AAC       578
Glu Pro Asp Leu Ser Cys Asp Thr Ala Val Ile Leu Gly Gln Gly Asn
```

```
                        175                 180                     185
GTG GCT CTG GAC GTG GCC CGC ATC CTA CTG ACC CCA CCT GAG CAC CTG          626
Val Ala Leu Asp Val Ala Arg Ile Leu Leu Thr Pro Pro Glu His Leu
                190                 195                 200

GAG GCC CTC CTT TTG TGC CAG AGA ACG GAC ATC ACG AAG GCA GCC CTG          674
Glu Ala Leu Leu Leu Cys Gln Arg Thr Asp Ile Thr Lys Ala Ala Leu
                205                 210                 215

GGT GTA CTG AGG CAG AGT CGA GTG AAG ACA GTG TGG CTA GTG GGC CGG          722
Gly Val Leu Arg Gln Ser Arg Val Lys Thr Val Trp Leu Val Gly Arg
                220                 225                 230

CGT GGA CCC CTG CAA GTG GCC TTC ACC ATT AAG GAG CTT CGG GAG ATG          770
Arg Gly Pro Leu Gln Val Ala Phe Thr Ile Lys Glu Leu Arg Glu Met
235                 240                 245                 250

ATT CAG TTA CCG GGA GCC CGG CCC ATT TTG GAT CCT GTG GAT TTC TTG          818
Ile Gln Leu Pro Gly Ala Arg Pro Ile Leu Asp Pro Val Asp Phe Leu
                255                 260                 265

GGT CTC CAG GAC AAG ATC AAG GAG GTC CCC CGC CCG AGG AAG CGG CTG          866
Gly Leu Gln Asp Lys Ile Lys Glu Val Pro Arg Pro Arg Lys Arg Leu
                270                 275                 280

ACG GAA CTG CTG CTT CGA ACG GCC ACA GAG AAG CCA GGG CCG GCG GAA          914
Thr Glu Leu Leu Leu Arg Thr Ala Thr Glu Lys Pro Gly Pro Ala Glu
                285                 290                 295

GCT GCC CGC CAG GCA TCG GCC TCC CGT GCC TGG GGC CTC CGC TTT TTC          962
Ala Ala Arg Gln Ala Ser Ala Ser Arg Ala Trp Gly Leu Arg Phe Phe
                300                 305                 310

CGA AGC CCC CAG CAG GTG CTG CCC TCA CCA GAT GGG CGG CGG GCA GCA         1010
Arg Ser Pro Gln Gln Val Leu Pro Ser Pro Asp Gly Arg Arg Ala Ala
315                 320                 325                 330

GGT GTC CGC CTA GCA GTC ACT AGA CTG GAG GGT GTC GAT GAG GCC ACC         1058
Gly Val Arg Leu Ala Val Thr Arg Leu Glu Gly Val Asp Glu Ala Thr
                335                 340                 345

CGT GCA GTG CCC ACG GGA GAC ATG GAA GAC CTC CCT TGT GGG CTG GTG         1106
Arg Ala Val Pro Thr Gly Asp Met Glu Asp Leu Pro Cys Gly Leu Val
                350                 355                 360

CTC AGC AGC ATT GGG TAT AAG AGC CGC CCT GTC GAC CCA AGC GTG CCC         1154
Leu Ser Ser Ile Gly Tyr Lys Ser Arg Pro Val Asp Pro Ser Val Pro
                365                 370                 375

TTT GAC TCC AAG CTT GGG GTC ATC CCC AAT GTG GAG GGC CGG GTT ATG         1202
Phe Asp Ser Lys Leu Gly Val Ile Pro Asn Val Glu Gly Arg Val Met
                380                 385                 390

GAT GTG CCA GGC CTC TAC TGC AGC GGC TGG GTG AAG AGA GGA CCT ACA         1250
Asp Val Pro Gly Leu Tyr Cys Ser Gly Trp Val Lys Arg Gly Pro Thr
395                 400                 405                 410

GGT GTC ATA GCC ACA ACC ATG ACT GAC AGC TTC CTC ACC GGC CAG ATG         1298
Gly Val Ile Ala Thr Thr Met Thr Asp Ser Phe Leu Thr Gly Gln Met
                415                 420                 425

CTG CTG CAG GAC CTG AAG GCT GGG TTG CTC CCC TCT GGC CCC AGG CCT         1346
Leu Leu Gln Asp Leu Lys Ala Gly Leu Leu Pro Ser Gly Pro Arg Pro
                430                 435                 440

GGC TAC GCA GCC ATC CAG GCC CTG CTC AGC AGC CGA GGG GTC CGG CCA         1394
Gly Tyr Ala Ala Ile Gln Ala Leu Leu Ser Ser Arg Gly Val Arg Pro
                445                 450                 455

GTC TCT TTC TCA GAC TGG GAG AAG CTG GAT GCC GAG GAG GTG GCC CGG         1442
Val Ser Phe Ser Asp Trp Glu Lys Leu Asp Ala Glu Glu Val Ala Arg
                460                 465                 470

GGC CAG GGC ACG GGG AAG CCC AGG GAG AAG CTG GTG GAT CCT CAG GAG         1490
Gly Gln Gly Thr Gly Lys Pro Arg Glu Lys Leu Val Asp Pro Gln Glu
475                 480                 485                 490

ATG CTG CGC CTC CTG GGC CAC TGAGCCCAGC CCCAGCCCCG GCCCCCAGCA            1541
Met Leu Arg Leu Leu Gly His
```

```
                                    495
GGGAAGGGAT GAGTGTTGGG AGGGGAAGGG CTGGGTCCGT CTGAGTGGGA CTTTGCACCT   1601

CTGCTGATCC CGGCCGGCCC TGGCTTGGAG GCTTGGCTGC TCTTCCAGCG TCTCTCCTCC   1661

CTCCTGGGGA AGGTCGCCCT TGCGCGCAAG GTTTTAGCTT TCAGCAACTG AGGTAACCTT   1721

AGGGACAGGT GGAGGTGTGG GCCGATCTAA CCCCTTACCC ATCTCTCTAC TGCTGGACTG   1781

TGGAGGGTCA CCAGGTTGGG AACATGCTGG AAATAAAACA GCTGCACCCA AAAAAAAAA   1841

AAAAAAA                                                            1848
```

(2) INFORMATION FOR SEQ ID NO:4:

(i) SEQUENCE CHARACTERISTICS:
        (A) LENGTH: 497 amino acids
        (B) TYPE: amino acid
        (D) TOPOLOGY: linear (ii) MOLECULE TYPE: protein (xi) SEQUENCE DESCRIPTION: SEQ ID NO:4:

```
Met Ala Ser Arg Cys Trp Arg Trp Trp Gly Trp Ser Ala Trp Pro Arg
 1               5                  10                  15

Thr Arg Leu Pro Pro Ala Gly Ser Thr Pro Ser Phe Cys His His Phe
            20                  25                  30

Ser Thr Gln Glu Lys Thr Pro Gln Ile Cys Val Val Gly Ser Gly Pro
        35                  40                  45

Ala Gly Phe Tyr Thr Ala Gln His Leu Leu Lys His Pro Gln Ala His
    50                  55                  60

Val Asp Ile Tyr Glu Lys Gln Pro Val Pro Phe Gly Leu Val Arg Phe
65                  70                  75                  80

Gly Val Ala Pro Asp His Pro Glu Val Lys Asn Val Ile Asn Thr Phe
                85                  90                  95

Thr Gln Thr Ala His Ser Gly Arg Cys Ala Phe Trp Gly Asn Val Glu
            100                 105                 110

Val Gly Arg Asp Val Thr Val Pro Glu Leu Gln Glu Ala Tyr His Ala
        115                 120                 125

Val Val Leu Ser Tyr Gly Ala Glu Asp His Arg Ala Leu Glu Ile Pro
    130                 135                 140

Gly Glu Glu Leu Pro Gly Val Cys Ser Ala Arg Ala Phe Val Gly Trp
145                 150                 155                 160

Tyr Asn Gly Leu Pro Glu Asn Gln Glu Leu Glu Pro Asp Leu Ser Cys
                165                 170                 175

Asp Thr Ala Val Ile Leu Gly Gln Gly Asn Val Ala Leu Asp Val Ala
            180                 185                 190

Arg Ile Leu Leu Thr Pro Pro Glu His Leu Glu Ala Leu Leu Leu Cys
        195                 200                 205

Gln Arg Thr Asp Ile Thr Lys Ala Ala Leu Gly Val Leu Arg Gln Ser
    210                 215                 220

Arg Val Lys Thr Val Trp Leu Val Gly Arg Arg Gly Pro Leu Gln Val
225                 230                 235                 240

Ala Phe Thr Ile Lys Glu Leu Arg Glu Met Ile Gln Leu Pro Gly Ala
                245                 250                 255

Arg Pro Ile Leu Asp Pro Val Asp Phe Leu Gly Leu Gln Asp Lys Ile
            260                 265                 270

Lys Glu Val Pro Arg Pro Arg Lys Arg Leu Thr Glu Leu Leu Leu Arg
        275                 280                 285
```

```
Thr Ala Thr Glu Lys Pro Gly Pro Ala Glu Ala Ala Arg Gln Ala Ser
    290                 295                 300

Ala Ser Arg Ala Trp Gly Leu Arg Phe Phe Arg Ser Pro Gln Gln Val
305                 310                 315                 320

Leu Pro Ser Pro Asp Gly Arg Arg Ala Ala Gly Val Arg Leu Ala Val
                325                 330                 335

Thr Arg Leu Glu Gly Val Asp Glu Ala Thr Arg Ala Val Pro Thr Gly
            340                 345                 350

Asp Met Glu Asp Leu Pro Cys Gly Leu Val Leu Ser Ser Ile Gly Tyr
        355                 360                 365

Lys Ser Arg Pro Val Asp Pro Ser Val Pro Phe Asp Ser Lys Leu Gly
    370                 375                 380

Val Ile Pro Asn Val Glu Gly Arg Val Met Asp Val Pro Gly Leu Tyr
385                 390                 395                 400

Cys Ser Gly Trp Val Lys Arg Gly Pro Thr Gly Val Ile Ala Thr Thr
                405                 410                 415

Met Thr Asp Ser Phe Leu Thr Gly Gln Met Leu Leu Gln Asp Leu Lys
            420                 425                 430

Ala Gly Leu Leu Pro Ser Gly Pro Arg Pro Gly Tyr Ala Ala Ile Gln
        435                 440                 445

Ala Leu Leu Ser Ser Arg Gly Val Arg Pro Val Ser Phe Ser Asp Trp
    450                 455                 460

Glu Lys Leu Asp Ala Glu Val Ala Arg Gly Gln Gly Thr Gly Lys
465                 470                 475                 480

Pro Arg Glu Lys Leu Val Asp Pro Gln Glu Met Leu Arg Leu Leu Gly
                485                 490                 495

His (2) INFORMATION FOR SEQ ID NO:5:

(i) SEQUENCE CHARACTERISTICS:
        (A) LENGTH: 1464 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 133..684

(xi) SEQUENCE DESCRIPTION: SEQ ID NO:5:

GCCACTCCAG CCCCGCGCCC CTCGCCGCGG CCCTCGGCGT CTGCGCCGCA GCTGCCGCCC        60

CCGCCTCTTT GGAGTCTCTC GCGGCCTCAA AGCGCGGCCT GCGTCGCTTC CGGCAGTTCC      120

AGACCGCGGG CG ATG GCT GCC GCT GGG GGC GCC CGG CTG CTG CGC GCC         168
              Met Ala Ala Ala Gly Gly Ala Arg Leu Leu Arg Ala
                1               5                   10

GCT TCT GCT GTC CTC GGC GGC CCG GCC GGC CGG TGG CTG CAC CAC GCT        216
Ala Ser Ala Val Leu Gly Gly Pro Ala Gly Arg Trp Leu His His Ala
            15                  20                  25

GGG TCC CGC GCT GGA TCC AGC GGC CTG CTG AGG AAC CGG GGG CCG GGC        264
Gly Ser Arg Ala Gly Ser Ser Gly Leu Leu Arg Asn Arg Gly Pro Gly
30                  35                  40

GGG AGC GCG GAG GCG AGC CGG TCG CTG AGC GTG TCG GCG CGG GCC CGG        312
Gly Ser Ala Glu Ala Ser Arg Ser Leu Ser Val Ser Ala Arg Ala Arg
```

```
            45                  50                  55                  60
AGC AGC TCA GAA GAT AAA ATA ACA GTC CAC TTT ATA AAC CGT GAT GGT          360
Ser Ser Ser Glu Asp Lys Ile Thr Val His Phe Ile Asn Arg Asp Gly
                65                  70                  75

GAA ACA TTA ACA ACC AAA GGA AAA GTT GGT GAT TCT CTG CTA GAT GTT          408
Glu Thr Leu Thr Thr Lys Gly Lys Val Gly Asp Ser Leu Leu Asp Val
                    80                  85                  90

GTG GTT GAA AAT AAT CTA GAT ATT GAT GGC TTT GGT GCA TGT GAG GGA          456
Val Val Glu Asn Asn Leu Asp Ile Asp Gly Phe Gly Ala Cys Glu Gly
                95                  100                 105

ACC CTG GCT TGT TCA ACC TGT CAC CTC ATC TTT GAA GAT CAC ATA TAT          504
Thr Leu Ala Cys Ser Thr Cys His Leu Ile Phe Glu Asp His Ile Tyr
            110                 115                 120

GAG AAG TTA GAT GCA ATC ACT GAT GAG GAG AAT GAC ATG CTC GAT CTG          552
Glu Lys Leu Asp Ala Ile Thr Asp Glu Glu Asn Asp Met Leu Asp Leu
125                 130                 135                 140

GCA TAT GGA CTA ACA GAC AGA TCA CGG TTG GGC TGC CAA ATC TGT TTG          600
Ala Tyr Gly Leu Thr Asp Arg Ser Arg Leu Gly Cys Gln Ile Cys Leu
                    145                 150                 155

ACA AAA TCT ATG GAC AAT ATG ACT GTT CGA GTG CCT GAA ACA GTG GCT          648
Thr Lys Ser Met Asp Asn Met Thr Val Arg Val Pro Glu Thr Val Ala
                160                 165                 170

GAT GCC AGA CAA TCC ATT GAT GTG GGC AAG ACC TCC TGAACTAGAA              694
Asp Ala Arg Gln Ser Ile Asp Val Gly Lys Thr Ser
            175                 180

CAAATAGGAA TATTTTCATG GAATTTTACC TATTTTTATA ATTATTATTT CTTAAAGTGA        754

TTAAATGAGA ACATGGATGA GTGGACTTCA TATTATGACT AGCTTACTA TTTTAATTCA        814

CCTTGCATAA CTACTGAATT TTGTCATTCT TGAAAGTATG CAATTTTTAT TTTGGTTATA        874

TTACAAAAAT GTCAATCAAA TATTAAAAAA TAGTTAATGT GATAGAAAAA CCTACATATT        934

TTTTTTCTAG TTTGTTTAGC GACTTAGCAA AATGTTTTCA TATGGTCTCA TCTGTTTACC        994

TAGAAGATAG GTTAAGGAAA TATAGTATTA TTCCTGTTTG ATGTGGTTGA AGGCAGAGAT       1054

CTAACCTGGC TTGTTTAGGG CCATACCACT AATTAGAAAA TCTGTGCTAG AACCTGTGTC       1114

TTATTCCTAT AAGCTATGTG TTCAGACTGA AACTGGAGAA ATTATGACTA TTTTATTTAT       1174

AGTAGTAGTT AAATCTGAAT GTGTATGGAC AAAAATATTT AATTGCTCAG TAAACTGCTT       1234

AACTTCAAAG ATAGTTATTG ACCTTATAAA TAAATATTTC AAAATTTTGA TTCGGAAGAC       1294

TAAGTCTGGA CGTAGACATT ATAATGCTAT CAAAGAAGTT TGATCTCTGT TTTGACTAAA       1354

CTAGAGGAAA AATGATTGGA TGTGTTTATT CTTTTCTAAG CAGAATGGTT TAACTTTGTA       1414

CTCTTTGAAA AATAATGCTG ATTTATAAAT CTCTGCCTAT AACAGAATGG                  1464

(2) INFORMATION FOR SEQ ID NO:6:

(i) SEQUENCE CHARACTERISTICS:
        (A) LENGTH: 184 amino acids
        (B) TYPE: amino acid
        (D) TOPOLOGY: linear (ii) MOLECULE TYPE: protein (xi) SEQUENCE DESCRIPTION: SEQ ID NO:6:

Met Ala Ala Ala Gly Gly Ala Arg Leu Leu Arg Ala Ala Ser Ala Val
1               5                   10                  15

Leu Gly Gly Pro Ala Gly Arg Trp Leu His His Ala Gly Ser Arg Ala
                20                  25                  30

Gly Ser Ser Gly Leu Leu Arg Asn Arg Gly Pro Gly Gly Ser Ala Glu
            35                  40                  45
```

```
Ala Ser Arg Ser Leu Ser Val Ser Ala Arg Ala Arg Ser Ser Ser Glu
        50                  55                  60

Asp Lys Ile Thr Val His Phe Ile Asn Arg Asp Gly Glu Thr Leu Thr
65                      70                  75                  80

Thr Lys Gly Lys Val Gly Asp Ser Leu Leu Asp Val Val Val Glu Asn
                    85                  90                  95

Asn Leu Asp Ile Asp Gly Phe Gly Ala Cys Glu Gly Thr Leu Ala Cys
                100                 105                 110

Ser Thr Cys His Leu Ile Phe Glu Asp His Ile Tyr Glu Lys Leu Asp
            115                 120                 125

Ala Ile Thr Asp Glu Glu Asn Asp Met Leu Asp Leu Ala Tyr Gly Leu
        130                 135                 140

Thr Asp Arg Ser Arg Leu Gly Cys Gln Ile Cys Leu Thr Lys Ser Met
145                 150                 155                 160

Asp Asn Met Thr Val Arg Val Pro Glu Thr Val Ala Asp Ala Arg Gln
                    165                 170                 175

Ser Ile Asp Val Gly Lys Thr Ser
                180

(2) INFORMATION FOR SEQ ID NO:7:

(i) SEQUENCE CHARACTERISTICS:
        (A) LENGTH: 33 base pairs
        (B) TYPE: nucleic acid
        (C) STRANDEDNESS: both
        (D) TOPOLOGY: linear (ii) MOLECULE TYPE: DNA (synthetic)

(xi) SEQUENCE DESCRIPTION: SEQ ID NO:7:

AGCTTGGTAC CACTAGTGCT AGCTGACTGA CTG                                    33

(2) INFORMATION FOR SEQ ID NO:8:

(i) SEQUENCE CHARACTERISTICS:
        (A) LENGTH: 33 base pairs
        (B) TYPE: nucleic acid
        (C) STRANDEDNESS: both
        (D) TOPOLOGY: linear (ii) MOLECULE TYPE: DNA (synthetic)

(xi) SEQUENCE DESCRIPTION: SEQ ID NO:8:

AATTCAGTCA GTCAGCTAGC ACTAGTGGTA CCA                                    33

(2) INFORMATION FOR SEQ ID NO:9:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:9:

Thr Asp Gly Thr Ser
1               5

(2) INFORMATION FOR SEQ ID NO:10:

(i) SEQUENCE CHARACTERISTICS:
        (A) LENGTH: 5 amino acids
        (B) TYPE: amino acid
        (D) TOPOLOGY: linear
```

(ii) MOLECULE TYPE: peptide (xi) SEQUENCE DESCRIPTION: SEQ ID NO:10:

Thr Asp Gly Ala Ser
1               5

(2) INFORMATION FOR SEQ ID NO:11:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:11:

GGGTACCATG CTGGCCAAGG GTC                                      23

(2) INFORMATION FOR SEQ ID NO:12:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:12:

GACTAGTGCC GTCGGTCTGC TGGGTTGCTT CCTG                         34

(2) INFORMATION FOR SEQ ID NO:13:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:13:

GACTAGTTCC ACACAGGAGA AGACC                                    25

(2) INFORMATION FOR SEQ ID NO:14:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:14:

TGACATTCTT CACCTCGGG                                          19

(2) INFORMATION FOR SEQ ID NO:15:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:15:

```
GTATAAGAGC CGCCCTGTCG AC                                              22

(2) INFORMATION FOR SEQ ID NO:16:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:16:

GGCTAGCGCC GTCGGTGTGG CCCAGGAGGC GCAG                                  34

(2) INFORMATION FOR SEQ ID NO:17:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:17:

GGCTAGCAGC AGCTCAGAAG AT                                              22

(2) INFORMATION FOR SEQ ID NO:18:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:18:

GGGCTAGCGC CGTCGGTGGA GGTCTTGCCC AC                                    32

(2) INFORMATION FOR SEQ ID NO:19:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:19:

GACTAGTATT CAGACATTGA CCTCC                                           25

(2) INFORMATION FOR SEQ ID NO:20:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:20:

CAACCCCAGC TCAAAGATGC                                                 20

(2) INFORMATION FOR SEQ ID NO:21:
```

(i) SEQUENCE CHARACTERISTICS:
    (A) LENGTH: 25 base pairs
    (B) TYPE: nucleic acid
    (C) STRANDEDNESS: single
    (D) TOPOLOGY: linear (ii) MOLECULE TYPE: DNA (synthetic)

(xi) SEQUENCE DESCRIPTION: SEQ ID NO:21:

GGGTACCATG GAGCCCAGTA TCTTG                                              25

(2) INFORMATION FOR SEQ ID NO:22:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:22:

GACTAAGAGT AACAAGAAGC C                                                  21

(2) INFORMATION FOR SEQ ID NO:23:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:23:

ATCTCCACCC GCAGTCCTCG C                                                  21

(2) INFORMATION FOR SEQ ID NO:24:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:24:

TTGGGGCCCT CGGACTTAAA G                                                  21